United States Patent [19]

Chu et al.

[11] Patent Number: 5,137,892
[45] Date of Patent: Aug. 11, 1992

[54] QUINOLINE, NAPHTHYRIDINE AND PYRIDOBENZOXAZINE DERIVATIVES

[75] Inventors: Daniel T. Chu, Vernon Hills; Curt S. Cooper, Lake Bluff, both of Ill.

[73] Assignee: Abbott Laboratories, Abbott Park, Ill.

[21] Appl. No.: 626,602

[22] Filed: Dec. 12, 1990

[51] Int. Cl.$^5$ .............. C07D 405/14; C07D 401/10; C07D 455/06; A61K 31/47

[52] U.S. Cl. ................... 514/278; 514/312; 546/15; 546/19; 546/95; 546/123; 546/169; 546/170; 546/278; 546/290; 546/300; 546/312; 544/32; 544/33; 544/63; 544/89; 544/101; 548/409; 548/541

[58] Field of Search .............. 546/15, 123, 169, 170, 546/278, 300, 312; 514/278, 312

[56] References Cited

U.S. PATENT DOCUMENTS 4,929,613  5/1990  Culbertson et al. ............... 514/210

FOREIGN PATENT DOCUMENTS 326916   8/1989  European Pat. Off. .
357047   3/1990  European Pat. Off. .
3420743  12/1985 Fed. Rep. of Germany .
90/06307 6/1990  PCT Int'l Appl. .

Primary Examiner—Mark L. Berch
Attorney, Agent, or Firm—Andreas M. Danckers

[57] ABSTRACT

Novel antibacterial compounds are disclosed having the formula

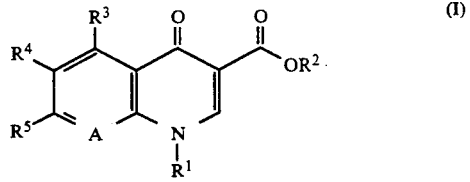

as well as pharmaceutically acceptable salts, esters, amide and prodrugs thereof, wherein $R^1$ is selected from the group consisting of (a) lower alkyl, (b) halo(lower alkyl), (c) lower alkyl-(alkynyl), (d) lower cycloalkyl, (e) lower alkylamino, (f) nitrogen-containing aromatic heterocycle, (g) bicyclic alkyl and (h) phenyl;

$R^2$ is selected from the group consisting of hydrogen, lower alkyl, a pharmaceutically acceptable cation, and a prodrug ester group;

$R^3$ and $R^4$ are independently selected from the group consisting of hydrogen, halogen, amino, and lower alkyl;

$R^5$ is either a nitrogen-containing heterocycle or a nitrogen-containing spiro-bicyclic-heterocycle; and A is N or C—$R^6$, wherein $R^6$ is selected from the group consisting of hydrogen, halogen, lower alkyl, and lower alkoxy, or $R^1$ and $R^6$ taken together with the atoms to which they are attached form a 6-membered ring which may contain an oxygen or sulfur atom and which may be substituted with lower alkyl; as well as pharmaceutical compositions comprising such novel compounds and the thereapeutic use thereof.

10 Claims, No Drawings

QUINOLINE, NAPHTHYRIDINE AND PYRIDOBENZOXAZINE DERIVATIVES

TECHNICAL FIELD

This invention relates to novel compounds having antimicrobial activity, compositions containing such compounds and the use of thereof in treatment. More particularly, the present invention concerns novel ketal-substituted quinoline, naphthyridine and pyridobenzoxazine compounds, pharmaceutical compositions containing these compounds and a method of treating or preventing microbial infections using such compounds.

BACKGROUND OF THE INVENTION

Quinolone and naphthyridine carboxylic acids and their analogs are known antibacterial agents useful in human and animal applications, as for example aquaculture. Much work has been directed to the synthesis of derivatives thereof with the intention of obtaining compounds which exhibit improved activity against a broad spectrum of pathogens. Moreover, many such compounds have only limited solubility in water and thus exhibit reduced oral bioavailability.

Investigations of structure-activity relationship in the case of quinolones have in many instances focused on 7-substituted derivatives. Petersen et al., in European Patent Application No. 0326916, published Aug. 9, 1989, have disclosed the use of certain 7-pyrrolidine- and 7-azaspiro[4.4]nonane-substituted quinoline derivatives which are said to be useful as antibacterial agents and animal growth promoters, as well as the synthesis of 1-cyclopropyl-7-(1,4-dioxa-7-azaspiro[4.4]non-7-yl)-6-fluoro-1,4-dihydro-4-oxo-3-quinoline carboxylic acid.

The ethyl ester of this latter compound was reported earlier by Culbertson et al. in U.S. Pat. No. 4,929,613, issued May 29, 1990, as an intermediate in the preparation of other quinolone compounds.

The Daiichi Pharmaceutical Co., Ltd., in European Patent Application No. 0357047, published Mar. 7, 1990, has disclosed certain non-oxygen-containing azaspiro-substituted quinoline derivatives useful as antibacterial agents.

Additionally, Petersen et al. have also disclosed, in German Patent Application No. 3420743, published Dec. 5, 1985, a 7-piperazinyl quinolone compound that has a p-methylene group substituted with a 1,4-dioxaspiro[4.5]decane. This compound apparently was prepared as an intermediate to other compounds of that reference.

Despite these efforts, however, there remains a need for improved derivatives of quinolones and analogs thereof, effective against a broad spectrum of microorganisms and having enhanced solubility and biological activity.

SUMMARY OF THE INVENTION

The present invention comprises novel quinoline, naphthyridine and pyridobenzoxazine derivatives having unexpected activity against a wide variety of microbial pathogens, as well as improved solubility. In one aspect of the invention are provided derivatives of the formula (I)

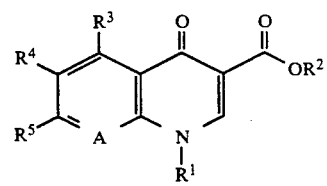

and pharmaceutically acceptable salts, esters, amides or prodrugs thereof.

In these compounds, $R^1$ is selected from (a) lower alkyl, (b) halo(lower alkyl), (c) lower alkyl(alkynyl), (d) lower cycloalkyl, (e) lower alkylamino, (f) nitrogen-containing aromatic heterocycle, (g) bicyclic alkyl and (h) phenyl.

$R^2$ in Formula (I) may be hydrogen, lower alkyl, or a pharmaceutically acceptable cation.

$R^3$ and $R^4$ in Formula (I) are independently selected from the group consisting of hydrogen, halogen, amino and lower alkyl.

$R^5$ in Formula (I) is selected from either (a) a nitrogen-containing heterocycle having the formula

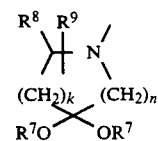

wherein $k=1$ or 2, $n=1$ or 2 and $k+n=2$ or 3; $R^7$ is lower alkyl; and $R^8$ and $R^9$ are independently selected from the group consisting of hydrogen, amino, lower alkylamino, amino(lower alkyl), lower alkyl, halo(lower alkyl), amino acid-substituted amino, and amino acid-substituted amino(lower alkyl); or (b) a nitrogen-containing spiro-bicyclic-heterocycle having the formula

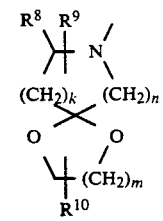

wherein $k=1$ or 2, $n=1$ or 2 and $k+n=2$ or 3; $m=1$ or 2; $R^8$ and $R^9$ are independently selected from the group consisting of hydrogen, amino, lower alkylamino, amino(lower alkyl), halo(lower alkyl), amino acid-substituted amino, or amino acid-substituted amino(lower alkyl); and $R^{10}$ is selected from the group consisting of hydrogen, amino, lower alkylamino, amino(lower alkyl), lower alkyl, halo(lower alkyl), hydroxy(lower alkyl), lower alkoxy(lower alkyl), amino acid-substituted amino, or amino acid-substituted amino(lower alkyl).

A in Formula (I) is N or C—$R^6$, wherein $R^6$ is selected from the group consisting of hydrogen, halogen, lower alkyl, or lower alkoxy Additionally, the compounds of the present invention are subjected to the proviso that when $R^5$ is a nitrogen-containing spiro-bicyclic-heterocycle having the formula

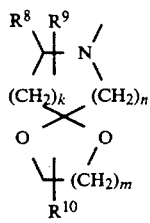

where k=1, n=1, and m=1 and $R^{10}$ is hydrogen, then $R^8$ and $R^9$ may not be hydrogen and hydrogen, hydrogen and lower alkyl, or lower alkyl and hydrogen, respectively.

It has been found that the compounds of the present invention possess antibacterial activity against a wide spectrum of Gram-positive and Gram-negative bacteria as well as enterobacteria. Susceptible organisms include those Gram-positive or Gram-negative aerobic and anaerobic organisms whose growth can be inhibited by the compounds of the invention such as Staphylococcus, Lactobacillus, Micrococcus, Enterococcus, Streptococcus, Sarcinia, Escherichia, Enterobacter, Klebsiella, Pseudomonas, Acinetobacter, Proteus, Providencia, Citrobacter, Nisseria, Baccillus, Bacteroides, Campylobacter, Peptococcus, Clostridium, Salmonella, Shigella, Legionella, Serratia, Haemophilus and Brucella species and other organisms.

The compounds of this invention are thus useful in the antibiotic treatment and prevention of susceptible bacterial infections in both humans and animals. In addition, the compounds may be used in scrub solutions for surface inhibition of bacterial growth by reason of their in vitro activity.

In a further aspect of the present invention are disclosed compositions comprising a therapeutically effective amount of a compound of the invention in combination with a pharmaceutically acceptable carrier or diluent.

In yet another aspect of the present invention is disclosed the therapeutic and prophylactic treatment of bacterial infections in an animal host, including but not limited to humans, in need of such treatment, by the administration thereto of a therapeutically effective amount of a compound of the invention.

DETAILED DESCRIPTION OF THE INVENTION

In a first aspect of the present invention, novel compounds are disclosed which have the formula

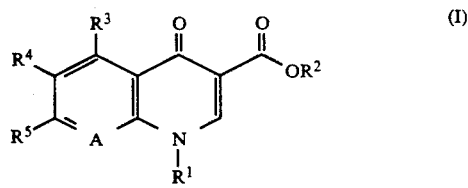

or which are pharmaceutically acceptable salts, esters, amides or prodrugs thereof, wherein $R^1$ is selected from the group consisting of (a) lower alkyl, (b) halo(lower alkyl), (c) lower alkyl-(alkynyl), (d) lower cycloalkyl, (e) lower alkylamino, (f) nitrogen-containing aromatic heterocycle, (g) bicyclic alkyl and (h) phenyl;

$R^2$ is selected from the group consisting of hydrogen, lower alkyl, a pharmaceutically acceptable cation, and a prodrug ester group;

$R^3$ and $R^4$ are independently selected from the group consisting of hydrogen, halogen, amino, and lower alkyl;

$R^5$ is selected from the group consisting of
(a) a nitrogen-containing heterocycle having the formula

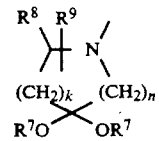

wherein k=1 or 2, n=1 or 2 and k+n=2 or 3; $R^7$ is lower alkyl; and $R^8$ and $R^9$ are independently selected from the group consisting of hydrogen, amino, lower alkylamino, amino(lower alkyl), lower alkyl, halo(lower alkyl), amino acid-substituted amino, and amino acid-substituted amino(-lower alkyl); and (b) a nitrogen-containing spiro-bicyclic-heterocycle having the formula

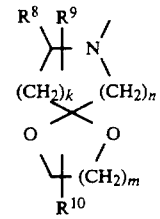

wherein k=1 or 2, n=1 or 2 and k+n=2 or 3; m=1 or 2; $R^8$ and $R^9$ are independently selected from the group consisting of hydrogen, amino, lower alkylamino, amino(lower alkyl), halo(lower alkyl), amino acid-substituted amino, and amino acid-substituted amino(lower alkyl); and $R^{10}$ is selected from the group consisting of hydrogen, amino, lower alkylamino, amino(lower alkyl), lower alkyl, halo(lower alkyl), hydroxy(lower alkyl), lower alkoxy(lower alkyl), amino acid-substituted amino, and amino acid-substituted amino(-lower alkyl); and A is N or C—$R^6$, wherein $R^6$ is selected from the group consisting of hydrogen, halogen, lower alkyl, and lower alkoxy, or $R^1$ and $R^6$ taken together with the atoms to which they are attached form a 6-membered ring which may contain an oxygen or sulfur atom and which may be substituted with lower alkyl;

with the proviso that when $R^5$ is a nitrogen-containing spiro-bicyclic-heterocycle having the formula

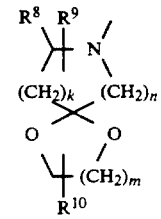

where k=1, n=1, m=1 and $R^{10}$ is hydrogen, and where either of $R^8$ and $R^9$ are hydrogen, then the other of $R^8$ and $R^9$ may not be hydrogen or lower alkyl.

Representative examples of the compounds of the invention are the following:

7-(3,3-dimethoxypyrrolidin-1-yl)-1-(2,4-difluorophenyl)-6-fluoro-1,4-dihydro-4-oxo-3-quinolinecarboxylic acid;

1-cyclopropyl-7-(3,3-dimethoxypyrrolidin-1-yl)-6-fluoro-1,4-dihydro-4-oxo-3-quinolinecarboxylic acid;

1-(2,4-difluorophenyl)-7-(1,5-dioxa-8-azaspiro[5.4]dec-8-yl)-6-fluoro-1,4-dihydro-4-oxo-3-quinolinecarboxylic acid;

1-cyclopropyl-6,8-difluoro-7-(1,5-dioxa-8-azaspiro[5.4]-dec-8-yl)-1,4-dihydro-4-oxo-3-quinolinecarboxylic acid;

1-(2,4-difluorophenyl)-7-(1,4-dioxa-2-methyl-7-azaspiro[4.4]non-7-yl)-6-fluoro-1,4-dihydro-4-oxo-3-quinolinecarboxylic acid;

1-(2,4-difluorophenyl)-7-(1,4-dioxa-2-hydroxymethyl-7-azaspiro[4.4]non-7-yl)-6-fluoro-1,4-dihydro-4-oxo-3-quinolinecarboxylic acid;

1-(2,4-difluorophenyl)-7-(2-aminomethyl-1,4-dioxa-7-azaspiro[4.4]non-7-yl)-6-fluoro-1,4-dihydro-4-oxo-3-quinolinecarboxylic acid dihydrochloride;

1-(2,4-difluorophenyl)-7-(2-dimethylaminomethyl-1,4-dioxa-7-azaspiro[4.4]non-7-yl)-6-fluoro-1,4-dihydro-4-oxo-3-quinolinecarboxylic acid;

7-(3,3-dimethoxy-4-methylpyrrolidin-1-yl)-1-(2,4-difluorophenyl)-6-fluoro-1,4-dihydro-4-oxo-3-quinolinecarboxylic acid;

1-cyclopropyl-6,8-difluoro-7-(3,3-dimethoxy-4-methylpyrrolidin-1-yl)-1,4-dihydro-4-oxo-3-quinolinecarboxylic acid;

1-(2,4-difluorophenyl)-7-(1,5-dioxa-9-azaspiro[5.5]undec-9-yl)-6-fluoro-1,4-dihydro-4-oxo-3-quinolinecarboxylic acid;

1-cyclopropyl-6-fluoro-7-(9-amino-1,4-dioxa-7-azaspiro[4.4]non-7-yl)-1,4-dihydro-4-oxo-3-quinolinecarboxylic acid hydrochloride;

1-cyclopropyl-6,8-difluoro-7-(9-amino-1,4-dioxa-7-azaspiro[4.4]non-7-yl)-1,4-dihydro-4-oxo-3-quinolinecarboxylic acid;

(R)-10-(1,4-dioxa-2-methyl-7-azaspiro[4.4]non-7-yl)-9,10-difluoro-2,3-dihydro-3-methyl-7-oxo-7H-pyrido[1,2,3-de]-1,4-benzoxazine-6-carboxylic acid;

(R)-10-(1,5-dioxa-9-azaspiro[5.5]undec-9-yl)-9,10-difluoro-2,3-dihydro-3-methyl-7-oxo-7H-pyrido[1,2,3-de]-1,4-benzoxazine-6-carboxylic acid;

1-(2,4-difluorophenyl)-7-(3,3-dimethoxypyrrolidin-1-yl)-6-fluoro-1,8-naphthyridine-3-carboxylic acid;

1-(2,4-difluorophenyl)-7-(1,5-dioxa-8-azaspiro[5.4]dec-8-yl)-6-fluoro-1,8-naphthyridine-3-carboxylic acid;

1-(2,4-difluorophenyl)-7-(1,4-dioxa-2-methyl-7-azaspiro[4.4]non-7-yl)-6-fluoro-1,8-naphthyridine-3-carboxylic acid;

7-(1,4-dioxa-2-methyl-7-azaspiro[4.4]non-7-yl)-6-fluoro-1-(4-fluorophenyl)-1,8-naphthyridine-3-carboxylic acid;

7-(2-aminomethyl-1,4-dioxa-7-azaspiro[4.4]non-7-yl)-6-fluoro-1-(2,4-difluorophenyl)-1,8-naphthyridine-3-carboxylic acid dihydrochloride;

7-(3,3-dimethoxy-4-methylpyrrolidin-1-yl)-6-fluoro-1-(2,4-difluorophenyl)-1,8-naphthyridine-3-carboxylic acid;

7-(2-dimethylaminomethyl-1,4-dioxa-7-azaspiro[4.4]non-7-yl)-6-fluoro-1-(2,4-difluorophenyl)-1,8-naphthyridine-3-carboxylic acid;

7-(9-amino-1,4-dioxa-7-azaspiro[4.4]non-7-yl)-6-fluoro-1-(2,4-difluorophenyl)-1,8-naphthyridine-3-carboxylic acid hydrochloride;

7-(9-aminomethyl-1,4-dioxa-7-azaspiro[4.4]non-7-yl)-6-fluoro-1-(2,4-difluorophenyl)-1,8-naphthyridine-3-carboxylic acid hydrochloride;

7-(1,5-dioxa-9-azaspiro[5.5]undec-9-yl)-6-fluoro-1-(2,4-difluorophenyl)-1,8-naphthyridine-3-carboxylic acid;

7-(2-aminomethyl-1,4-dioxa-8-azaspiro[4.5]dec-8-yl)-6-fluoro-1-(2,4-difluorophenyl)-1,8-naphthyridine-3-carboxylic acid hydrochloride;

7-(1,5-dioxa-9-azaspiro[5.5]undec-9-yl)-6-fluoro-1-(2,4-difluorophenyl)-1,8-naphthyridine-3-carboxylic acid;

7-(2-aminomethyl-1,4-dioxa-8-azaspiro[4.5]dec-8-yl)-6-fluoro-1-(2,4-difluorophenyl)-1,8-naphthyridine-3-carboxylic acid hydrochloride;

1-(2,4-difluorophenyl)-6-fluoro-7-(2-methylaminomethyl-1,4-dioxa-8-azaspiro[4.5]dec-8-yl)-1,8-naphthyridine-3-carboxylic acid hydrochloride;

1-(2,4-difluorophenyl)-6-fluoro-7-(2-methylaminomethyl-1,4-dioxa-8-azaspiro[4.5]dec-8-yl)-1,8-naphthyridine-3-carboxylic acid;

7-(2-aminomethyl-1,4-dioxa-7-azaspiro[4.4]non-7-yl)-1-cyclopropyl-6-fluoro-1,8-naphthyridine-3-carboxylic acid dihydrochloride;

7-(2-dimethylaminomethyl-1,4-dioxa-7-azaspiro[4.4]-non-7-yl)-1-cyclopropyl-6-fluoro-1,8-naphthyridine-3-carboxylic acid;

7-(9-aminomethyl-1,4-dioxa-7-azaspiro[4.4]non-7-yl)-1-cyclopropyl-6-fluoro-1,8-naphthyridine-3-carboxylic acid hydrochloride;

and pharmaceutically acceptable salts, esters, amides and prodrugs thereof.

Of these, preferred examples of the compounds of the invention include 1-cyclopropyl-6,8-difluoro-7-(9-amino-1,4-dioxa-7-azaspiro[4.4]non-7-yl)-1,4-dihydro-4-oxo-3-quinolinecarboxylic acid (Example 274, below), and 7-(2-dimethylaminomethyl-1,4-dioxa-7-azaspiro[4.4]non-7-yl)-6-fluoro-1-(2,4-difluorophenyl)-1,8-naphthyridine-3-carboxylic acid (Example 445, below).

In a second aspect of the present invention are disclosed compositions useful in therapeutic and prophylactic treatment of microbial infections. These compositions comprise a therapeutically effective amount of a compound of the invention in combination with a pharmaceutically acceptable carrier.

In a third aspect of the present invention is disclosed a method for treating or preventing bacterial infections in a human or other animal host, comprising administering a therapeutically effective amount of a compound of the invention to an subject in need thereof.

Certain terms used throughout this disclosure and in the appended claims are defined as follows:

The term "alkanoyl of from 1 to 8 carbons" as used herein refers to a substituent of the formula $R^{11}C(O)$— wherein $R^{11}$ is hydrogen or an alkyl group of from 1 to 7 carbon atoms, and includes acetyl and pivaloyl.

The term "amino" refers to an amino group which may have one or two lower alkyl sustituents or one substituent alkanoyl group of from 1 to 8 carbons.

The terms "amino acid-substituted amino" and "amino acid-substituted amino(lower alkyl)" refer to amino groups, as defined herein, that are substituted by amide linkages to the carboxyl functions of amino acids or peptides of from 2-5 amino acid residues in length. The amino acids may be naturally occurring amino acids such as valine or leucine or they may be synthetic alpha amino acids such as cyclohexylalanine. The amino acids can either be in the L or D configuration or a mixture of the two isomers. Usually, the amino acid substituents are optically active and have the L configuration.

The term "amino(loweralkyl)" refers to lower alkyl groups, as defined below, having at least one amino substituent, which may have one or two lower alkyl substituents. Examples of amino(loweralkyl) groups include aminoethyl, aminomethyl, N,N-dimethylaminomethyl, and the like.

The term "aromatic group" refers to a C6 to C10 cyclic group which is aromatic according to Huckel's rule, as for example phenyl or naphthyl.

The term "bicyclic alkyl" refers to two fused rings comprising lower cycloalkyl groups, as defined below, including, but not limited to, bicyclo[1.1.1]pent-1-yl, bicyclo[1.1.1]pent-2-yl and the like.

The term "halogen" refers to bromo (Br), chloro (Cl), fluoro (F) and iodo (I).

The term "halo(lower alkyl)" refers to a lower alkyl group, as defined above, in which at least one hydrogen atom is replaced with a halogen atom. Examples of halo(lower alkyl) groups include fluoromethyl, trifluoromethyl, fluoroethyl and the like.

The term "hydroxy(lower alkyl)" refers to lower alkyl groups, as defined below, having at least one hydroxyl substituent, as for example hydroxyethyl.

The term "lower alkoxy" refers to alcohol groups substituted with a lower alkyl group, as defined below, as for example methoxy or ethoxy.

The term "lower alkoxy(lower alkyl)" refers to lower alkyl groups, as defined below, which are substituted with one or more lower alkoxy groups, as defined above, such as methoxymethyl, methoxyethyl or t-butoxyethyl.

The term "lower alkyl" refers to branched or straight chain lower alkyl groups containing one to six carbon atoms, including, but not limited to, methyl, ethyl, propyl, isopropyl, n-butyl, t,butyl,neopentyl and the like.

The term "lower alkyl(alkynyl) refers to straight chain alkyl groups of three to five carbon atoms containing a triple bond and substituted with one or more lower alkyl groups, as defined above, including but not limited to 3-methyl-1-butyn-3-yl, 3-methyl-1-pentyn-4-yl and the like.

The term "lower alkylamino" refers to amino groups substituted with one to three lower alkyl groups, as defined above, including methylamino, ethylamino, dimethylamino, propylamino and ethylmethylamino.

The term "lower cycloalkyl" refers to saturated monocyclic hydrocarbon groups having from 3 to 7 carbon atoms in the ring, as for example cyclopropyl, cyclobutyl, cyclobutyl, cyclopentyl, cyclohexyl, or cycloheptyl.

The term "nitrogen-containing aromatic heterocycle" refers to monocyclic aromatic ring systems having from five to seven ring atoms of which one, two or three ring atoms are independently hetero atoms such as S, O or N, at least one of the heteroatoms being nitrogen, with the remaining atoms being carbon. Examples include pyridine, pyrazine, pyrimidine, pyrrole, pyrazole, imidazole, thiazole, oxazole, iso-oxazole and substituted derivatives thereof.

The term "pharmaceutically acceptable cation" refers to a positively charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylammonium, tetraalkylammonium, and guanidinium ions and protonated forms of lysine, choline and procaine. Cations may be interchanged by methods known in the art, such as ion exchange. Where compounds of Formula (I) are prepared in the carboxylic acid form (that is, where $R^2$ is hydrogen) addition of a base form of the cation (such as a hydroxide of a free amine) will yield the appropriate cationic form.

The term "pharmaceutically acceptable salts, esters and amides" refers to those carboxylate salts, amino acid addition salts, esters and amides of the compounds of Formula (I) which are, within the scope of sound medical judgement, suitable for use in contact with the tissues of humans and animals without undue toxicity, irritation, allergic response, and the like, commensurate with a reasonable benefit/risk ratio, and effective for their intended use, as well as the zwitterionic forms of the compounds of Formula (I).

Pharmaceutically acceptable salts are well known in the art. For example, S. M. Berge, et al. describe pharmaceutically acceptable salts in detail in *J. Pharmaceutical Sciences*, 66: 1–19, 1977. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, alginate, cyclopentanepropionate, digluconate, dodecylsulfate, ethanesulfonate, hemisulfate, heptanoate, hexanoate, 2-naphthalenesulfonate, pamoate, persulfate, pivalate, propionate, undecanoate salts and the like, and they may be prepared according to conventional methods. Representative alkali or alkaline earth metal salts include sodium, calcium, potassium, magnesium salts and the like. Further pharmaceutically acceptable salts include, when appropriate, quaternary ammonium salt compounds formed using counterions such as halide, hydroxide, carboxylate, sulfate, phosphate, nitrate, loweralkyl sulfonate and arysulfonate.

As used herein, the term "pharmaceutically acceptable carrier" means a non-toxic, inert solid, semi-solid or liquid filler, diluent, encapsulating material or formulation auxiliary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

Examples of "pharmaceutically acceptable esters" of the compounds of Formula (I) include C1 to C6 alkyl esters wherein the alkyl group is straight or branched chain. Acceptable esters also include C5 to C7 acycloalkyl esters, while C1 to C4 esters are preferred. Esters may be prepared according to conventional methods.

Examples of "pharmaceutically acceptable amides" of the compounds of Formula (I) include amides derived from ammonia, primary C1 to C6 alkyl amines and secondary C1 to C6 dialkyl amines wherein the alkyl groups are straight or branched chain. In the case of secondary amines, the amine may also be in the form of a 5- or 6-membered heterocycle containing one nitrogen atom. Amides derived from ammonia, C1 to C3 alkyl primary amides and C1 to C2 dialkyl secondary amides are preferred. Amides of the compounds of Formula (I) may be prepared according to coventional methods. It is understood that amides of the compounds of the present invention include amino acid and peptide derivatives.

The term "phenyl" refers to both unsubstituted benzene rings and to benzene rings having one to three non-hydrogen substituents independently selected from the group consisting of halogen, hydroxy, lower alkoxy, lower alkyl, hydroxy-substituted lower alkyl, amino, lower alkylamino, amino(loweralkyl) and a nitrogen-containing heterocycle, as for example aziridinyl, pyrrolidinyl, piperidinyl and the like.

The term "prodrug" refers to compounds that are rapidly transformed in vivo to yield the parent compounds of Formula (I), as for example by hydrolysis in blood. T. Higuchi and V. Stella provide a thorough discussion of the prodrug concept in "Prodrugs as Novel Delivery Systems, Vol. 14 of the A.C.S. Symposium Series, American Chemical Society (1975). Examples of esters useful as prodrugs for compounds containing carboxyl groups can be found on pages 14–21 of "Bioreversible Carriers in Drug Design: Theory and Application," edited by E. B. Roche, Pergamon Press (1987).

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

The term "protecting group" is well known in the art and refers to sustituents on functional groups of compounds undergoing chemical transformation which prevent undesired reactions and degradations during a synthesis; see, for example, T. H. Greene, "Protective Groups in Organic Synthesis," John Wiley & Sons, (1981).

By a "therapeutically effective amount" of the compound of the invention is meant a sufficient amount of the compound to treat disorders, at a reasonable benefit/risk ratio applicable to any medical treatment. It will be understood, however, that the total daily usage of the compounds and compositions of the present invention is to be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts of, for example, from about 0.01 to about 50 mg/kg body weight, or more usually from about 0.2 to about 30 mg/kg body weight. Single dose compositions may contain such amounts or submultiples thereof to make up the daily dose. In general, treatment regimens according to the present invention comprise administering to a patient in need of such treatment from about 20 mg to about 2000 mg of the compound(s) of this invention per day in multiple doses or in a single dose.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsifying and suspending agents; and sweetening, flavoring and perfuming agents.

Injectable preparations, as for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, as for example by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at room temperature but liquid at body temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons or suitable alternatives.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

The compounds of this invention may be administered alone or in combination or in concurrent therapy with other agents.

In general, the compounds of the present invention are synthesized according to reaction Schemes 1, 2 and 3 presented below, in which A, k, m, n and $R^1$-$R^{10}$, as used herein, correspond to the groups identified in connection with Formula (I) above, Z is an amine protecting group, Y is a hydroxy protecting group and L is a good leaving group, as for example a halogen atom.

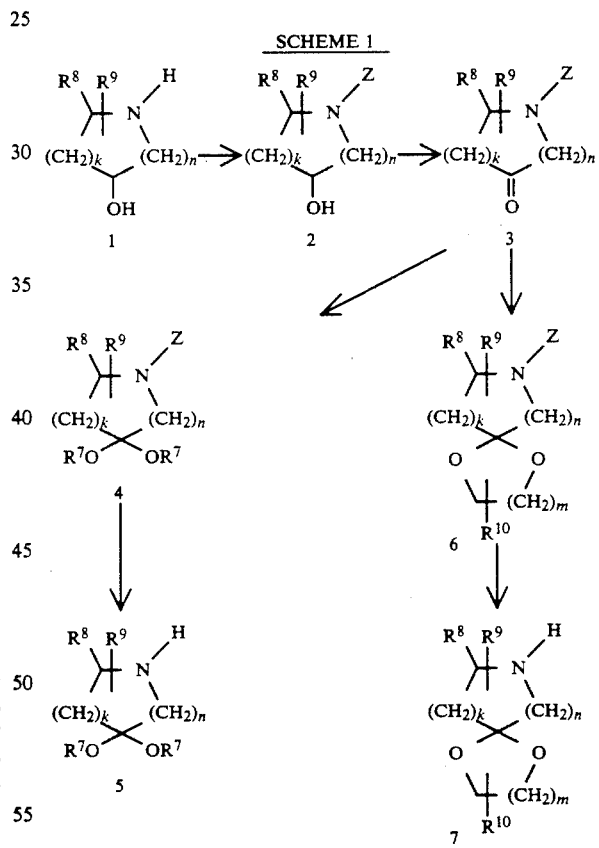

SCHEME 1

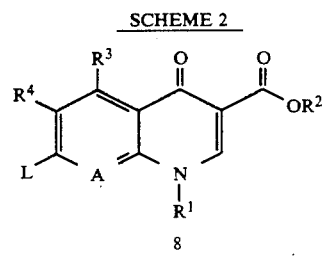

SCHEME 2

-continued
SCHEME 2

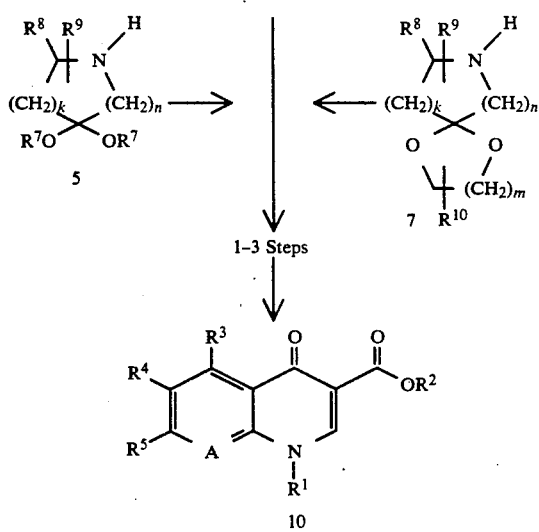

As is common in conventional organic synthesis, amino and hydroxy groups may be protected and deprotected as necessary. The protecting groups for amino groups which can be used include, for example, benzyloxycarbonyl, o-chlorobenzyloxycarbonyl, p-nitrobenzyloxycarbonyl, p-methoxybenzyloxycarbonyl, t-amyloxycarbonyl, isobornyloxycarbonyl, adamantyloxycarbonyl, 2-(4-biphenyl)-2-propyloxycarbonyl, 9-fluorenylmethoxycarbonyl, methylsulfonyloxycarbonyl, trifluoroacetyl, formyl, and 2,4-dinitrophenylsulfenyl. Examples of protecting groups for hydroxy groups include acetate, trichloroacetate, benzoate, methyl carbonate, t-butyldiphenylsilyl, t-butyldimethylsilyl and di-t-butylmethylsilyl, among others.

The condensation of amino groups (such as those present in certain of the compounds of this invention) with amino acids and peptides may be effected in accordance with convention condensation method, such as the azide method, the mixed anhydride method, the DCC (dicyclohexylcarbodiimide) method, the active ester method (p-nitrophenyl ester method, N-hydroxysuccinic acid ester imide method, cyanomethyl ester method and the like), the Woodward reagent K

SCHEME 3

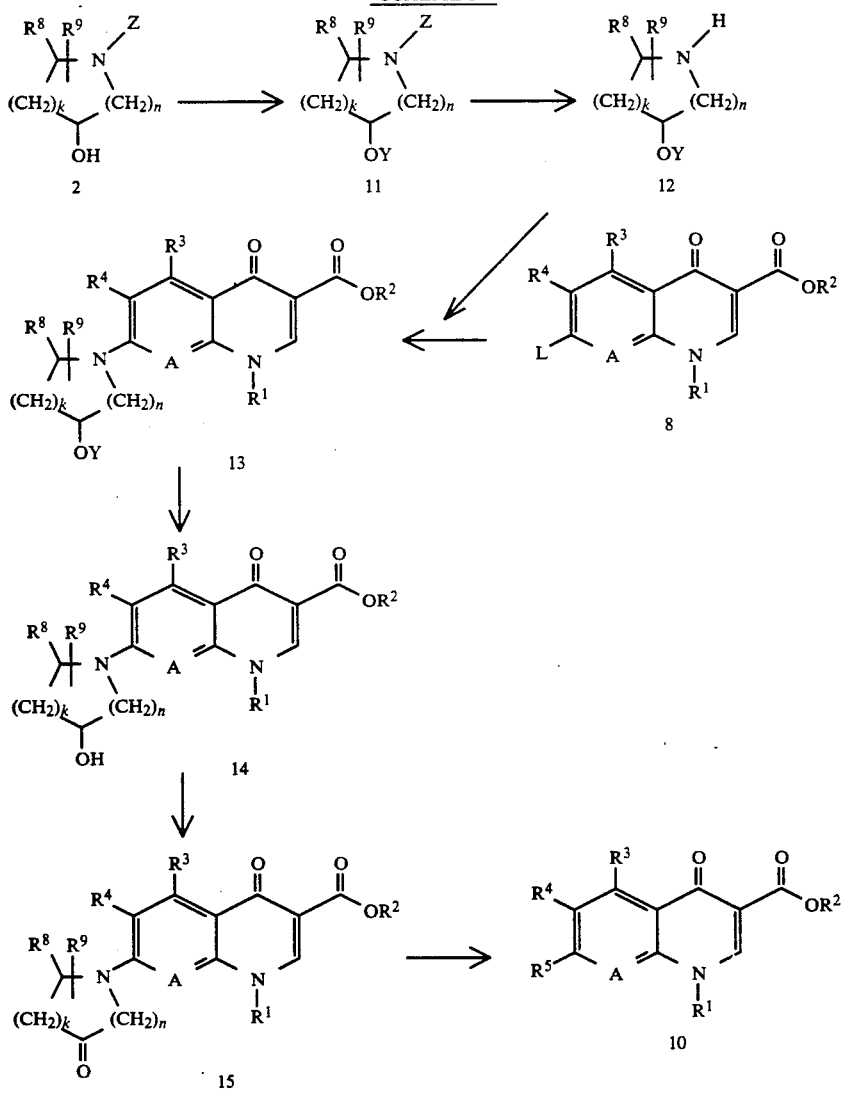

method, the DCC-HOBT (1-hydroxybenzotriazole) method and the like. Classical methods for amino acid condensation reactions are described in Peptide Synthesis" Second edition, by M. Bodansky, Y. S. Klausner and M. A. Ondetti (1976). It is contemplated that the amino acid coupling reaction could be carried out before or after the amino-containing group is incorporated into the compound by displacement of the 7-halo atom of the appropriate intermediate. Examples of amino acids which may be coupled, either alone or in combination, include naturally occurring amino acids, such as glycine, alanine, leucine, isoleucine, methionine, phenylalanine, valine and the like, as well as synthetic amino acids such as cyclohexylalanine, cyclohexylglycine, aminopentanoic acid and the like.

As in conventional peptide synthesis, branched chain amino and carboxyl groups at alpha and omega positions may be protected and deprotected as necessary. The protecting groups for amino acids which can be used involve, for example, benzyloxycarbonyl, t-butoxycarbonyl, trifluoroacetyl, formyl, diphenylphosphinothioyl, or similar compounds. The examples of protecting groups cor carboxyl groups involve, for example, benzyl ester, cyclohexyl ester, 4-nitrobenzyl ester and the like. Amino acids having functional groups other than amino or carboxyl, such as arginine, serine, cysteine and the like, may also be protected if necessary with suitable protecting groups. These protecting groups are well known to those skilled in the art.

In accordance with reaction Scheme 1 illustrated above, wherein $R^8$ and $R^9$ may independently be hydrogen, lower alkyl, or lower alkoxy(lower alkyl), the heterocyclic amine functional group of the compounds of Formula 1 is protected by reacting with a protecting group reagent, such as benzyloxycarbonyl chloride, or a similar reagent such as described above, to give the amino-protected compounds of Formula 2. The compounds of Formula 2 are converted to the ketones of Formula 3 by oxidation with a suitable oxidizing reagent, for example modified Swern reagents, such as sulfur trioxide/pyridine, Jones reagent, Corey's reagent, or other reagents generally known to those skilled in the art, in the presence of a solvent and under other conditions appropriate for that reaction. Compounds of Formula 3 may be converted into ketals of Formula 4 by reacting with the appropriate alcohol, such as methanol, trimethyl orthoformate, ethanol, propanol, or another straight or branched chain lower alcohol, in the presence of a strong organic acid, such as p-toluenesulfonic acid, pyridinium toluenesulfonate, camphor sulfonic acid, or the like. The protecting group can be removed from compounds of Formula 4 to give compounds of Formula 5 by any of several common procedures, such as hydrolysis, hydrogenation in the presence of a catalyst, reaction with mercury amalgam, photochemically, or by other appropriate methods known to those skilled in the art.

Compounds of Formula 3 are converted to the spiroketals of Formula 6 by reacting with an appropriate 1,2- or 1,3-diol, such as 1,2-ethanediol, 1,2-propanediol, 1,3-propanediol, 1,2,3-propanetriol, 3-bromo-1,2-propanediol or the like, by heating in an appropriate organic solvent in the presence of an appropriate acidic catalyst, such as mentioned above. The protecting group Z of compounds of Formula 6 is removed to give compounds of Formula 7, by an appropriate method as described above.

In the event that compounds of Formula 1 wherein $R^8$ and $R^9$ may independently be hydroxy(lower alkyl), an additional step is necessary to protect the hydroxyl groups before proceeding to compounds of Formula 2. This may be done with any suitable hydroxyl protecting group, such as acetate or a similar reagent as described above. The hydroxy-protected compounds of Formula 2 are converted to the compounds of Formula 3 by oxidation as described above. The ketal or spiro-ketal compounds of Formulae 4 or 6 are then formed as described above. These compounds in turn are converted to the compounds of Formulae 5 and 7, respectively, by removal, first of the hydroxy protecting groups, such as reaction with fluoride ion or hydrolysis with a strong base, such as sodium hydroxide, potassium, t-butoxide, sodium methoxide or the like, and then by removing the Z group as described above. In some instances only the Z groups may be removed and the hydroxy-protecting groups may be left on the compounds of Formulae 5 and 7, for removal at a later step.

In the case where compounds of Formula 1 have $R^8$ and $R^9$ groups such as amino, lower alkylamino, amino(lower alkyl) or substituted amino(lower alkyl), an additional step may be necessary to protect these amino groups with an appropriate protecting group, as discussed above, before proceeding to compounds of Formula 2 in the manner described above. These protecting groups may then be removed after the ketal formation in Scheme 1, either at the same time that the Z group is removed as described above, or in a different step. The separate removal may be accomplished by cleavage with mild acids that will not cleave the ketal, such as trifluoroacetic acid, or with weak bases, for example ammonia in methanol or sodium carbonate solution, among others. As an alternative to removal of the amino protecting groups at this step, compounds of Formulae 5 and 7 may be left with the protecting groups in the $R^8$ and $R^9$ groups for removal at a later step in Scheme 2.

In the case where compounds of Formula 1 have $R^8$, $R^9$ or $R^{10}$ groups such as amino acid-substituted amino or amino acid-substituted amino(lower alkyl), this amino acid function may be any naturally occurring amino acid or a short-chain peptide.

In the case where compounds of Formula 1 have $R^{10}$ selected from the group consisting of amino, lower alkylamino, amino(lower alkyl) or substituted amino(lower alkyl), if this amine function is present on the selected diol it must be protected before reaction to form the spiro-ketal. In the event that the amine group is protected before ketal formation, an appropriate amine protecting group such as described above may be used. This amine function may also be generated from an appropriately substituted spiro-ketal. This may be done by reacting an appropriate compound of Formula 6, where $R^{10}$ possesses an appropriate leaving group, such as a halogen atom, with compounds that produce an amino group directly or upon further reaction, for example compounds such as ammonia, loweralkyl amine or sodium azide, in a suitable solvent and in the presence of a base, such as sodium alkoxide, sodium hydroxide or excess amine. For example, reaction of a compound of Formula 6 where $R^{10}$ is bromoalkyl with an alkylamine produces a compound of Formula 6 where $R^{10}$ is alkylamino. Optionally, reaction of a compound of Formula 6 where $R^{10}$ is bromoalkyl with sodium azide produces an intermediate azide compound which is then reduced to produce a compound of Formula 6 where $R^{10}$ is aminoalkyl. In the case where $R^{10}$ contains a primary or secondary amine, it is generally necessary to protect the amino group by one of the means described above and retain the amino protecting group on compounds of Formula 7 before proceeding with subsequent reaction, as shown in Scheme 2.

In accordance with reaction Scheme 2, the compounds of Formula 8 are condensed with the compounds of Formula 5 or Formula 7, by heating, for example from 40° C. to 60° C., under anhydrous conditions and in the presence of an acid acceptor such as pyridine or triethylamine. In the event that $R^8$ or $R^9$ or $R^{10}$ possesses a protecting group, this group must be removed by one of the methods described above. In the event that compounds of Formula 10 where $R^2$ is H are desired, the hydrolysis of the ester must be performed, generally by heating a solution of the ester in a suitable solvent in the presence of a strong base, for example 1N NaOH in tetrahydrofuran from 40° C. to 80° C. for a period from 1 to 12 hours.

Reaction Scheme 3 is given as illustration of the breadth of procedures available to one skilled in the art to synthesize compounds of Formula 10. In accordance with reaction Scheme 3, compounds of Formula 2 (from Scheme 1) are protected at the hydroxy function with a hydroxy protecting group, such as trichloroacetate or dimethyl-t-butylsilyl, or another reagent as described previously, to give the hydroxy-protected compound of Formula 11. Compounds of Formula 11 may have the amino protecting group removed as described previously to give compounds of Formula 12. The compounds of Formula 12 are next condensed with compounds of Formula 8 (from Scheme 2) to give compounds of Formula 13. These compounds may have the hydroxy protecting groups removed as described previously to give compounds of Formula 14. These hydroxy compounds may in turn be reacted with an oxidizing agent as described in the narrative to Scheme 1 above to give the keto compounds of Formula 15. The keto compounds may then be converted into the ketals or spiroketals of Formula 10 by the steps described previously.

In the teachings above, it will be obvious to one skilled in the art that in compounds of Formula 6 and 7, when m=1, $R^{10}$ may not be NH₂ or OH, but when m=2, $R^{10}$ may be NH₂ or OH when on a carbon atom in the position beta to the ketal oxygen atoms.

The foregoing schemes may be understood better from the following examples, which are presented for the purpose of illustration only and are not intended to limit the scope of the invention.

EXAMPLE 1

7-(3,3-Dimethoxypyrrolidin-1-yl)-1-(2,4-difluorophenyl)-6-fluoro-1,4-dihydro-4-oxo-3-quinolinecarboxylic acid Step 1: 3-pyrrolidinol benzyl carbamate A solution of 3-pyrrolidinol (13.23 g, 0.15 mmol) (preparation described by M. M. Bowers Nemia, et al., Synth. Commun., 13(13), 1117-1123, 1983) in 182 mL of 1.0M NaOH was cooled to 0° C. in an ice bath. To this solution was added, dropwise with stirring over a half-hour period, 21.68 mL of benzylchloroformate (0.15 mmol), and the reaction mixture was stirred for 3 hours at 0° C. The solution was diluted with about 200 mL of water and extracted three times with methylene chloride. The extracts were combined, dried over anhydrous sodium sulfate, filtered, and the solvent was removed by evaporation to afford the title compound, MS M/Z: 222 (M+H); NMR (CDCl3) d 1.95 (m, 2H), 2.21 (dd, 1H, J=22.5 Hz, J=3.0 Hz), 3.51 (m, 4H), 4.45 (m, 1H), 5.14 (s, 2H), 7.37 (m, 5H).

Step 2: 3-pyrrolidinone benzyl carbamate

To a solution of 31.6 g (0.14 mmol) of 3-pyrrolidinol benzyl carbamate, from Step 1, in 275 mL of DMSO cooled to 0° C. was added 159.25 mL (1.12 mmol) of triethylamine. To this solution, maintained at 0° C. with stirring, was added dropwise over a one hour period a solution of 68.18 g (0.42 mmol) of sulfur trioxide pyridine complex in 250 mL of DMSO. The solution was stirred an additional half-hour at 0° C., then the ice bath was removed and the reaction allowed to proceed for 20 hours at room temperature. The DMSO solution was then poured into 1 L of 20% sodium chloride solution and the product was extracted with three washings of methylene chloride. The methylene chloride solution was washed with 20% NaCl solution to remove excess DMSO, dried over anhydrous sodium sulfate, filtered, and the solvent was removed by evaporation. The dark liquid residue was distilled in a kugelrohr apparatus (140°-160° C. @ 5 Torr) and further purified by chromatography on silica gel (solvent 0.5-2.0% methanol in chloroform) to afford the title compound, MS M/Z 220 (M+H); NMR: d 2.61 (t,2H, J=7.5 Hz), 3.82 (s, 2H), 3.85 (t, 2H, J=7.5 Hz), 5.18 (s, 2H), 7.37 (m, 5H).

Step 3: 3,3-dimethoxypyrrolidine benzyl carbamate

A solution of the compound from step 2 was prepared by dissolving 2.00 g (0.91 mmol) of 3-pyrrolidinone benzyl carbamate in 20 mL of methanol, then an excess (20 mL) of trimethyl orthoformate was added followed by 0.087 g (0.45 mmol) of p-toluenesulfonic acid, and the reaction solution heated at 60° C. for 3 hours. The reaction contents were poured into a 5% sodium bicarbonate solution, and the product was extracted (3×) into methylene chloride which was dried over sodium sulfate, filtered and evaporated to dryness. This compound was not purified further, but taken directly to the next step.

Step 4: 3,3-dimethoxypyrrolidine

The 2.21 g of 3,3-dimethoxy-pyrrolidine benzyl carbamate, from step 3, dissolved in 100 mL of methanol, 2.21 g of Pd/C (wet) was added, and placed under 4 atm of hydrogen for 20 hours. The catalyst was filtered off using a 0.45 micro millipore filter and the solvent was evaporated to afford the title compound.

Step 5: 7-(3,3-Dimethoxypyrrolidin-1-yl)-1-(2,4-difluorophenyl)-6-fluoro-1,4-dihydro-4-oxo-3-quinolinecarboxylic acid Into an oven-dried glass flask flushed with dry N₂, and containing 6 mL of dry pyridine were placed 0.116 g (0.88 mmol) of 3,3-dimethoxypyrrolidine, from Step 4, then 0.150 g (0.44 mmol) of 6,7-difluoro-1-(2,4-difluorophenyl)-1,4-dihydro-4-oxo-3-quinoline carboxylic acid (preparation described by H. Tone et al., *Eur. Pat. Appl.* EP 181521, May, 1986), and 180 mL (1.3 mmol) of triethylamine. This reaction solution was maintained under N₂ and heated to 45° C. for 41 hours. The pyridine was then removed by azeotropic distillation with toluene, the residue triturated with water, the pH adjusted to pH 5 to 6 with acetic acid, and the solution filtered. The solid was washed with hot ethanol:water (3:1), which was refiltered and dried to afford the title compound, mp 228°-230° C.; MS(DCl) M/Z: 449 (M+H), 404 (M-COOH); NMR d 2.13 (dd, 2H, J=7.5 Hz), 3.41 (dd, 2H, J=1.5 Hz, J=7.5 Hz), 3.62 (d, 2H, J=3.6 Hz), 3.27 (s, 6H), 5.87 (d, 1H, J=7.5 Hz), 7.30 (m, 2H), 7.65 (m, 1H), 7.95 (d, 1H, J=13.5 Hz), 8.60 (s, 1H). Analysis calculated for $C_{22}H_{19}F_3N_2O_5 \cdot 0.5\ H_2O$: C, 59.77; H, 4.41; N, 6.12. Found: C, 58.28; H, 4.34; N, 6.21.

EXAMPLES 2-12

By following the procedures described in Example 1 and replacing 6,7-difluoro-1-(2,4-difluorophenyl)-1,4-dihydro-4-oxo-3-quinolinecarboxylic acid (in Step 5) with the appropriate compound containing $R^1$, $R^3$, and A, below, Examples 2-12 may be prepared as disclosed in Table 1

TABLE 1

| Example # | $R^1$ | $R^3$ | A |
|---|---|---|---|
| 2 | —C2H5 | H | CH |
| 3 | —C2H4—F | H | CH |
| 4 | —NH—CH3 | H | CH |
| 5 | -cyclopropyl | F | CH |
| 6 | -cyclopropyl | NH2 | CH |
| 7 | -cyclopropyl | H | C—CH3 |
| 8 | -cyclopropyl | H | C—Cl |
| 9 | -cyclopropyl | CH3 | CH |
| 10 | -t-butyl | H | CH |
| 11 | 3-methyl-1-butyn-3-yl | H | CH |
| 12 | bicyclo[1.1.1]pent-1-yl | H | CH |

EXAMPLE 13

1-Cyclopropyl-7-(3,3-dimethoxypyrrolidin-1-yl)-6-fluoro-1,4-dihydro-4-oxo-3-quinolinecarboxylic acid Following procedures similar to Step 5 of Example 1, a 0.186 g (1.4 mmol) sample of 3,3-dimethoxypyrrolidine, from Step 4 of Example 1, was reacted with 0.200 g (0.7 mmol) of 7-chloro-1-cyclopropyl-6-fluoro-1,4-dihydro-4-oxo-3-quinolinecarboxylic acid (preparation described by K. Grohe, et al., DE 3142854, May, 1983) at 60° C. under $N_2$ for 188 hours to yield the title compound, mp 224°-226° C.: MS (DCl) M/Z 377 (M+H); NMR d 1.42 (d, 1H), 1.63 (m, 2H), 3.75 (s, 3H), 3.99 (s, 3H), 4.02 (m, 1H), 4.26 (m, 2H), 4.40 (m, 2H), 7.46 (d, 1H, J=7.5 Hz), 8.13 (d, 1H, J=13.5 Hz), 9.19 (s, 1H). Analysis calculated for $C_{19}H_{21}FN_2O_5 \cdot 0.5\ H_2O$: C, 59.21; H, 5.75; N, 7.27. Found: C, 59.70; H, 5.48; N, 7.13.

EXAMPLE 14

1-(2,4-difluorophenyl)-7-(1,5-dioxa-8-azaspiro[5.4]dec-8-yl)-6-fluoro-1,4-dihydro-4-oxo-3-quinolinecarboxylic acid Step 1: 1,5-dioxa-8-azaspiro[5.4]decane benzyl carbamate Into a round bottom flask were placed 2.00 g (9.1 mmol) of 3-pyrrolidinone benzyl carbamate, from Example 1 Step 2, dissolved in 40 mL of toluene, 1.65 mL (22.8 mmol) of 1,3-propanediol and 0.09 g (0.46 mmol) of p-toluenesulfonic acid. The mixture was heated at 110°-125° C. for 48 hours. The solution was poured into 100 mL of 5% sodium bicarbonate solution, and the product was extracted into ethyl acetate, which was then dried over anhydrous sodium sulfate. The solvent was removed under vacuum, and the residue distilled in a kugelrohr apparatus (200° C. @ 2.5 Torr) to afford the title compound, MS: M/Z 295 (M+NH4), which was taken directly to the next step.

Step 2: 1,5-dioxa-8-azaspiro[5.4]decane

The protecting group was removed by dissolving 2.09 g (7.5 mmol) of 1,5-dioxa-8-azaspiro[5.4]decane benzyl carbamate, from Step 1, in 100 mL of methanol, adding 0.50 g of 20% Pd/C, and hydrogenating at room temperature under 4 atm of hydrogen for 24 hours. The catalyst was removed by filtration, then the solvent was removed under vacuum to afford the title compound, MS: M/Z 144 (M+H), which was taken directly to the next step.

Step 3: 1-(2,4-difluorophenyl)-7-(1,5-dioxa-8-azaspiro[5.4]dec-8-yl)-6-fluoro-1,4-dihydro-4-oxo-3-quinolinecarboxylic acid ethyl ester Into oven-dried glassware under a $N_2$ atmosphere were placed 0.176 g (1.23 mmol) of 1,5-dioxa-8-azaspiro[5.4]decane, from Step 2, then 0.300 g (0.82 mmol) of 1-(2,4-difluorophenyl)-6,7-difluoro-1,4-dihydro-4-oxo-3-quinolinecarboxylic acid ethyl ester (preparation described by H. Narita, et al., Yakugaku Zasshi, 106(9), 795-801, 1986; CA106:196218) dissolved in 10 mL of pyridine, and 0.46 mL (3.28 mmol) of triethylamine. The solution was then heated at 45° C. for 24 hours. The solvent was removed by evaporation to afford the title product which was purified by column chromatography over silica gel (0.5% methanol/chloroform increasing to 2.0% methanol/chloroform). The ester was not further purified, but was taken directly to the next step.

Step 4: 1-(2,4-difluorophenyl)-7-(1,5-dioxa-8-azaspiro[5.4]dec-8-yl)-6-fluoro-1,4-dihydro-4-oxo-3-quinolinecarboxylic acid The 1-(2,4-difluorophenyl)-7-(1,5-dioxa-8-azaspiro[5.4]decan-yl)-6-fluoro-1,4-dihydro-4-oxo-3-quinolinecarboxylic acid ethyl ester from Step 4 was dissolved in 5 mL of THF, to which was added 8 mL of 1M NaOH, and the mixture was heated under reflux at 50° C. for 6 hours, then at 85° C. for 2 hours without the condenser to remove the THF. The solution was poured into water, the pH adjusted to 4, and the product filtered off, washed with water and dried to afford 0.143 g of the title compound, mp 168°-170° C.; MS (DCl) M/Z 461 (M+H); NMR: d 2.29 (dd,2 H, J=6.0), 3.47 (dd, 2H, J=6.0 Hz), 3.69 (d, 2H, J=3.6 Hz), 3.97 (m, 6H), 5.87 (d, 1H, J=7.5 Hz), 7.28 (m, 2H), 7.62 (m, 1H), 7.97 (d, 1H, J=13.5 Hz), 8.62 (s, 1H). Analysis calculated for $C_{23}H_{19}F_3N_2O_5 \cdot H_2O$: C, 57.74; H, 4.42; N, 5.86. Found: C, 58.19; H, 4.29; N, 5.78.

EXAMPLES 15-25

By following the procedures described in Example 14 and replacing 1-(2,4-difluorophenyl)-6,7-difluoro-1,4-dihydro-4-oxo-3-quinolinecarboxylic acid ethyl ester with the appropriate compound containing $R^1$, $R^3$, and A, below, Examples 15-25 may be prepared as disclosed in Table 2.

TABLE 2

| Example # | $R^1$ | $R^3$ | A |
|---|---|---|---|
| 15 | —C2H5 | H | CH |

TABLE 2-continued

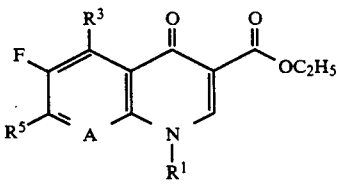

| Example # | R¹ | R³ | A |
|---|---|---|---|
| 16 | —C2H4—F | H | CH |
| 17 | —NH—CH3 | H | CH |
| 18 | -cyclopropyl | F | CH |
| 19 | -cyclopropyl | NH2 | CH |
| 20 | -cyclopropyl | H | C—CH3 |
| 21 | -cyclopropyl | H | C—Cl |
| 22 | -cyclopropyl | CH3 | CH |
| 23 | -t-butyl | H | CH |
| 24 | 3-methyl-1-butyn-3-yl | H | CH |
| 25 | bicyclo[1.1.1]pent-1-y | H | CH |

EXAMPLES 26–79

By following the procedures described in Example 14 and replacing 1,5-dioxa-8-azaspiro[5.4]decane (in Step 3) with the appropriate ketal compound, Examples 26–79 (in which A=CH and R¹=2,4-difluorophenyl) may be prepared as disclosed in Table 3.

TABLE 3

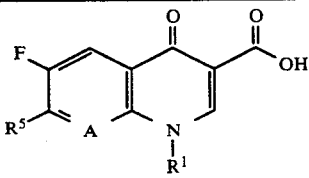

| Example # | Ketal compound from which R⁵ is derived: |
|---|---|
| *26 | 2-aminomethyl-3,3-dimethoxypyrrolidine |
| *27 | 6-aminomethyl-1,4-dioxa-7-azaspiro[4.4]nonane |
| *28 | 8-aminomethyl-2-ethyl-1,4-dioxa-7-azaspiro[4.4]nonane |
| 29 | 9-chloro-1,4-dioxa-7-azaspiro[4.4]nonane |
| 30 | 2,3-dimethyl-1,4-dioxa-7-azaspiro[4.4]nonane |
| 31 | 6,9-dimethyl-1,4-dioxa-7-azaspiro[4.4]nonane |
| 32 | 8,9-dimethyl-1,4-dioxa-7-azaspiro[4.4]nonane |
| 33 | 6-fluoro-1,4-dioxa-7-azaspiro[4.4]nonane |
| 34 | 9-fluoromethyl-1,4-dioxa-7-azaspiro[4.4]nonane |
| 35 | 2-ethyl-8-(N-phenylalanyl)-1,4-dioxa-7-azaspiro[4.4]nonane |
| 36 | 2-ethyl-8-(N-valylaminomethyl)-1,4-dioxa-7-azaspiro[4.4]nonane |
| 37 | 9-(N-isoleucyl-valylaminomethyl)-1,4-dioxa-7-azaspiro[4.4]nonane |
| 38 | 9-(N-alanyl-norvalylaminomethyl)-1,4-dioxa-7-azaspiro[4.4]nonane |
| 39 | 9-(N-valyl-tyrosylaminomethyl)-1,4-dioxa-7-azaspiro[4.4]nonane |
| *40 | 10-amino-1,5-dioxa-8-azaspiro[5.4]decane |
| *41 | 4-aminomethyl-1,5-dioxa-8-azaspiro[5.4]decane |
| *42 | 10-aminomethyl-1,5-dioxa-8-azaspiro[5.4]decane |
| *43 | 3-amino-4-methyl-1,5-dioxa-8-azaspiro[5.4]decane |
| 44 | 3-chloro-1,5-dioxa-8-azaspiro[5.4]decane |
| 45 | 4-ethyl-1,5-dioxa-8-azaspiro[5.4]decane |
| 46 | 10-fluoromethyl-1,5-dioxa-8-azaspiro[5.4]decane |
| 47 | 10-methyl-1,5-dioxa-8-azaspiro[5.4]decane |
| 48 | 3-N-(valylamino)-1,5-dioxa-8-azaspiro[5.4]decane |
| 49 | 4-N-(isoleucyl-alanylaminomethyl)-1,5-dioxa-8-azaspiro[5.4]decane |
| *50 | 6-amino-1,4-dioxa-8-azaspiro[4.5]decane |
| *51 | 6-aminomethyl-1,4-dioxa-8-azaspiro[4.5]decane |
| *52 | 3-aminomethyl-6-methyl-1,4-dioxa-8-azaspiro[4.5]decane |
| 53 | 2,6-dimethyl-1,4-dioxa-8-azaspiro[4.5]decane |
| 54 | 3-N,N-dimethylaminomethyl-1,4-dioxa-8-azaspiro[4.5]decane |
| 55 | 3-ethyl-1,4-dioxa-8-azaspiro[4.5]decane |

TABLE 3-continued

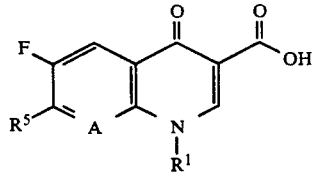

| Example # | Ketal compound from which R⁵ is derived: |
|---|---|
| 56 | 6-fluoromethyl-1,4-dioxa-8-azaspiro[4.5]decane |
| 57 | 6-methyl-1,4-dioxa-8-azaspiro[4.5]decane |
| 58 | 3-(N-valylaminomethyl)-1,4-dioxa-8-azaspiro[4.5]decane |
| 59 | 3-(N-leucyl-isoleucylaminomethyl)-1,4-dioxa-8-azaspiro[4.5]decane |
| *60 | 7-amino-1,5-dioxa-9-azaspiro[5.5]undecane |
| *61 | 2-aminomethyl-1,5-dioxa-9-azaspiro[5.5]undecane |
| *62 | 3-aminomethyl-1,5-dioxa-9-azaspiro[5.5]undecane |
| *63 | 8-aminomethyl-1,5-dioxa-9-azaspiro[5.5]undecane |
| 64 | 2-ethyl-7-methyl-1,5-dioxa-9-azaspiro[5.5]undecane |
| 65 | 2-methyl-1,5-dioxa-9-azaspiro[5.5]undecane |
| 66 | 7-methyl-1,5-dioxa-9-azaspiro[5.5]undecane |
| 67 | 3-(N-leucylamino)-1,5-dioxa-9-azaspiro[5.5]undecane |
| 68 | 2-(N-isoleucylaminomethyl)-1,5-dioxa-9-azaspiro[5.5]undecane |
| 69 | 3-(N-alanyl-tyrosylamino)-1,5-dioxa-9-azaspiro[5.5]undecane |
| *70 | 3-amino-1,5-dioxa-8-azaspiro[5.5]undecane |
| *71 | 10-amino-1,5-dioxa-8-azaspiro[5.5]undecane |
| *72 | 2-aminomethyl-1,5-dioxa-8-azaspiro[5.5]undecane |
| *73 | 10-aminomethyl-1,5-dioxa-8-azaspiro[5.5]undecane |
| *74 | 11-aminomethyl-1,5-dioxa-8-azaspiro[5.5]undecane |
| 75 | 10-methyl-1,5-dioxa-8-azaspiro[5.5]undecane |
| 76 | 11-methyl-1,5-dioxa-8-azaspiro[5.5]undecane |
| 77 | 3-(N-valylamino)-1,5-dioxa-8-azaspiro[5.5]undecane |
| 78 | 10-(N-valylamino)-1,5-dioxa-8-azaspiro[5.5]undecane |
| 79 | 3-(N-isoleucyl-valylamino)-1,5-dioxa-8-azaspiro[5.5]undecane |

*Non-ring amino groups are protected and deprotected as in Example 159.

EXAMPLE 80

1-Cyclopropyl-6,8-difluoro-7-(1,5-dioxa-8-azaspiro[5.4]dec-8-yl)-1,4-dihydro-4-oxo-3-quinolinecarboxylic acid Step 1. 1-Cyclopropyl-6,8-difluoro-7-(1,5-dioxa-8-azaspiro[5.4]dec-8-yl)-1,4-dihydro-4-oxo-3-quinolinecarboxylic acid ethyl ester A 0.276 g (1.8 mmol) sample of 1,5-dioxa-8-azaspiro[5.4]decane, from Step 2 Example 14, 0.400 g (1.29 mmol) of 1-cyclopropyl-6,7,8-trifluoro-1,4-dihydro-4-oxo-3-quinolinecarboxylic acid ethyl ester (preparation described by K. Grohe, et al., DE 3318145, November 1984) and 0.52 mL (3.7 mmol) of triethylamine and 12 mL of pyridine were heated at 65° C. for 48 hours in dry glassware and under dry nitrogen. The solvent was evaporated and the ester purified by chromatography on a silica gel column using as eluant 0.5% methanol in methylene chloride increasing to 2% methanol in methylene chloride. The solvent was removed to afford 0.218 g of the title compound, which was taken to the next step directly.

Step 2: 1-Cyclopropyl-6,8-difluoro-7-(1,5-dioxa-8-azaspiro[5.4]dec-8-yl)-1,4-dihydro-4-oxo-3-quinolinecarboxylic acid The ester from Step 1 was hydrolyzed via a procedure similar to that of Step 4 Example 14 to afford 0.137 g of the title compound, mp 226°–227° C.; MS M/Z 407 (M+H); NMR: d 1.47 (m, 4H), 2.21 (dq, 2H, J=6.0 Hz, J=30.0 Hz), 2.87 (m, 1H), 4.30 (dt, 2H, J=6.0 Hz, J=7.5 Hz), 4.53 (dt, 2H, J=6.0 Hz, J=6.0 Hz), 4.42 (m, 6H), 8.05 (dd, 1H, J=13.5 Hz, J=1.5 Hz), 9.25 (s, 1H). Analysis calculated for $C_{20}H_{20}F_2N_2O_5$: C, 59.11; H, 4.96; N, 6.89. Found: C, 58.60; H, 5.01; N, 6.73.

EXAMPLES 81-134

By following the procedures described in Example 80 and replacing 1,5-dioxa-8-azaspiro[5.4]decane (in Step 1) with the appropriate ketal compound, Examples 81-134 (in which A=CF and $R^1$=cyclopropyl) are prepared as disclosed in Table 4.

TABLE 4

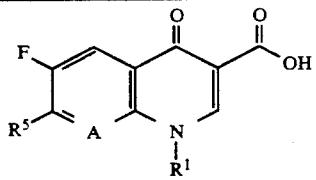

| Example # | Ketal compound from which $R^5$ is derived: |
|---|---|
| *81 | 2-aminomethyl-3,3-dimethoxypyrrolidine |
| *82 | 6-aminomethyl-1,4-dioxa-7-azaspiro[4.4]nonane |
| *83 | 8-aminomethyl-2-ethyl-1,4-dioxa-7-azaspiro[4.4]nonane |
| 84 | 9-chloro-1,4-dioxa-7-azaspiro[4.4]nonane |
| 85 | 2,3-dimethyl-1,4-dioxa-7-azaspiro[4.4]nonane |
| 86 | 6,9-dimethyl-1,4-dioxa-7-azaspiro[4.4]nonane |
| 87 | 8,9-dimethyl-1,4-dioxa-7-azaspiro[4.4]nonane |
| 88 | 6-fluoro-1,4-dioxa-7-azaspiro[4.4]nonane |
| 89 | 9-fluoromethyl-1,4-dioxa-7-azaspiro[4.4]nonane |
| 90 | 2-ethyl-8-(N-phenylalanyl)-1,4-dioxa-7-azaspiro[4.4]-nonane |
| 91 | 2-ethyl-8-(N-valylaminomethyl)-1,4-dioxa-7-azaspiro[4.4]-nonane |
| 92 | 9-(N-isoleucyl-valylaminomethyl)-1,4-dioxa-7-azaspiro-[4.4]nonane |
| 93 | 9-(N-alanyl-norvalylaminomethyl)-1,4-dioxa-7-azaspiro-[4.4]nonane |
| 94 | 9-(N-valyl-tyrosylaminomethyl)-1,4-dioxa-7-azaspiro[4.4]-nonane |
| *95 | 10-amino-1,5-dioxa-8-azaspiro[5.4]decane |
| *96 | 4-aminomethyl-1,5-dioxa-8-azaspiro[5.4]decane |
| *97 | 10-aminomethyl-1,5-dioxa-8-azaspiro[5.4]decane |
| *98 | 3-amino-4-methyl-1,5-dioxa-8-azaspiro[5.4]decane |
| 99 | 3-chloro-1,5-dioxa-8-azaspiro[5.4]decane |
| 100 | 4-ethyl-1,5-dioxa-8-azaspiro[5.4]decane |
| 101 | 10-fluoromethyl-1,5-dioxa-8-azaspiro[5.4]decane |
| 102 | 10-methyl-1,5-dioxa-8-azaspiro[5.4]decane |
| 103 | 3-N-(valylamino)-1,5-dioxa-8-azaspiro[5.4]decane |
| 104 | 4-N-(isoleucyl-alanylaminomethyl)-1,5-dioxa-8-azaspiro-[5.4]decane |
| *105 | 6-amino-1,4-dioxa-8-azaspiro[4.5]decane |
| *106 | 6-aminomethyl-1,4-dioxa-8-azaspiro[4.5]decane |
| *107 | 3-aminomethyl-6-methyl-1,4-dioxa-8-azaspiro[4.5]decane |
| 108 | 2,6-dimethyl-1,4-dioxa-8-azaspiro[4.5]decane |
| 109 | 3-N,N-dimethylaminomethyl-1,4-dioxa-8-azaspiro[4.5]-decane |
| 110 | 3-ethyl-1,4-dioxa-8-azaspiro[4.5]decane |
| 111 | 6-fluoromethyl-1,4-dioxa-8-azaspiro[4.5]decane |
| 112 | 6-methyl-1,4-dioxa-8-azaspiro[4.5]decane |
| 113 | 3-(N-valylaminomethyl)-1,4-dioxa-8-azaspiro[4.5]decane |
| 114 | 3-(N-leucyl-isoleucylaminomethyl)-1,4-dioxa-8-azaspiro-[4.5]decane |
| *115 | 7-amino-1,5-dioxa-9-azaspiro[5.5]undecane |
| *116 | 2-aminomethyl-1,5-dioxa-9-azaspiro[5.5]undecane |
| *117 | 3-aminomethyl-1,5-dioxa-9-azaspiro[5.5]undecane |
| *118 | 8-aminomethyl-1,5-dioxa-9-azaspiro[5.5]undecane |
| 119 | 2-ethyl-7-methyl-1,5-dioxa-9-azaspiro[5.5]undecane |
| 120 | 2-methyl-1,5-dioxa-9-azaspiro[5.5]undecane |
| 121 | 7-methyl-1,5-dioxa-9-azaspiro[5.5]undecane |
| 122 | 3-(N-leucylamino)-1,5-dioxa-9-azaspiro[5.5]undecane |
| 123 | 2-(N-isoleucylaminomethyl)-1,5-dioxa-9-azaspiro[5.5]-undecane |
| 124 | 3-(N-alanyl-tyrosylamino)-1,5-dioxa-9-azaspiro[5.5]-undecane |
| *125 | 3-amino-1,5-dioxa-8-azaspiro[5.5]undecane |
| *126 | 10-amino-1,5-dioxa-8-azaspiro[5.5]undecane |
| *127 | 2-aminomethyl-1,5-dioxa-8-azaspiro[5.5]undecane |
| *128 | 10-aminomethyl-1,5-dioxa-8-azaspiro[5.5]undecane |

TABLE 4-continued

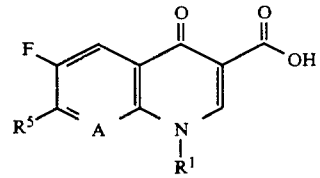

| Example # | Ketal compound from which $R^5$ is derived: |
|---|---|
| *129 | 11-aminomethyl-1,5-dioxa-8-azaspiro[5.5]undecane |
| 130 | 10-methyl-1,5-dioxa-8-azaspiro[5.5]undecane |
| 131 | 11-methyl-1,5-dioxa-8-azaspiro[5.5]undecane |
| 132 | 3-(N-valylamino)-1,5-dioxa-8-azaspiro[5.5]undecane |
| 133 | 10-(N-valylamino)-1,5-dioxa-8-azaspiro[5.5]undecane |
| 134 | 3-(N-isoleucyl-valylamino)-1,5-dioxa-8-azaspiro[5.5]-undecane |

*Non-ring amino groups are protected and deprotected as in Example 159.

EXAMPLE 135

1-(2,4-difluorophenyl)-7-(1,4-dioxa-2-methyl-7-azaspiro[4.4]non-7-yl)-6-fluoro-1,4-dihydro-4-oxo-3-quinolinecarboxylic acid Step 1: 1,4-dioxa-2-methyl-7-azaspiro[4.4]nonane benzyl carbamate Into an oven-dried system under positive nitrogen atmosphere and with a Dean-Stark trap were placed 4.38 g (20 mmol) of 3-pyrrolidinone benzyl carbamate, from Step 2 Example 1, 3.67 mL (50 mmol) of 1,2-propanediol, 0.190 g (1 mmol) of p-toluenesulfonic acid, and 65 mL of methylcyclohexane. The reactants were heated for 24 hours at 135° C. with stirring and azeotropic removal of water. The mixture was diluted with 100 mL of ethyl acetate, washed with 2×100 mL amounts of 5% sodium bicarbonate solution and once with water, then dried over anhydrous sodium sulfate. After filtration, the solvent was removed with a rotary evaporator to afford 4.85 g of the title compound. MS (DCl/NH$_3$) M/Z 295 (M+NH$_4$), 278 (M+H); NMR:(CDCl$_3$) d 1.28 (m, 1H), 1.30 (d, 3H, J=6.0 Hz), 2.05 (m, 2H, J=7.5 Hz), 3.50 (m, 4H), 4.03 (m, 1H), 4.20 (m, 1H), 5.12 (s, 2H), 7.41 (m, 5H). Analysis calculated for $C_{15}H_{19}F_3NO_4$: C, 64.97; H, 6.90; N, 5.05. Found: C, 65.10; H, 6.81; N, 4.87.

Step 2: 1,4-dioxa-2-methyl-7-azaspiro[4.4]nonane

The protecting group was removed by dissolving 2.52 g (9.08 mmol) of 1,4-dioxa-2-methyl-7-azaspiro[4.4-]nonane benzyl carbamate, from Step 1, in 200 mL of methanol, adding 1.25 g of 10% Pd/C, and hydrogenating at room temperature under 4 atm of hydrogen for 24 hours. The catalyst was removed by filtration, then the solvent was removed under vacuum to afford the title compound, which was taken directly to the next step.

Step 3. 1-(2,4-difluorophenyl)-7-(1,4-dioxa-2-methyl-7-azaspiro[4.4]non-7-yl)-6-fluoro-1,4-dihydro-4-oxo-3-quinolinecarboxylic acid ethyl ester In a reaction similar to that of Step 3 Example 14, into oven-dried glassware were placed 0.365 g (3 mmol) of 1,4-dioxa-2-methyl-7-azaspiro[4.4]nonane, from Step 2, then 0.365 g (1.0 mmol) of 1-(2,4-difluorophenyl)-6,7-difluoro-1,4-dihydro-4-oxo-3-quinolinecarboxylic acid ethyl ester (preparation described by H. Narita, et al., Yakugaku Zasshi, 106(9), 795-801, 1986; CA106:196218) dissolved in 9 mL of pyridine. The solution was heated at 45° C. for 96 hours under a nitrogen atmosphere. The solvent was removed on a rotary evaporator. The compound was dissolved in 50 mL of methylene chloride, washed with 2×50 mL of water and dried over anhydrous sodium sulfate. The solvent was removed by evaporation to afford the title product which was purified by recrystallization from ethanol/water to yield after drying 0.460 g of an off-white solid. The ester was taken directly to the next step.

Step 4. 1-(2,4-difluorophenyl)-7-(1,4-dioxa-2-methyl-7-azaspiro[4.4]non-7-yl)-6-fluoro-1,4-dihydro-4-oxo-3-quinolinecarboxylic acid The ester from Step 3 (0.460 g, 0.94 mmol) was dissolved in 5 mL of THF, to which was added 4 mL of 1M NaOH, and the mixture was heated under reflux conditions for 2.5 hours, cooled to room temperature, diluted with 20 mL of water and adjusted to pH 4-5 with glacial acetic acid. The resulting precipitate was isolated by suction filtration, washed with 2×10 mL of water, suspended in 7 mL of ethanol and heated under reflux with stirring for 1 hours. The product was again isolated by suction filtration, washed with 2×3 mL of ethanol and dried under vacuum at room temperature to afford 0.241 g of the title compound, mp 221°-222° C; MS (FAB) M/Z 461 (M+H), 417 (M—CO$_2$); NMR: (CDCl$_3$) d 1.30 (d, 3H, J=6 Hz), 2.10 (m, 2H), 3.45 (m, 3H), 3.57 (dd, 2H, J=4.5 Hz, J=18 Hz), 4.08 (m, 1H), 4.23 (m, 1H), 5.77 (d, 1H, J=7.5 Hz), 7.17 (m, 2H), 7.48 (m, 1H), 8.00 (dd, 1H, J=1.5 Hz, J=14 Hz), 8.17 (m, 2H), 15.10 (s, 1H). Analysis calculated for C$_{23}$H$_{19}$F$_3$N$_2$O$_5$: C, 60.00; H, 4.16; N, 6.08. Found: C, 60.63; H, 4.24; N, 6.13.

EXAMPLES 136-146

By following the procedures described in Example 135 and replacing 1-(2,4-difluorophenyl)-6,7-difluoro-1,4-dihydro-4-oxo-3-quinolinecarboxylic acid ethyl ester with the appropriate compound containing R$^1$,R$^3$, and A, below, Examples 136-146 may be prepared as disclosed in Table 5.

TABLE 5

| Example # | R$^1$ | R$^3$ | A |
|---|---|---|---|
| 136 | —C2H5 | H | CH |
| 137 | —C2H4—F | H | CH |
| 138 | —NH—CH3 | H | CH |
| 139 | -cyclopropyl | F | CH |
| 140 | -cyclopropyl | NH2 | CH |
| 141 | -cyclopropyl | H | C—CH3 |
| 142 | -cyclopropyl | H | C—Cl |
| 143 | -cyclopropyl | CH3 | CH |
| 144 | -t-butyl | H | CH |
| 145 | 3-methyl-1-butyn-3-yl | H | CH |
| 146 | bicyclo[1.1.1]pent-1-y | H | CH |

EXAMPLE 147

1-(2,4-difluorophenyl)-7-(1,4-dioxa-2-hydroxymethyl-7-azaspiro[4.4]non-7-yl)-6-fluoro-1,4-dihydro-4-oxo-3-quinolinecarboxylic acid Step 1: 1,4-dioxa-2-hydroxymethyl-7-azaspiro[4.4]nonane benzyl carbamate Via the procedure of Step 1 Example 135 were reacted at 150° C. for 24 hours 2.19 g (10 mmol) of 3-pyrrolidinone benzyl carbamate (from Step 2 Example 1), 1.46 mL (20 mmol) of glycerol, 15 mg (0.08 mmol) of p-toluenesulfonic acid, and 25 mL of toluene. The mixture was diluted with 100 mL of ethyl acetate, washed with 1×100 mL amounts of 10% sodium bicarbonate solution and once with water, then dried over anhydrous sodium sulfate. After filtration, the solvent was removed with a rotary evaporator. The crude product was purified by column chromatography on silica gel using 2% methanol/methylene chloride as eluant. Like fractions were combined and evaporated to dryness to afford 1.82 g of the title compound as a clear oil. Analysis calculated for C$_{15}$H$_{19}$NO$_5$: C, 61.42; H, 6.53; N, 4.78. Found: C, 61.12; H, 6.41; N, 4.69.

Step 2: 1,4-dioxa-2-hydroxymethyl-7-azaspiro[4.4]nonane

A 0.44 g (1.5 mmol) sample of the carbamate from Step 1 was hydrolyzed via the procedure of Step 2 Example 135 to afford 0.238 g of the title compound, MS (DCl/NH$_3$) M/Z 160 (M+H), 174 (M+NH$_4$), which was taken to the next step without further purification.

Step 3. 1-(2,4-difluorophenyl)-7-(1,4-dioxa-2-hydroxymethyl-7-azaspiro[4.4]non-7-yl)-6-fluoro-1,4-dihydro-4-oxo-3-quinolinecarboxylic acid ethyl ester Following the procedure of Step 3 Example 135, substituting 1,4-dioxa-2-hydroxymethyl-7-azaspiro[4.4]nonane for the spiro compound of that example, the title compound was prepared. Further purification by column chromatography on 70-230 mesh silica gel eluting stepwise with 3% and 5% methanol in methylene chloride, followed by removal of the solvent, afforded the pure title compound, mp 104°-106° C.; MS (FAB) M/Z 505 (M+H), 459 (M—CO$_2$).

Analysis calculated for C$_{25}$H$_{23}$F$_3$N$_2$O$_6$: C, 59.52; H, 4.60; N, 5.55. Found: C, 59.05; H, 4.58; N,. 5.48.

Step 4. 1-(2,4-difluorophenyl)-7-(1,4-dioxa-2-hydroxymethyl-7-azaspiro[4.4]non-7-yl)-6-fluoro-1,4-dihydro-4-oxo-3-quinolinecarboxylic acid A 0.707 g (1.4 mmol) sample of the ethyl ester from Step 3 was hydrolyzed via the procedure of Step 3 Example 135, except for removing the THF by distillation before dilution with water and subsequent workup. The title compound was afforded as 0.354 g of an off-white solid, mp 235°-237° C.; MS (DCl/NH$_3$) M/Z: 477 (M+H), 432 (M—CO$_2$); NMR: (DMSO-d$_6$) d 2.05 (m, 2H), 3.50-3.90 (m, 6H), 4.15 (m, 2H), 4.25 (m, 1H), 5.80 (d, 1H, J=7.5 Hz), 7.15 (m, 2H), 7.50 (m, 1H), 8.10 (d, 1H, J=13 Hz), 8.52 (s, 1H).

EXAMPLES 148-158

By following the procedures described in Example 147 and replacing 1-(2,4-difluorophenyl)-6,7-difluoro-1,4-dihydro-4-oxo-3-quinolinecarboxylic acid ethyl ester with the appropriate compound containing R$^1$,R$^3$, and A, below, Examples 148-158 are prepared as disclosed in Table 6.

TABLE 6

[Structure: quinolone core with R³ at position 3 on fused ring, F at position 6, R⁵ at position 5, A as ring atom, N-R¹, and -C(O)-C(O)OC₂H₅ substituent]

| Example # | R¹ | R³ | A |
|---|---|---|---|
| 148 | —C2H5 | H | CH |
| 149 | —C2H4—F | H | CH |
| 150 | —NH—CH3 | H | CH |
| 151 | -cyclopropyl | F | CH |
| 152 | -cyclopropyl | NH2 | CH |
| 153 | -cyclopropyl | H | C—CH3 |
| 154 | -cyclopropyl | H | C—Cl |
| 155 | -cyclopropyl | CH3 | CH |
| 156 | -t-butyl | H | CH |
| 157 | 3-methyl-1-butyn-3-yl | H | CH |
| 158 | bicyclo[1.1.1]pent-1-yl | H | CH |

EXAMPLE 159

1-(2,4-difluorophenyl)-7-(2-aminomethyl-1,4-dioxa-7-azaspiro[4.4]non-7-yl)-6-fluoro-1,4-dihydro-4-oxo-3-quinolinecarboxylic acid dihydrochloride Step 1: 2-bromomethyl-1,4-dioxa-7-azaspiro[4.4]nonane benzyl carbamate A 1.00 g (4.56 mmol) sample of 3-pyrrolidinone benzyl carbamate, from Step 2 Example 1, was dissolved in 20 mL of toluene with 1.00 g (11.4 mmol) of 3-bromo-1,2-propanediol and 0.043 g (0.23 mmol) of p-toluenesulfonic acid and heated at 110° C. for 24 hours. The reaction solution was poured into 20% sodium bicarbonate solution and the mixture extracted with ethyl acetate. The extract was dried over anhydrous sodium sulfate and the solvent removed under vacuum to afford 1.22 g of the title compound as a dark liquid: MS M/Z 356 (M). NMR: d 2.06 (m, 2H), 3.32 (m, 1H), 3.44 (m, 2H), 3.55 (m, 3H), 3.91 (m, 1H), 4.11 (m, 1H), 4.37 (m, 1H), 5.13 (s, 2H), 7.35 (m, 5H).

Step 2. 2-azidomethyl-1,4-dioxa-7-azaspiro[4.4]nonane benzyl carbamate

A 11.30 g (31.7 mmol) sample of 2-bromomethyl-1,4-dioxa-7-azaspiro[4.4]nonane benzyl carbamate, from Step 1, was dissolved in 225 mL of DMSO, 10.31 g (158.6 mmol) of sodium azide was added, and the solution was heated at 50° C. for 48 hours. The reaction was stopped by pouring the solution into 1 L of 20% sodium chloride solution, and the mixture was extracted with 3×200 mL of methylene chloride. The extract was dried over anhydrous sodium sulfate, and the solvent was removed under vacuum to afford 14.22 g of the title product, MS M/Z 336 (M+NH4), 319 (m+H); NMR: d 2.10 (m, 2H), 3.32 (m, 1H), 3.44 (m, 2H), 3.55 (m, 3H), 3.82 (m, 1H), 4.05 (m, 1H), 4.29 (m, 1H), 5.13 (s, 2H), 7.38 (m, 5H).

Step 3. 2-aminomethyl-1,4-dioxa-7-azaspiro[4.4]nonane 7-benzyl carbamate

To 7.0 g (22.0 mmol) of 2-azidomethyl-1,4-dioxa-7-azaspiro[4.4]nonane benzyl carbamate, from Step 2, dissolved in 48 mL of THF was added 0.557 g (14.72 mmol) of sodium borohydride. This mixture was heated to 60° C., then a solution of 2.94 mL (0.726 mmol) of methanol in 5 mL of THF was added dropwise over a 30 min period. The addition funnel was replaced with a condenser and the solution was heated at 70° C. for 5 hours. A solution on 1.4 g ammonium chloride in water was carefully added dropwise to quench any excess sodium borohydride, the solution was adjusted to pH 12 by the addition of 1M sodium hydroxide. The solution was poured into water and extracted with methylene chloride, which was dried over anhydrous sodium sulfate and removed by evaporation to afford 4.59 g of the title compound; MS M/Z 293 (M+H), with a suitable NMR analysis.

Step 4, 2-t-butoxycarbonylaminomethyl-1,4-dioxa-7-azaspiro[4.4]nonane 7-benzyl carbamate Under dry conditions, 4.50 g (15.4 mmol) of 2-aminomethyl-1,4-dioxa-7-azaspiro[4.4]nonane 7-benzyl carbamate, from Step 3, and 4.29 mL (30.8 mmol) of triethylamine were dissolved in 40 mL of methylene chloride. After cooling to 0° C., 5.04 g (23.1 mmol) of di-t-butyl dicarbonate was added in small portions over a 15 min period. The mixture was stirred at room temperature for 20 hours, then heated at 40° C. for 3 hours. The mixture was poured into 100 mL of 20% sodium chloride solution and extracted with 2×100 mL portions of methylene chloride. The organic layer was dried over sodium sulfate, filtered, and the solvent removed under vacuum. The crude product was purified by column chromatography on silica gel, eluting with methylene chloride and 2% methanol in methylene chloride, to afford 1.86 g of the title compound; MS M/Z 410 (M+NH4), 393 (M+H); NMR: d 1.45 (s, 9H), 2.05 (m, 2H), 3.20 (m, 1H), 3.42 (m, 2H), 3.68 (m, 1H), 4.03 (m, 1H), 4.20 (m, 1H), 4.82 (m, 1H), 5.12 (s, 2H), 7.36 (m, 5H).

Step 5. 2-t-butoxycarbonylaminomethyl-1,4-dioxa-7-azaspiro[4.4]nonane

A 1.86 g (4.74 mmol) sample of the doubly protected compound from Step 4 was dissolved in 100 mL of methanol and deprotected at the 7-position by hydrogenation at 4 atm of hydrogen for 18 hours at room temperature over 1.78 g of 20% Pd/C catalyst. The catalyst was removed by filtration and the solvent was removed under vacuum to afford 1.14 g of the title compound; NMR: d 1.45 (s, 9H), 2.02 (ddd, 2H, J=7.5 Hz, J=7.5 Hz, J=24.0 Hz), 3.18 (m, 2H), 3.33 (m, 4H), 3.66 (m, 1H), 4.00 (m, 1H), 4.19 (m, 1H).

Step 6. 1-(2,4-difluorophenyl)-7-(2-t-butoxycarbonylaminomethyl-1,4-dioxa-7-azaspiro[4.4]non-7-yl)-6-fluoro-1,4-dihydro-4-oxo-3-quinolinecarboxylic acid ethyl ester Following the procedure of Step 3 Example 135, substituting 2-t-butoxycarbonylaminomethyl-1,4-dioxa-7-azaspiro[4.4]nonane for the spiro compound of that example and heating for 48 hours instead of 96 hours, the title compound was prepared. Further purification by column chromatography on silica gel eluting stepwise with 0.5% and 3% methanol in methylene chloride, followed by removal of the solvent, afforded 0.703 g of the pure title compound; MS M/Z 604 (M+H); NMR: (CDCl3) d 1.39 (t, 3H, J=7.5 Hz), 1.45 (s, 9H), 2.10 (m, 2H), 3.39 (m, 4H), 3.47 (m, 1H), 3.58 (m, 1H), 3.69 (m, 1H), 4.04 (m, 1H), 4.21 (m, 1H), 4.37 (q, 2H, J=7.5 Hz), 4.83 (m, 1), 5.70 (dd, 1H, J=6.0 Hz, J=6.0 Hz) 7.14 (m, 2H), 7.49 (m, 1H), 8.02 (d, 1H, J=15 Hz), 8.25 (s, 1H).

Step 7. 1-(2,4-difluorophenyl)-7-(2-aminomethyl-1,4-dioxa-7-azaspiro[4.4]non-7-yl)-6-fluoro-1,4-dihydro-4-oxo-3-quinolinecarboxylic acid ethyl ester The 0.703 g of the boc-protected compound from Step 6 was stirred in 10 mL of trifluoroacetic acid at room temperature for 2 hours. The excess acid was evaporated off and the residue was dissolved in 300 mL of methanol. Six g of anion exchange resin (hydroxide form) was added, the mixture was stirred for an additional 2.5 hours and the resin filtered off, then the solvent was evaporated to afford 0.552 g of the title compound: NMR (CDCl$_3$) d 1.39 (t, 3H, J=7.5 Hz), 2.11 (m, 2H), 2.86 (m, 2H), 3.60 (m, 3H), 3.39 (m, 2H), 4.12 (m, 2H), 4.38 (q, 2H, J=7.5 Hz), 5.68 (m, 1H), 7.14 (m, 2H), 7.48 (m, 1H), 8.03 (d, 1H, j=15 Hz), 8.25 (s, 1H).

Step 8. 1-(2,4-difluorophenyl)-7-(2-aminomethyl-1,4-dioxa-7-azaspiro[4.4]non-7-yl)-6-fluoro-1,4-dihydro-4-oxo-3-quinolinecarboxylic acid dihydrochloride A 0.507 g (1 mmol) sample of the ester from Step 7 was dissolved in 5 mL of THF and 10 mL of 1.0M NaOH was added. The mixture was stirred and heated at 60° C. for 6 hours, during which it became homogeneous. The solution was poured into water and adjusted to pH 1-2. The water was evaporated under vacuum and the residue was stirred for 30 min in 50 mL of 1:1 methanol/methylene chloride. The solid was filtered off, the filtrate evaporated to dryness and washed with hexane to afford after drying 0.500 g of the title compound as a red-brown solid, mp 245° C. dec.; MS (DCl) M/Z 476 (M+H) (base); NMR: (TFA/AA) d 2.21 (m, 2H), 3.30–4.30 (m, 8H), 4.68 (m, 1H), 6.19 (m, 1H), 7.34 (m, 2H), 7.77 (m, 1H), 8.12 (d, 1, J=13.5 Hz), 9.07 (s, 1H). Analysis calculated for $C_{23}H_{20}F_3N_3O_5 \cdot 2H_2O \cdot 2HCl$: C, 47.27; H, 4.48; N, 7.19. Found: C, 47.60; H, 4.30; N, 7.36.

EXAMPLES 160–170

By following the procedures described in Example 159 and replacing the 1-(2,4-difluorophenyl)-6,7-difluoro-1,4-dihydro-4-oxo-3-quinolinecarboxylic acid ethyl ester (in Step 6), with the appropriate compound containing $R^1$, $R^3$, and A, below, Examples 160–170 may be prepared as disclosed in Table 7.

TABLE 7

| Example # | $R^1$ | $R^3$ | A |
|---|---|---|---|
| 160 | —C2H5 | H | CH |
| 161 | —C2H4—F | H | CH |
| 162 | —NH—CH3 | H | CH |
| 163 | -cyclopropyl | F | CH |
| 164 | -cyclopropyl | NH2 | CH |
| 165 | -cyclopropyl | H | C—CH3 |
| 166 | -cyclopropyl | H | C—Cl |
| 167 | -cyclopropyl | CH3 | CH |
| 168 | -t-butyl | H | CH |
| 169 | 3-methyl-1-butyn-3-yl | H | CH |
| 170 | bicyclo[1.1.1]pent-1-yl | H | CH |

EXAMPLE 171

1-(2,4-difluorophenyl)-7-(2-dimethylaminomethyl-1,4-dioxa-7-azaspiro[4.4]non-7-yl)-6-fluoro-1,4-dihydro-4-oxo-3-quinolinecarboxylic acid Step 1. 2-(N,N-dimethylaminomethyl)-1,4-dioxa-7-azaspiro[4.4]nonane benzyl carbamate A 0.607 g (1.7 mmol) sample of 2-bromomethyl-1,4-dioxa-7-azaspiro[4.4]nonane benzyl carbamate, from Step 1 Example 159, was dissolved in 15 mL of ethanol and sealed in a glass tube with 15 mL of dimethylamine. The tube was heated at 110° C. for 15 hours, cooled and opened. Then the solvent was removed under vacuum, and the product was purified by column chromatography on silica gel using 2% methanol/methylene chloride as eluant to afford 0.395 g of the title compound. NMR (CDCl$_3$)d 2.06 (m, 2H), 2.29 (s, 6H), 2.44 (m, 2H), 3.52 (m, 6H), 4.08 (m, 1H), 5.12 (s, 2H), 7.35 (m, 5H).

Step 2. 2-dimethylaminomethyl-1,4-dioxa-7-azaspiro[4.4]nonane

The carbamate group was removed from a 0.395 g (1.28 mmol) sample of the compound from Step 1 dissolved in 50 mL of methanol by hydrogenation at 4 atm of hydrogen for 24 hours at room temperature over 0.59 g of 20% Pd/C. The catalyst was filtered off, and the solvent was removed under vacuum to afford the title compound, MS M/Z 187 (M+H).

Step 3. 1-(2,4-difluorophenyl)-7-(2-dimethylaminomethyl-1,4-dioxa-7-azaspiro[4.4]non-7-yl)-6-fluoro-1,4-dihydro-4-oxo-3-quinolinecarboxylic acid ethyl ester Following the procedure of Step 3 Example 135, substituting 0.202 g (1.5 mmol) of 2-dimethylaminomethyl-1,4-dioxa-7-azaspiro[4.4]nonane for the spiro compound of that example and heating for 24 hours instead of 96 hours, the title compound was prepared. Further purification by column chromatography on silica gel eluting stepwise with 0.5% and 3% methanol in methylene chloride, followed by removal of the solvent, afforded 0.307 g of the pure title compound.

Step 4. 1-(2,4-difluorophenyl)-7-(2-dimethylaminomethyl-1,4-dioxa-7-azaspiro[4.4]non-7-yl)-6-fluoro-1,4-dihydro-4-oxo-3-quinolinecarboxylic acid A 0.3.07 g (1 mmol) sample of the ester from Step 3 was dissolved in 5 mL of THF and 10 mL of 1.0M NaOH was added. The mixture was stirred and heated at 55° C. for 20 hours, after which it was poured into water and acidified to pH 4 with acetic acid. This solution was extracted three times with methylene chloride, then the organic layer was dried over anhydrous sodium sulfate and the solvent was removed by evaporation under vacuum. The crude product was recrystallized from ethanol/hexane to afford 0.120 g of the title compound, mp 184°–185° C.; MS (DCl) M/Z 504 (M+H); NMR d 2.13 (m, 2H), 2.31 (s, 6H), 2.50 (m, 2H), 3.54 (m, 5H), 4.13 (m, 1H), 4.30 (m, 1 H), 5.87 (d, 1H, J=7.5 Hz), 7.28 (m, 2H), 7.63 (m, 1H), 7.96 (d, 1H, J=15 Hz), 8.58 (s, 1H). Analysis calculated for $C_{25}H_{24}F_3N_3O_5$: C, 59.64; H, 4.81; N, 8.35. Found: C, 59.08; H, 4.83; N, 8.11.

EXAMPLES 172–182

By following the procedures described in Example 171 and replacing 1-(2,4-difluorophenyl)-6,7-difluoro-1,4-dihydro-4-oxo-3-quinolinecarboxylic acid ethyl ester (in Step 3), with the appropriate compound containing $R^1$, $R^3$, and A, below, Examples 172–182 may be prepared as disclosed in Table 8.

TABLE 8

| Example # | R¹ | R³ | A |
|---|---|---|---|
| 172 | —C2H5 | H | CH |
| 173 | —C2H4—F | H | CH |
| 174 | —NH—CH3 | H | CH |
| 175 | -cyclopropyl | F | CH |
| 176 | -cyclopropyl | NH2 | CH |
| 177 | -cyclopropyl | H | C—CH3 |
| 178 | -cyclopropyl | H | C—Cl |
| 179 | -cyclopropyl | CH3 | CH |
| 180 | -t-butyl | H | CH |
| 181 | 3-methyl-1-butyn-3-yl | H | CH |
| 182 | bicyclo[1.1.1]pent-1-yl | H | CH |

EXAMPLE 183

7-(3,3-Dimethoxy-4-methylpyrrolidin-1-yl)-1-(2,4-difluorophenyl)-6-fluoro-1,4-dihydro-4-oxo-3-quinolinecarboxylic acid Step 1: 4-Methyl-3-pyrrolidinol a. A 125 mL sample of methyl methacrylate (1.0 mol) and 100 mL (0.91 mol) of benzylamine were heated at 120° C. for 48 hours. The product was distilled at 94°–100° C. at 0.3 Torr to yield 142.28 g of 3-(N-benzylamino)-2-methylpropanoic acid ethyl ester., NMR (CDCl$_3$) d 1.15 (d, 3H, J=6.9 Hz), 1.24 (t, 2H, J=6.9 Hz), 1.63 (s(br), 1H), 2.65 (m, 2H), 2.87 (m, 1H), 3.79 (s, 2H), 4.14 (q, 2H, J=6.9 Hz), 7.32 (m, 5H).

b. The 142.28 g of the ester from step 1a was heated at 85° C. for 74 hours with 350 mL of triethylamine and 86.67 g (0.71 mol) of ethyl chloroacetate. The triethylamine was then removed under vacuum, and the residue was dissolved in water and extracted into methylene chloride. The extract was dried over anhydrous sodium sulfate and the solvent was removed by evaporation under vacuum. The crude product was purified in a kugelrohr apparatus (130°–150° C. @ 0.5 Torr) to yield 173.4 g of 3-(N-benzylamino-N-(2-acetic acid ethyl ester))-2-methylpropanoic acid ethyl ester, MS M/Z 308 (M+H); NMR (CDCl$_3$) d 1.13 (d, 3H, J=7.5 Hz), 1.26 (dt, 6H, J=7.5 Hz), 2.69 (m, 1H), 2.91 (m, 2H), 3.30 (d, 2H, J=3 Hz), 3.83 (d, 2H, J=3 Hz), 4.15 (dq, 4H, J=7.5 Hz), 7.29 (m, 5H).

c. A 50.0 g (162.7 mmol) sample of the diester from step b was cyclized under dry conditions by adding it dropwise to a stirred solution of potassium t-butoxide (19.15 g, 170.8 mmol) in 650 mL of toluene at 0° C. After 3 hours at room temperature, the mixture was poured into water, acidified to pH 4 with acetic acid, and washed well. The organic layer dried over anhydrous sodium sulfate and the solvent was removed by evaporation under vacuum. The crude product was purified in a kugelrohr apparatus (100°–130° C. @ 0.5 Torr) to yield 30.15 g of 1-benzyl-4-methyl-pyrrolidin-3-one-2-carboxylic acid ethyl ester, NMR (CDCl$_3$) d 1.11 (d, 3H, J=7.5 Hz), 1.24 (t, 3H, J=7.5 Hz), 2.63 (m, 1H), 3.48 (s, 1H), 3.81 (m, 4H), 4.15 (m, 2H), 7.32 (m, 5H).

d. A 30.15 g (115.4 mmol) sample of the ester from step c was hydrolyzed and decarboxylated by adding to 280 mL of 1M HCl and heating at 100° C. under reflux conditions for 12 hours. The mixture was then poured over ice and the impurities extracted into methylene chloride. The aqueous solution was then adjusted to pH 8 with potassium carbonate and the product extracted into methylene chloride, which was then dried over anhydrous sodium sulfate. The solvent was removed by evaporation under vacuum, to yield 9.95 g of 1-benzyl-4-methylpyrrolidin-3-one, NMR (CDCl$_3$) d 1.12 (d, 3H, J=7.5 Hz), 2.50 (m, 1H), 2.75 (m, 2H), 3.33 (m, 2H), 3.69 (d, 2H, J=7.5 Hz), 7.32 (m, 5H).

e. A 15.58 g (82.3 mmol) sample of the ketone from step d was reduced to the alcohol by dissolving it in 32 mL of ethanol and adding the solution dropwise to a stirred suspension of sodium borohydride (3.11 g, 82.3 mmol) in 32 mL of ethanol at 0° C. The suspension was then stirred for 30 min at 0° C. and for 4 hours at room temperature. The solvent was then removed and the residue suspended in water. The product was extracted with methylene chloride and dried over anhydrous sodium sulfate, and the solvent was removed by evaporation under vacuum. The crude product was purified in a kugelrohr apparatus (160°–180° C. @ 1.0 Torr) to yield 1-benzyl-4-methyl-3-pyrrolidinol, MS M/Z 192 (M+H); NMR (CDCl$_3$) d 1.04 (d, 3H, J=7.5 Hz), 1.90 (dd, 1H, J=7.5 Hz, J=9.0 Hz), 2.14 (m, 1H), 2.55 (dd, 1H, J=6.0 Hz, J=10.5 Hz), 2.82 (dd, 1H, J=3.0 Hz, J=10.5 Hz), 3.13 (dd, 1H, J=3.0 Hz, J=3.0 Hz), 3.82 (m, 2H), 3.95 (m, 1H), 7.33 (m, 5H).

f. The pyrrolidinol (16.56 g, 86.6 mmol) was debenzylated by catalytic hydrogenation in 250 mL of methanol at 4 atm of hydrogen and room temperature for 24 hours over 8.28 g of 20% Pd/C. The catalyst was removed by filtration, and the solvent was removed under vacuum to afford the title compound, which was taken directly to the next step.

Step 2. 4-Methyl-3-pyrrolidinol benzyl carbamate

A protecting group was added to a 1.58 g (15.6 mmol) sample of the 4-methyl-3-pyrrolidinol from Step 1 by suspending it in 18.75 mL (18.75 mmol) of 1M sodium hydroxide at 0° C. and adding dropwise 2.23 mL (15.6 mmol) of benzylchloroformate, dissolved in 5 mL of ethyl ether, then stirring for 1.5 hours at 0° C. The solution was then diluted with water and the product extracted into ethyl acetate, which was dried over anhydrous sodium sulfate, then the solvent was removed by evaporation under vacuum to afford 3.26 g of the title compound, MS M/Z 236 (M+H).

Step 3. 4-Methylpyrrolidin-3-one benzyl carbamate

A 14.52 g (61.7 mmol) sample of the compound from Step 2 and 68.8 mL (493 mmol) of triethylamine were dissolved in 65 mL of DMSO and adding dropwise to a stirred solution of 29.47 g (185 mmol) of sulfur trioxide pyridine complex dissolved in 65 mL of DMSO cooled to 0° C. After 18 hours of reaction at room temperature, the solution was poured into water and the mixture extracted into methylene chloride. This was dried over anhydrous sodium sulfate and the solvent was removed by evaporation under vacuum. The crude product was purified in a kugelrohr apparatus (150° C. @ 0.5 Torr), to afford 8.94 g of the title compound, MS M/Z 234 (M+H), 251 (M+NH$_4$);

Step 4. 3,3-Dimethoxy-4-methylpyrrolidine benzyl carbamate

A 1.20 g (5.1 mmol) sample of the compound from Step 3 was dissolved in 12 mL of methanol, 11.5 mL (10.5 mmol) of methyl orthoformate and a catalytic amount of p-toluenesulfonic acid was added and the mixture was heated at 65°-70° C. for 9 hours. The solution was diluted with ethyl acetate and washed with 5% sodium bicarbonate solution. The organic layer was dried over anhydrous sodium sulfate and the solvent was removed by evaporation under vacuum. The product was purified by column chromatography on silica gel, eluting with methylene chloride then 0.5% methanol in methylene chloride to afford 0.471 g of the title compound, NMR (CDCl$_3$) d 1.02 (d, 3H, J=7.5 Hz), 2.33 (m, 1H), 3.25 (s, 6H), 3.40 (m, 4H), 5.13 (s, 2H), 7.37 (m, 5H).

Step. 5. 3.3-Dimethoxy-4-methylpyrrolidine

A 0.603 g (2.2 mmol) sample of the compound from Step 4 was deprotected under hydrogenation conditions similar to those described in Step 1f, above. The catalyst was removed by filtration, and the solvent was removed under vacuum to afford 0.353 g of the title compound, MS M/Z 114 (M—OCH$_3$), 146 (M+H).

Step 6. 7-(3,3-Dimethoxy-4-methylpyrrolidin-1-yl)-1-(2,4-difluorophenyl)-6-fluoro-1,4-dihydro-4-oxo-3-quinolinecarboxylic acid ethyl ester Following the procedure of Step 3 Example 135, substituting 0.238 g (1.5 mmol) of 3,3-dimethoxy-4-methylpyrrolidine (from Step 5 above) for the spiro compound of that example and heating at 55° C. instead of 45° C. and for 114 hours instead of 96 hours, the title compound was prepared. Further purification by column chromatography on silica gel, eluting stepwise with 0.5% and 2% methanol in methylene chloride, followed by removal of the solvent, afforded 0.202 g of the pure title compound, NMR (CDCl$_3$) d 1.03 (dd, 3H, J=7.5 Hz, J=1.5 Hz), 1.40 (t, 3H, J=7.5 Hz),2.36 (m, 1H), 2.96 (m, 1H), 3.22 (s, 3H), 3.26 (s, 3H), 3.49 (m, 1H), 3.53 (m, 2H), 4.38 (q, 2H, J=7.5 Hz), 5.46 (m, 1H), 7.14 (m, 2H), 7.48 (m, 1H).

Step 7. 7-(3,3-Dimethoxy-4-methylpyrrolidin-1-yl)-1-(2,4-difluorophenyl)-6-fluoro-1,4-dihydro-4-oxo-3-quinolinecarboxylic acid A 0.202 g (1 mmol) sample of the ester from Step 6 was dissolved in 2 mL of THF and 10 mL of 1.0M NaOH was added. The mixture was stirred and heated at 60° C. for 3 hours, then at 85° C. for 1 hour to remove the THF, after which it was poured into water and acidified to pH 6 with acetic acid. The precipitated product was filtered off, rinsed with water and dried to afford 0.158 g of the title compound as a yellow solid, mp 193°-194° C.; MS M/Z 463 (M+H); NMR d 1.04 (dd, 3H, J=1.5 Hz, J=4.5 Hz), 2.43 (m, 1H), 3.04 (m, 1H), 3.22 (s, 3H), 3.26 (s, 3H), 3.57 (m, 3H), 5.83 (dd, 1H, J=3.0 Hz), 7.27 (m, 2H), 7.60 (m, 1H), 7.96 (d, 1H, J=9.0 Hz), 8.59 (s, 1H). Analysis calculated for C$_{23}$H$_{21}$F$_3$N$_2$O$_5$·0.5 H$_2$O: C, 58.72; H, 4.71; N, 5.95. Found: C, 59.08; H, 4.67; N, 5.86.

EXAMPLES 184-194

By following the procedures described in Example 183 and replacing 1-(2,4-difluorophenyl)-6,7-difluoro-1,4-dihydro-4-oxo-3-quinolinecarboxylic acid ethyl ester (in Step 6), with the appropriate compound containing R$^1$,R$^3$, and A, below, Examples 184-194 are prepared as disclosed in Table 9.

TABLE 9

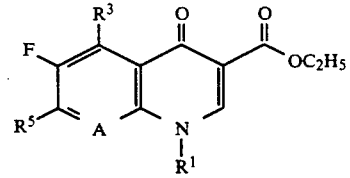

| Example # | R$^1$ | R$^3$ | A |
|---|---|---|---|
| 184 | —C2H5 | H | CH |
| 185 | —C2H4—F | H | CH |
| 186 | —NH—CH3 | H | CH |
| 187 | -cyclopropyl | F | CH |
| 188 | -cyclopropyl | NH2 | CH |
| 189 | -cyclopropyl | H | C—CH3 |
| 190 | -cyclopropyl | H | C—Cl |
| 191 | -cyclopropyl | CH3 | CH |
| 192 | -t-butyl | H | CH |
| 193 | 3-methyl-1-butyn-3-yl | H | CH |
| 194 | bicyclo[1.1.1]pent-1-yl | H | CH |

EXAMPLE 195

1-Cyclopropyl-6,8-difluoro-7-(3,3-dimethoxy-4-methylpyrrolidin-1-yl)-1,4-dihydro-4-oxo-3-quinolinecarboxylic acid Step 1. 1-Cyclopropyl-6,8-difluoro-7-(3,3-dimethoxy-4-methylpyrrolidin-1-yl)-1,4-dihydro-4-oxo-3-quinolinecarboxylic acid ethyl ester Following the procedure of Step 1 Example 80, substituting 0.279 g (1.92 mmol) of 3,3-dimethoxy-4-methylpyrrolidine (from Step 5 Example 183) for the spiro compound of that example and heating at 45° C. instead of 65° C. and for 72 hours instead of 48 hours, the title compound was prepared. The solvent was evaporated and the ester purified by chromatography on a silica gel column using as eluant 0.5% methanol increasing to 3% methanol in methylene chloride The solvent was removed to afford 0.135 g of the title compound, which was taken to the next step directly.

Step 2: 1-Cyclopropyl-6,8-difluoro-7-(3,3-dimethoxy-4-methylpyrrolidin-1-yl)-1,4-dihydro-4-oxo-3-quinolinecarboxylic acid The ester from Step 1 was hydrolyzed via a procedure similar to that of Step 7 Example 183 to afford 0.096 g of the title compound, mp 214°-216° C.; MS (FAB) M/Z 409 (M+H) 391 (M+H-H$_2$O); NMR: d 1.13 (d, 3H, J=7.5 Hz), 1.26 (m, 4H), 2.48 (m, 1H), 3.32 (s, 3H), 3.38 (s, 3H), 3.44 (m, 1H), 3.74 (m, 1H), 3.96 (m, 1H), 4.08 (m, 1H), 4.19 (m, 1H), 7.80 (dd, 1H, J=13.5 Hz, J=1.5 Hz), 8.77 (s, 1H). Analysis calculated for C$_{20}$H$_{22}$F$_2$N$_2$O$_5$: C, 58.82; H,; 5.43 N, 6.86. Found: C, 58.34; H, 5.47; N,.6.68.

EXAMPLE 196

1-(2,4-difluorophenyl)-7-(1,5-dioxa-9-azaspiro[5.5]undec-9-yl)-6-fluoro-1,4-dihydro-4-oxo-3-quinolinecarboxylic acid Step 1. 4-Hydroxypiperidine benzyl carbamate To a 35.43 g (350 mmol) sample of 4-hydroxypiperidine in 420 mL of 1M sodium hydroxide stirred at 0° C. was slowly added 50.0 mL (350 mmol) of benzylchloroformate dissolved in 100 mL of ethanol. The mixture was stirred for 3 hours at 0° C., then diluted with water, and the product extracted into methylene chloride. The organic layer was dried over anhydrous sodium sulfate and the solvent was removed by evaporation under vacuum, to yield the title product as a yellow liquid, MS M/Z 253 (M+NH4), 236 (M+H); NMR d 1.49 (m, 2H), 1.71 (s, 1H), 1.87 (m, 2H), 3.15 (ddd, 2H, J=3 Hz, J=3 Hz, J=9 Hz), 3.88 (m, 2H), 3.92 (m, 1H), 5.12 (s, 2H), 7.36 (m, 5H).

Step 2. Piperidin-4-one benzyl carbamate

To a 10.0 g (42.5 mmol) sample of the protected alcohol from Step 1, dissolved in 90 mL of DMSO and cooled to 0° C., was added 47.39 mL (340 mmol) of triethylamine, then a solution of 20.29 g (127.5 mmol) of sulfur trioxide pyrdine complex dissolved in 90 mL of DMSO was added dropwise to the stirred solution. The ice bath was removed and the solution stirred at room temperature for 16 hours, then the reaction was quenched by pouring the solution into 1 L of water. The mixture was extracted with methylene chloride, and the solvent was dried over anhydrous sodium sulfate and removed by evaporation under vacuum. The crude product was purified in a kugelrohr apparatus (130° C. @ 4 Torr) to afford 7.14 g of the title compound, MS M/Z 234 (M+H), 251 (M+NH4); NMR (CDCl3) d 2.45 (t, 4H, J=6 Hz), 3.81 (t, 4H, J=6 Hz), 5.18 (s, 2H), 7.37 (m, 5H).

Step 3. 1,5-Dioxa-9-azaspiro[5.5]undecane benzyl carbamate

Following the procedure of Step 1 Example 14, substituting 2.33 g (10 mmol) of piperidin-4-one benzyl carbamate for the protected ketone of that example and heating at 140° C. instead of 125° C. for 8 hours instead of 48 hours, the title compound was prepared. After extraction from a basic aqueous solution as described, the product was purified by column chromatography on silica gel, eluting with 0.5% methanol/methylene chloride, to afford 1.15 g of the title compound, MS M/Z 292; NMR (CDCl3) d 1.73 (m, 2H), 1.87 (m, 4), 3.52 (dd, 4H, J=6.6 Hz), 3.91 (dd, 4H, J=6.6 Hz), 5.12 (s, 2H), 7.34 (m, 5H).

Step 4. 1,5-Dioxa-9-azaspiro[5.5]undecane

The protecting group was removed following the procedure of Step 2 Example 14, substituting 1.15 g of 1,5-dioxa-9-azaspiro[5.5]undecane benzyl carbamate for the carbamate of that example to afford 0.622 g of the title compound, MS M/Z 158 (M+H); NMR (CDCl3) d 1.73 (q, 2H, J=6 Hz), 1.97 (dd, 4H, J=6 Hz, J=6 Hz), 2.97 (dd, 4H, J=6 Hz, J=6 Hz), 3.91 (dd, 4H, J=6 Hz, J=6 Hz), 5.45 (s(br), 1H).

Step 5, 1-(2,4-difluorophenyl)-7-(1,5-dioxa-9-azaspiro[5.5]undec-9-yl)-6-fluoro-1,4-dihydro-4-oxo-3-quinolinecarboxylic acid ethyl ether Following the procedure of Step 3 Example 14, substituting 0.475 g (1.3 mmol) of 1,5-dioxa-9-azaspiro[5.5]undecane for the spiro compound of that example, and heating for 96 hours instead of 24 hours, the title compound was prepared. The solvent was removed and the crude product dried under vacuum, then dissolved in methylene chloride, which was washed with 0.2N HCl, 5% sodium bicarbonate solution, and water. The methylene chloride was dried over anhydrous sodium sulfate and the solvent was removed by evaporation under vacuum. The product was recrystallized from ethanol/water, filtered, washed with ethanol, and dried under vacuum to afford 0.390 g of the title compound, which was taken directly to the next step.

Step 6. 1-(2,4-difluorophenyl)-7-(1,5-dioxa-9-azaspiro[5.5]undec-9-yl)-6-fluoro-1,4-dihydro-4-oxo-3-quinolinecarboxylic acid The ester from Step 5 was hydrolyzed via a procedure similar to that of Step 4 Example 14, followed by heating and washing with ethanol, filtration and drying under vacuum, to afford 0.316 g of the title compound, MS (FAB) M/Z 475 (M+H), 457 (M+H-H2O); NMR (CDCl3) d 1.73 (m, 2H, J=6 Hz), 2.02 (dd, 4H, J=6 Hz), 3.14 (dd, 4H, J=6 Hz), 3.90 (dd, 4H, J=6 Hz), 6.23 (dd, 1H, J=1.5, J=4.5 Hz), 7.18 (m, 2H), 7.47 (m, 1H), 8.06 (d, 1H, J=12 Hz), 8.48 (s, 1H), 14.85 (s, 1H). Analysis calculated for $C_{24}H_{21}F_3N_2O_5$: C, 60.76; H, ;4.46 N, 5.90. Found: C, 60.38; H, 4.51; N,.5.83.

EXAMPLES 197-207

By following the procedures described in Example 196 and replacing 1-(2,4-difluorophenyl)-6,7-difluoro-1,4-dihydro-4-oxo-3-quinolinecarboxylic acid ethyl ester (in Step 3), with the appropriate compound containing $R^1, R^3$, and A, below, Examples 197-207 may be prepared as disclosed in Table 10.

TABLE 10

| Example # | $R^1$ | $R^3$ | A |
|---|---|---|---|
| 197 | —C2H5 | H | CH |
| 198 | —C2H4—F | H | CH |
| 199 | —NH—CH3 | H | CH |
| 200 | -cyclopropyl | F | CH |
| 201 | -cyclopropyl | NH2 | CH |
| 202 | -cyclopropyl | H | C—CH3 |
| 203 | -cyclopropyl | H | C—Cl |
| 204 | -cyclopropyl | CH3 | CH |
| 205 | -t-butyl | H | CH |
| 206 | 3-methyl-1-butyn-3-yl | H | CH |
| 207 | bicyclo[1.1.1]pent-1-yl | H | CH |

EXAMPLE 208

1-Cyclopropyl-6-fluoro-7-(9-amino-1,4-dioxa-7-azaspiro[4.4]non-7-yl)-1,4-dihydro-4-oxo-3-quinolinecarboxylic acid hydrochloride Step 1: 4-Amino-3-pyrrolidinol benzyl carbamate a. A 50 g (723 mmol) sample of 3-pyrroline was dissolved in 868 mL of 1M NaOH in a 2 L flask and cooled to 0° C. To this was added dropwise over a one hour period a solution of 115 g (721 mmol) of benzylchloroformate in 100 mL of diethyl ether, and the reaction was stirred for 4 hours. The solution was diluted with 500 mL of water and extracted with 4×300 ML portions of methylene chloride. The solvent was dried over anhydrous sodium sulfate and the solvent was removed by evaporation under vacuum to afford 144.6 g of 3-pyrroline benzyl carbamate, MS (DCI) M/Z 204 (M+H), 221 (M+NH4).

b. A 15.00 g (74 mmol) sample of the 3-pyrroline benzyl carbamate from Step 1a was dissolved in 200 mL of methylene chloride and cooled to 0° C. A 46.3 g (267 mmol) sample of m-chloroperbenzoic acid was dissolved in 500 mL of methylene chloride and added dropwise with stirring over a period of 1 hours. The flask was then equipped with a condenser and the temperature was increased to 45° C. for 18 hours. The solution was cooled to room temperature, 2 g of sodium bisulfite was added, the solution was stirred for 30 min then poured into 1 L of 1M NaOH. and washed in a separatory funnel. The methylene chloride was then washed with 2×500 mL portions of potassium carbonate solution, dried over anhydrous sodium sulfate, and the solvent was filtered and removed by evaporation under vacuum. to afford 14.26 g of 3,4-epoxypyrrolidine benzyl carbamate, MS (DCl) M/Z 220 (M+H), 237 (M+NH$_4$); NMR (CDCl$_3$) d 3.39 (ddd, 2H, J=6.0, 1.5, 13.5 Hz), 3.87 (dd, 2H, J=12, 15 Hz), 5.12 (d, 2, J=3 Hz), 7.35 (m, 5H).

c. A 12.05 g (41 mmol) sample of the epoxy compound from Step 1b was dissolved in 120 mL of acetone, then a solution of 8.04 g (123 mmol) of sodium azide in 80 mL of water was added, and the solution was stirred at 60° C. for 24 hours. The reaction was diluted with 100 mL of water and the product extracted with 3×300 mL portions of methylene chloride, which was dried over anhydrous sodium sulfate, filtered, and the solvent was removed by evaporation under vacuum to afford 15.69 g of 4-azido-3-pyrrolidinol benzyl carbamate, MS (DCl) M/Z 263 (M+H), 280 (M+NH$_4$); NMR (CDCl$_3$) d 3.45 (m, 2H), 3.63 (dd, 1H, J=6, 12 Hz), 3.73 (m, 1H), 3.93 (m, 1H), 4.22 (m, 1H), 5.13 (m, 4H), 7.33 (m, 10H).

d. A 16.84 g (64 mmol) of the azido compound from Step 1c was dissolved in 250 mL of ethyl acetate and reduced over 3.3 g of Raney nickel at 4 atm hydrogen for 18 hours at room temperature. The catalyst was removed by filtration, and the solvent was removed under vacuum to afford 14.9 g of 4-amino-3-pyrrolidinol benzyl carbamate, MS (DCl) M/Z 237 (M+H), 254 (M+NH$_4$).

Step 2. 4-amino-3-pyrrolidinol 1,4-bis-benzyl carbamate

The 14.9 g (63 mmol) of 4-amino-3-pyrrolidinol benzyl carbamate from Step 1d was dissolved in 75 mL of 1M NaOH and cooled to 0° C. To this was added dropwise with stirring over 25 min 9.90 mL (69 mmol) of benzylchloroformate dissolved in 20 mL of diethyl ether, and the mixture was stirred for 2 hours. The mixture was poured into 200 mL of water, extracted with 3×200 mL portions of methylene chloride, which was dried over anhydrous sodium sulfate, and the solvent was removed by evaporation under vacuum to yield the doubly protected aminopyrrolidinol. The crude product was purified on a column of 200–400 mesh silica gel, eluting with 0.5% increasing to 2% methanol/methylene chloride to afford 13.93 g of 4-amino-3-pyrrolidinol 1,4-bis-benzyl carbamate, MS (DCl) M/Z 371 (M+H), 384 (M+NH$_4$); NMR (CDCl$_3$) d 3.33 (m, 2H), 3.68 (dd, 1H, J=6, 12 Hz), 3.83 (dd, 1H, J=6, 12 Hz), 3.99 (m, 1H), 4.25 (m, 1H), 5.09 (m, 2H), 7.32 (m, 10H).

Step 3. 4-aminopyrrolidin-3-one 1,4-bis-benzyl carbamate

To oven-dried glassware maintained under dry N$_2$ was added 220 mL of methylene chloride and 10.8 mL of DMSO and the solution was cooled to 0° C. To this was added 13.56 mL (90 mmol) of phenyl dichlorophosphate, 21.2 mL of triethylamine, and a 11.28 g (30 mmol) sample of the compound from Step 2 dissolved in 110 mL of methylene chloride was added dropwise over 1 hours. The ice bath was removed and the reaction was stirred at room temperature for 5 hours. The solution was then poured into 1 L of 20% sodium chloride solution and the product was extracted with three washings of methylene chloride. The methylene chloride solution was washed with 20% NaCl solution to remove excess DMSO, dried over anhydrous sodium sulfate, filtered, and the solvent was removed by evaporation. The product was further purified by chromatography on 200–400 mesh silica gel (solvent 0.5–2.0% methanol in methylene chloride) which after removal of the solvent under vacuum afforded 4.08 g of 4-aminopyrrolidin-3-one 1,4-bis-benzyl carbamate, MS (DCl)M/Z 369 (M+H), 386 (M+NH$_4$); NMR (CDCl$_3$) d:3.35 (m, 1H), 3.80 (m, 1H), 4.10 (m, 1H), 4.24 (m, 1H), 4.53 (m, 1H), 5.09 (s, 2H), 5.18 (s, 2H), 5.35 (m, 1H), 7.34 (m, 10H).

Step 4. 9-Amino-1,4-dioxa-7-azaspiro[4.4]nonane 1,4-bis-benzyl carbamate

A 4.06 g (11 mmol) sample of the ketone compound from Step 3 was dissolved in 80 mL of toluene, and 1.54 mL (27.6 mmol) of ethylene glycol and 0.1 g of p-toluenesulfonic acid was added, then the mixture was heated at 110° C. with stirring for 5 hours. The contents were cooled, poured into 200 mL of 5% sodium bicarbonate and extracted (3×100 mL) with ethyl acetate, which was dried over anhydrous sodium sulfate, and the solvent was removed by evaporation under vacuum. The residue was dissolved in a small amount of methylene chloride, and passed through a column of silica gel to remove the polar impurities. The solvent was removed by evaporation under vacuum to afford 3.24 g of the title compound, MS (DCl)M/Z 430 (M+NH$_4$); NMR (CDCl$_3$) d: 3.25 (m, 1H), 3.50 (ddd, 2H, J=12.0, 12.0, 18.0 Hz), 3.97 (m, 5H), 5.10 (m, 4H), 7.33 (m, 10H). Analysis calculated for C$_{22}$H$_{24}$N$_2$O$_6$: C, 64.07; H, 5.86; N, 6.79. Found: C, 63.67; H, 5.71; N, 6.57.

Step 5. 9-Amino-1,4-dioxa-7-azaspiro[4.4]nonane

The protecting groups were removed from a 2.94 g (7.1 mmol) sample of the compound from Step 4, by hydrogenating over 0.60 g 10% Pd/C (dry) in 100 ML of ethyl acetate, 50 mL of 2-propanol, at 4 atm of hydrogen, for 5 days at room temperature. The catalyst was removed by filtration, and the solvent was removed under vacuum to afford 0.335 g of the title compound, MS (DCl) M/Z 145 (M+H), which was taken directly to next step.

Step 6. 1-Cyclopropyl-6-fluoro-7-(9-amino-1,4-dioxa-7-azaspiro[4.4]non-7-yl)-1,4-dihydro-4-oxo-3-quinolinecarboxylic acid ethyl ester Into oven-dried glassware under a N$_2$ atmosphere were placed 0.258 g (1.8 mmol) of 9-amino-1,4-dioxa-7-azaspiro[4.4]nonane, from Step 5 above, 0.350 g of 1-cyclopropyl-6,7-difluoro-1,4-dihydro-4-oxo-3-quinolinecarboxylic acid ethyl ester (preparation described by U. Peterson et al. German Pat. Appl. DE 3420798, Dec. 5, 1985), 15 mL of dry pyridine and 0.665 mL (4.0 mmol) of triethylamine. The reaction was stirred with heating at 40° C. for 184 hours. The solvent was removed, and the crude product was dissolved in methylene chloride which was washed twice with water, and dried over anhydrous sodium sulfate. After filtration the solvent was removed by evaporation under vacuum to obtain the crude product. The product was purified with column chromatography over silica gel, eluting with 1% increasing to 10% methanol/methylene chloride. The solvent was removed by evaporation under vacuum to afford 0.138 g of the title compound, MS M/Z 418 (M+H); NMR (CDCl$_3$) d 1.17 (m, 4H), 1.41 (t, 3H, J=7.5 Hz), 3.43 (m, 5H), 4.08 (m, 4H), 4.38 (q, 2H, J=7.5 Hz), 6.82 (d, 1H, J=7.5 Hz), 7.99 (d, 1H, J=15 Hz), 8.48 (s, 1H).

Step 7. 1-Cyclopropyl-6-fluoro-7-(9-amino-1,4-dioxa-7-azaspiro[4.4]non-7-yl)-1,4-dihydro-4-oxo-3-quinolinecarboxylic acid hydrochloride A 0.138 sample of the compound from Step 7 was dissolved in 5 mL of THF, to which was added 3.3 mL of 1M NaOH, and the mixture was heated under reflux at 50° C. for 1.5 hours, then at 80° C. for 1.5 hours without the condenser to remove the THF. The solution was poured into 25 mL of water, conc. HCl added to adjust the solution to pH 1, most of the water removed under vacuum, and the crude product filtered off. The filtrate was evaporated to dryness, the residue suspended in 1:1 methylene chloride/methanol and the solution stirred for 4 hours. The insoluble salts were filtered off and the filtrate was evaporated to dryness. This material was combined with the 1st crop of crude product, and recrystallized from i-propanol/ethanol. This solid was washed with 4:1 methylene chloride/methanol, the insoluble salts were filtered off and the filtrate was evaporated to dryness to afford 0.113 g of the hydrochloride salt of the title compound as a light orange solid, mp 220°–222° C. MS (FAB) M/Z 390 (M+H); NMR d 1.51 (m, 4H), 4.9 (m, 9H), 7.41 (d, 1H, J=7.5 Hz), 8.12 (d, 1H, J=13.5 Hz), 9.18 (s, 1H). Analysis calculated for $C_{19}H_{21}ClFN_3O_5 \cdot 1.25\ H_2O$: C, 50.90; H, 5.28; N, 9.37. Found: C, 50.74 H, 4.83; N, 8.66.

EXAMPLES 209–219

By following the procedures described in Example 208 and replacing 1-cyclopropyl-6,7-difluoro-1,4-dihydro-4-oxo-3-quinolinecarboxylic acid ethyl ester (in Step 6) with the appropriate compound containing $R^1, R^3$, and A, below, Examples 209–219 may be prepared as disclosed in Table 11.

TABLE 11

| Example # | $R^1$ | $R^3$ | A |
|---|---|---|---|
| 209 | —C2H5 | H | CH |
| 210 | —C2H4—F | H | CH |
| 211 | —NH—CH3 | H | CH |
| 212 | -cyclopropyl | F | CH |
| 213 | -cyclopropyl | NH2 | CH |
| 214 | -cyclopropyl | H | C—CH3 |
| 215 | -cyclopropyl | H | C—Cl |
| 216 | -cyclopropyl | CH3 | CH |
| 217 | -t-butyl | H | CH |
| 218 | 3-methyl-1-butyn-3-yl | H | CH |
| 219 | bicyclo[1.1.1]-pent-1-yl | H | CH |

EXAMPLES 220–273

By following the procedures described in Example 208 and replacing 9-amino-1,4-dioxa-7-azaspiro[4.4]nonane in Step 5 with the appropriate ketal compound, Examples 220–273 (in which A=CH and $R^1$=cyclopropyl) may be prepared as disclosed in Table 12.

TABLE 12

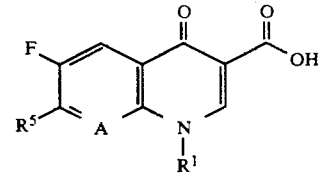

| Example # | $R^5$ is derived from ketal compound: |
|---|---|
| *220 | 2-aminomethyl-3,3-dimethoxypyrrolidine |
| *221 | 6-aminomethyl-1,4-dioxa-7-azaspiro[4.4]nonane |
| *222 | 8-aminomethyl-2-ethyl-1,4-dioxa-7-azaspiro[4.4]nonane |
| 223 | 9-chloro-1,4-dioxa-7-azaspiro[4.4]nonane |
| 224 | 2,3-dimethyl-1,4-dioxa-7-azaspiro[4.4]nonane |
| 225 | 6,9-dimethyl-1,4-dioxa-7-azaspiro[4.4]nonane |
| 226 | 8,9-dimethyl-1,4-dioxa-7-azaspiro[4.4]nonane |
| 227 | 6-fluoro-1,4-dioxa-7-azaspiro[4.4]nonane |
| 228 | 9-fluoromethyl-1,4-dioxa-7-azaspiro[4.4]nonane |
| 229 | 2-ethyl-8-(N-phenylalanyl)-1,4-dioxa-7-azaspiro[4.4]nonane |
| 230 | 2-ethyl-8-(N-valylaminomethyl)-1,4-dioxa-7-azaspiro[4.4]nonane |
| 231 | 9-(N-isoleucyl-valylaminomethyl)-1,4-dioxa-7-azaspiro[4.4]nonane |
| 232 | 9-(N-alanyl-norvalylaminomethyl)-1,4-dioxa-7-azaspiro[4.4]nonane |
| 233 | 9-(N-valyl-tyrosylaminomethyl)-1,4-dioxa-7-azaspiro[4.4]nonane |
| *234 | 10-amino-1,5-dioxa-8-azaspiro[5.4]decane |
| *235 | 4-aminomethyl-1,5-dioxa-8-azaspiro[5.4]decane |
| *236 | 10-aminomethyl-1,5-dioxa-8-azaprio[5.4]decane |
| *237 | 3-amino-4-methyl-1,5-dioxa-8-azaspiro[5.4]decane |
| 238 | 3-chloro-1,5-dioxa-8-azaspiro[5.4]decane |
| 239 | 4-ethyl-1,5-dioxa-8-azaspiro[5.4]decane |
| 240 | 10-fluoromethyl-1,5-dioxa-8-azaspiro[5.4]decane |
| 241 | 10-methyl-1,5-dioxa-8-azaspiro[5.4]decane |
| 242 | 3-N-(valylamino)-1,5-dioxa-8-azaspiro[5.4]decane |
| 243 | 4-N-(isoleucyl-alanylaminomethyl)-1,5-dioxa-87-azaspiro[5.4]-decane |
| *244 | 6-amino-1,4-dioxa-8-azaspiro[4.5]decane |
| *245 | 6-aminomethyl-1,4-dioxa-8-azaspiro[4.5]decane |
| *246 | 3-aminomethyl-6-methyl-1,4-dioxa-8-azaspiro[ 4.5]decane |
| 247 | 2,6-dimethyl-1,4-dioxa-8-azaspiro[4.5]decane |
| 248 | 3-N,N-dimethylaminomethyl-1,4-dioxa-8-azaspiro[4.5]decane |
| 249 | 3-ethyl-1,4-dioxa-8-azaspiro[4.5]decane |
| 250 | 6-fluoromethyl-1,4-dioxa-8-azaspiro[4.5]decane |
| 251 | 6-methyl-1,4-dioxa-8-azaspiro[4.5]decane |
| 252 | 3-(N-valylaminomethyl)-1,4-dioxa-8-azaspiro[4.5]decane |
| 253 | 3-(N-leucyl-isoleucylaminomethyl)-1,4-dioxa-8-azaspiro[4.5]-decane |
| *254 | 7-amino-1,5-dioxa-9-azaspiro[5.5]undecane |
| *255 | 2-aminomethyl-1,5-dioxa-9-azaspiro[5.5]undecane |
| *256 | 3-aminomethyl-1,5-dioxa-9-azaspiro[5.5]undecane |
| *257 | 8-aminomethyl-1,5-dioxa-9-azaspiro[5.5]undecane |
| 258 | 2-ethyl-7-methyl-1,5-dioxa-9-azaspiro[5.5]undecane |
| 259 | 2-methyl-1,5-dioxa-9-azaspiro[5.5]undecane |
| 260 | 7-methyl-1,5-dioxa-9-azaspiro[5.5]undecane |
| 261 | 3-(N-leucylamino)-1,5-dioxa-9-azaspiro[5.5]undecane |
| 262 | 2-(N-leucylaminomethyl)-1,5-dioxa-9-azaspiro[5.5]-undecane |
| 263 | 3-(N-alanyl-tyrosylamino)-1,5-dioxa-9-azaspiro[5.5]undecane |
| *264 | 3-amino-1,5-dioxa-8-azaspiro[5.5]undecane |
| *265 | 10-amino-1,5-dioxa-8-azaspiro[5.5]undecane |
| *266 | 2-aminomethyl-1,5-dioxa-8-azaspiro[5.5]undecane |
| *267 | 10-aminomethyl-1,5-dioxa-8-azaspiro[5.5]undecane |
| *268 | 11-aminomethyl-1,5-dioxa-8-azaspiro[5.5]undecane |
| 269 | 10-methyl-1,5-dioxa-8-azaspiro[5.5]undecane |
| 270 | 11-methyl-1,5-dioxa-8-azaspiro[5.5]undecane |
| 271 | 3-(N-valylamino)-1,5-dioxa-8-azaspiro[5.5]undecane |
| 272 | 10-(N-valylamino)-1,5-dioxa-8-azaspiro[5.5]undecane |
| 273 | 3-(N-isoleucyl-valylamino)-1,5-dioxa-8-azaspiro[5.5]-undecane |

*Non-ring amino groups are protected and deprotected as in Example 159.

EXAMPLE 274

1-Cyclopropyl-6,8-difluoro-7-(9-amino-1,4-dioxa-7-azaspiro[4.4]non-7-yl)-1,4-dihydro-4-oxo-3-quinolinecarboxylic acid Step 1: 1-Cyclopropyl-6,8-difluoro-7-(9-amino-1,4-dioxa-7-azaspiro[4.4]non-7-yl)-1,4-dihydro-4-oxo-3-quinolinecarboxylic acid ethyl ester Following the procedure of Step 1 Example 80, starting with 0.750 g (2.4 mmol) of 1-cyclopropyl-6,7,8-trifluoro-1,4-dihydro-4-oxo-3-quinolinecarboxylic acid ethyl ester and substituting 0.521 g (3.6 mmol) of 9-amino-1,4-dioxa-7-azaspiro[4.4]nonane, from Step 6 Example 208, for the spiro compound of that example, and heating at 40° C. instead of 65° C. for 288 hours instead of 48 hours, the crude product was obtained. The compound was dissolved in methylene chloride which was washed with 2×100 mL of water then dried over anhydrous sodium sulfate, then the solvent was removed by evaporation under vacuum. The product was purified with HPLC, eluting with 60% increasing to 65% methanol/water. The solvent was removed by evaporation under vacuum to afford 0.466 g of the title compound, NMR (CDCl$_3$) d 1.12 (m, 4H), 1.40 (t, 3H, J=7.5 Hz), 3.45 (m, 5H), 3.62 (m, 1H), 3.78 (m, 2H), 3.84 (m, 1H), 3.98 (m, 1H), 4.07 (m, 4H), 4.38 (q, 2H, J=7.5 Hz), 7.83 (dd, 1H, J=15, 1.5 Hz), 8.50 (s, 1H).

Step 2. 1-Cyclopropyl-6,8-difluoro-7-(9-amino-1,4-dioxa-7-azaspiro[4.4]non-7-yl)-1,4-dihydro-4-oxo-3-quinolinecarboxylic acid The ester from Step 1 was hydrolyzed via the procedure of Step 7 Example 208. The solution was poured into 25 mL of water, conc. HCl added to adjust the solution to pH 1, and the water removed under vacuum. The crude product was stirred with 80 mL of 1:1 methanol/methylene chloride for 2 hours and the insoluble salts filtered off. The filtrate was evaporated to dryness to afford 0.444 g of the title compound as the hydrochloride salt., mp 224°–226° C., MS (DCI) M/Z 408 (M+H); NMR (TFA/AA) d 1.49 (m, 4H), 4.0–4.62 (m, 12H), 8.04 (d, 1H, J=13.5), 9.26 (s, 1H). Analysis calculated for $C_{19}H_{20}ClF_2N_3O_5 \cdot 1.5 H_2O$: C, 48.47; H, 4.92; N, 8.92. Found: C, 48.23; H, 4.67; N, 8.61.

EXAMPLE 275

(R)-10-(1,4-Dioxa-2-methyl-7-azaspiro[4.4]non-7-yl)-9,10-difluoro-2,3-dihydro-3-methyl-7-oxo-7H-pyrido[1,2,3-de]-1,4-benzoxazine-6-carboxylic acid Into oven-dried glassware maintained under dry N$_2$ were placed 1.6 g (11.2 mmol) of 1,4-dioxa-2-methyl-7-azaspiro[4.4]nonane, from Step 2 Example 135, 50 mL of pyridine, 0.8 g of triethylamine and 1.05 g (3.7 mmol) of (R)-9, 10-difluoro-2,3-dihydro-3-methyl-7-oxo-7H-pyrido[1,2,3-de]-1,4-benzoxazine-6-carboxylic acid (preparation described by L. A. Mitscher, et al., J. Med. Chem., 30, 2283–86, 1987), and the reaction mixture was heated at 80° C. with stirring for 9 hours. The solvent was evaporated, and the residue was triturated with 50 mL of water to remove impurities. The solid was further washed with 10 mL of methanol, filtered and dried to afford 1.27 g of the title product, mp 248°–251° C.; MS M/Z 405 (M+H); NMR (CDCl$_3$) d 1.33 (dd, 3H), 1.58 (t, 5H), 2.10 (m, 2H), 3.50 (m, 1H), 3.85 (m, 2H), 4.11 (m, 2H), 7.69 (d, 1H), 8.53 (s, 1H), 15.16 (s, 1H). Analysis calculated for $C_{20}H_{21}FN_2O_6$: C, 59.40; H, 5.23; N, 6.93. Found: C, 59.43; H, 5.35; N, 6.96.

EXAMPLES 276–329

By following the procedures describes in Example 275 and replacing 1,5-dioxa-2-methyl-7-azaspiro[4.4]-decane in Step 3 with the appropriate ketal compound, Examples 276–329 (in which R$^2$=H, R$^3$=H, R$^4$=F and R$^7$=CH$_3$) may be prepared as disclosed in Table 13.

TABLE 13

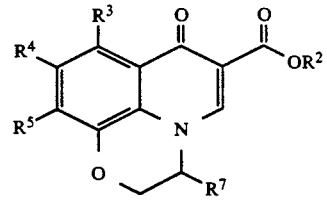

| Example # | R$^5$ is derived from ketal compound: |
|---|---|
| 276* | 2-aminomethyl-3,3-dimethoxypyrrolidine |
| *277 | 6-aminomethyl-1,4-dioxa-7-azaspiro[4.4]nonane |
| *278 | 8-aminomethyl-2-ethyl-1,4-dioxa-7-azaspiro[4.4]nonane |
| 279 | 9-chloro-1,4-dioxa-7-azaspiro[4.4]nonane |
| 280 | 2,3-dimethyl-1,4-dioxa-7-azaspiro[4.4]nonane |
| 281 | 6,9-dimethyl-1,4-dioxa-7-azaspiro[4.4]nonane |
| 282 | 8,9-dimethyl-1,4-dioxa-7-azaspiro[4.4]noane |
| 283 | 6-fluoro-1,4-dioxa-7-azaspiro[4.4]nonane |
| 284 | 9-fluoromethyl-1,4-dioxa-7-azaspiro[4.4]nonane |
| 285 | 2-ethyl-8-(N-phenylalanyl)-1,4-dioxa-7-azaspiro[4.4]-nonane |
| 286 | 2-ethyl-8-(N-valylaminomethyl)-1,4-dioxa-7-azaspiro[4.4]-nonane |
| 287 | 9-(N-isoleucyl-valylaminomethyl)-1,4-dioxa-7-azaspiro-[4.4]nonane |
| 288 | 9-(N-alanyl-norvalylaminomethyl)-1,4-dioxa-7-azaspiro-[4.4]nonane |
| 289 | 9-(N-valyl-tyrosylaminomethyl)-1,4-dioxa-7-azaspiro[4.4]-nonane |
| *290 | 10-amino-1,5-dioxa-8-azaspiro[5.4]decane |
| *291 | 4-aminomethyl-1,5-dioxa-8-azaspiro[5.4]decane |
| *292 | 10-aminomethyl-1,5-dioxa-8-azaspiro[5.4]decane |
| *293 | 3-amino-4-methyl-1,5-dioxa-8-azaspiro[5.4]decane |
| 294 | 3-chloro-1,5-dioxa-8-azaspiro[5.4]decane |
| 295 | 4-ethyl-1,5-dioxa-8-azaspiro[5.4]decane |
| 296 | 10-fluoromethyl-1,5-dioxa-8-azaspiro[5.4]decane |
| 297 | 10-methyl-1,5-dioxa-8-azaspiro[5.4]decane |
| 298 | 3-N-(valylamino)-1,5-dioxa-8-azaspiro[5.4]decane |
| 299 | 4-N-(isoleucyl-alanylaminomethyl)-1,5-dioxa-8-azaspiro-[5.4]decane |
| *300 | 6-amino-1,4-dioxa-8-azaspiro[ 4.5]decane |
| *301 | 6-aminomethyl-1,4-dioxa-8-azaspiro[4.5]decane |
| *302 | 3-aminomethyl-6-methyl-1,4-dioxa-8-azaspiro[4.5]decane |
| 303 | 2,6-dimethyl-1,4-dioxa-8-azaspiro[4.5]decane |
| 304 | 3-N,N-dimethylaminomethyl-1,4-dioxa-8-azaspiro[4.5]-decane |
| 305 | 3-ethyl-1,4-dioxa-8-azaspiro[4.5]decane |
| 306 | 6-fluoromethyl-1,4-dioxa-8-azaspiro[4.5]decane |
| 307 | 6-methyl-1,4-dioxa-8-azaspiro[4.5]decane |
| 308 | 3-(N-valylaminomethyl)-1,4-dioxa-8-azaspiro[4.5]decane |
| 309 | 3-(N-leucyl-isoleucylaminomethyl)-1,4-dioxa-8-azaspiro-[4.5]decane |
| *310 | 7-amino-1,5-dioxa-9-azaspiro[5.5]undecane |
| *311 | 2-aminomethyl-1,5-dioxa-9-azaspiro[5.5]undecane |
| *312 | 3-aminomethyl-1,5-dioxa-9-azaspiro[5.5]undecane |
| *313 | 8-aminomethyl-1,5-dioxa-9-azaspiro[5.5]undecane |
| 314 | 2-ethyl-7-methyl-1,5-dioxa-9-azaspiro[5.5]undecane |
| 315 | 2-methyl-1,5-dioxa-9-azaspiro[5.5]undecane |
| 316 | 7-methyl-1,5-dioxa-9-azaspiro[5.5]undecane |
| 317 | 3-(N-leucylamino)-1,5-dioxa-9-azaspiro[5.5]undecane |
| 318 | 2-(N-isoleucylaminomethyl)-1,5-dioxa-9-azaspiro[5.5]-undecane |
| 319 | 3-(N-alanyl-tyrosylamino)-1,5-dioxa-9-azaspiro[5.5]-undecane |
| *320 | 3-amino-1,5-dioxa-8-azaspiro[5.5]undecane |
| *321 | 10-amino-1,5-dioxa-8-azaspiro[5.5]undecane |
| *322 | 2-aminomethyl-1,5-dioxa-8-azaspiro[5.5]undecane |
| *323 | 10-aminomethyl-1,5-dioxa-8-azaspiro[5.5]undecane |
| *324 | 11-aminomethyl-1,5-dioxa-8-azaspiro[5.5]undecane |
| 325 | 10-methyl-1,5-dioxa-8-azaspiro[5.5]undecane |

TABLE 13-continued

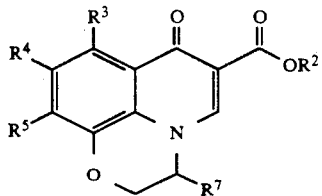

| Example # | $R^5$ is derived from ketal compound: |
|---|---|
| 326 | 11-methyl-1,5-dioxa-8-azaspiro[5.5]undecane |
| 327 | 3-(N-valylamino)-1,5-dioxa-8-azaspiro[5.5]undecane |
| 328 | 10-(N-valylamino)-1,5-dioxa-8-azaspiro[5.5]undecane |
| 329 | 3-(N-isoleucyl-valylamino)-1,5-dioxa-8-azaspiro[5.5]-undecane |

*Non-ring amino groups are protected and deprotected as in Example 159.

EXAMPLE 330

(R)-10-(1,5-Dioxa-9-azaspiro[5.5]undec-9-yl)-9,10-difluoro-2,3-dihydro-3-methyl-7-oxo-7H-pyrido[1,2,3-de]-1,4-benzoxazine-6-carboxylic acid Into oven-dried glassware maintained under dry $N_2$ were placed 0.785 g (5 mmol) of 1,5-dioxa-9-azaspiro[5.5]undecane, from Step 4 Example 196, 15 mL of dry pyridine, 0.700 mL of triethylamine, and 0.469 g (1.67 mmol) of (R)-9,10-difluoro-2,3-dihydro-3-methyl-7-oxo-7H-pyrido[1,2,3-de]-1,4-benzoxazine-6-carboxylic acid (see Example 275). The reaction mixture was heated at 80° C. with stirring for 72 hours. The solvent was evaporated, and the residue was triturated with 5 mL portions of water, dilute acetic acid (pH 3-4), and water again to remove impurities. The solid was further washed with 7 mL of methanol at reflux temperature for 2 hours. The product was filtered, washed with methanol and dried under vacuum to afford 0.590 g of the title compound, mp 274°-275° C.; MS (DCl/NH3) 419 (M+H); NMR (CDCl3) d 1.60 (d, 3H, J=6 Hz), 1.78 (quint, 2H, J=4.5 Hz), 2.04 (m, 4H), 3.38 (m, 4H), 3.95 (dd, 4H, J=6 Hz), 4.32-4.52 (m, 3H), 7.72 (d, 1H, J=12 Hz), 8.61 (s, 1H), 15.00 (s, 1H). Analysis calculated for $C_{21}H_{23}FN_2O_6 \cdot \frac{1}{4} H_2O$ C, 59.64; H, 5.60; N, 6.62 Found: C, 59.59; H, 5.51; N, 6.51.

EXAMPLE 331

1-(2,4-Difluorophenyl)-7-(3,3-dimethoxypyrrolidin-1-yl)-6-fluoro-1.8-naphthyridine-3-carboxylic acid Step 1. 3-(Dimethyl-t-butylsilyloxy)-pyrrolidine
a. N-Benzyl-3-(dimethyl-t-butylsilyloxy)-pyrrolidine. Into oven-dried glassware maintained under dry $N_2$ were placed 3.00 g (16.9 mmol) of N-benzyl-3-pyrrolidinol (commercially available) dissolved in 100 mL of methylene chloride, 2.81 g (18.7 mmol) of t-butyl-dimethylsilyl chloride, and 2.31 g (3.4 mmol) of imidazole, and the reaction was stirred at room temperature for 20 hours, another 1.16 g of imidazole was added, whereupon a solid precipitated, and the reaction was stirred for 4 hours more. The mixture was diluted with 100 mL of methylene chloride, which was washed with 2×250 mL of 5% sodium bicarbonate solution and once with water. The solvent was dried over anhydrous sodium sulfate, filtered and removed by evaporation under vacuum. The crude product was purified by column chromatography over silica gel, eluting with 0% increasing to 1% methanol/methylene chloride. The solvent was removed to afford 2.344 g of the title compound, MS (DCl) M/Z 292 (M+H); NMR (CDCl3) d 0.87 (s, 9H), 1.70 (m, 1H), 2.11 (dq, 1H, J=7.5, 13.5 Hz), 2.33 (dd, 1H, J=6.0, 12 Hz), 2.62 (m, 2H), 2.91 (dd, 1, J=6.0, 9.0), 3.63 (dd, 2H, J=13.5, 13.5 Hz), 4.39 (m, 1H), 7.32 (m, 5H).

b. 3-(Dimethyl-t-butysilyloxy)-pyrrolidine. A 2.34 g sample of the compound from Step 1 was dissolved in 100 mL of methanol, 1.17 g of 20% Pd/C (wet) was added and the hydrogenation run for 2 hours at room temperature under 4 atm of hydrogen. The catalyst was removed by filtration, and the solvent was removed under vacuum to afford 1.13 g of the title product, MS (DCl) M/Z 202 (M+H).

Step 2. 1-(2,4-Difluorophenyl)-7-(3-(dimethyl-t-butysilyloxy)-pyrrolidin-1-yl)-6-fluoro-1,8-naphthyridine-3-carboxylic acid ethyl ester Into oven-dried glassware maintained under dry $N_2$ were placed 3.00 g (7.8 mmol) of 1-(2,4-difluorophenyl)-7-chloro-6-fluoro-1,8-naphthyridine-3-carboxylic acid ethyl ester (preparation described by D. T. W. Chu, et al., J. Med. Chem. 1986, 2363-2369), 2.37 g (11.8 mmol) of the protected pyrrolidinol from Step 1, 2.2 mL of triethylamine and 40 mL of dry pyridine. The reaction was stirred at room temperature for 2.5 hours, then the solvent was removed, and the product was washed with ethanol and hexane, then filtered and dried to afford 6.966 g of the title product, which was immediately taken to the next step.

Step 3. 1-(2,4-Difluorophenyl)-7-(3-hydroxypyrrolidin-1-yl)-6-fluoro-1,8-naphthyridine-3-carboxylic acid ethyl ester The 6.966 g of the compound from Step 2 was dissolved in 55 mL of dry THF, 38 mL of 1M (n-butyl)4NF in THF was added and the solution stirred at room temperature for 4 hours. The solvent was evaporated and the product crystallized from i-propanol/hexane to afford 2.856 g of the title compound as a yellow solid. This material was also taken directly to the next step.

Step 4. 1-(2,4-Difluorophenyl)-7-(3-oxopyrrolidin-1-yl)-6-fluoro-1,8-naphthyridine-3-carboxylic acid ethyl ester To 0.8 mL of oxalyl chloride dissolved in 25 mL dry methylene chloride cooled to −70° C. was added 1.1 mL of DMSO dropwise over a 20 min period with stirring. After stirring for another 20 min, 2.85 g (6.5 mmol) of the compound from Step 3 suspended in 25 mL of methylene chloride was added dropwise over 30 min, and the reaction mixture stirred for 4 hours. Then 4.6 mL of triethylamine was added dropwise, and the reaction mixture was allowed to warm to room temperature. The solvent was removed under vacuum, water added, and the crude product filtered off and dried. The product was separated from starting material by column chromatography over silica gel to afford 0.42 g of the title compound.

Step 5. 1-(2,4-Difluorophenyl)-7-(3,3-dimethoxypyrrolidin-1-yl)-6-fluoro-1,8-naphthyridine-3-carboxylic acid ethyl ester A 0.400 g (0.9 mmol) sample of the compound from Step 4 was dissolved in 3 mL of methanol, 3 mL of trimethylorthoformate and 9 mg of p-toluenesulfonic acid was added, and the solution heated at 60° C. for 24 hours. The reaction contents were poured into a 5% sodium bicarbonate solution, and the product was extracted (3×) into methylene chloride which was dried over sodium sulfate, filtered and evaporated to dryness. The crude product was recrystallized from ethanol/- hexane to afford 0.347 g of the title compound as a light yellow solid, MS M/Z 478 (M).

Step 6. 1-(2,4-Difluorophenyl)-7-(3,3-dimethoxypyrrolidin-1-yl)-6-fluoro-1,8-naphthyridine-3-carboxylic acid A 0.347 g (0.73 mmol) sample of the compound from the previous step was suspended in 2 mL of THF, 3.6 mL of 1.0M NaOH added and the mixture heated at 45° C. for 6 hours, then at 70° C. without the condenser for 2 hours to distill off the THF. The residue was poured into water, which was then adjusted to pH 6–7 with acetic acid, and the product was filtered off. This afforded 0.140 g of the title compound after drying, mp 205°–206° C.; MS (DCI) M/Z 450 (M+H), 405 (M—COOH); NMR (CDCl$_3$) d 2.10 (m, 2H), 3.24 (s, 6H), 3.90 (m, 2H), 4.54 (s 2H), 7.19 (m, 2H), 7.53 (m, 1H), 8.04 (d, 1H, J=13.5 Hz), 8.71 (s, 1H). Analysis calculated for $C_{21}H_{18}F_3N_3O_5 \cdot 1.5$ H$_2$O: C, 55.47; H, 4.87; N, 8.82. Found: C, 55.77; H, 4.10; N.9.28.

EXAMPLE 332

1-(2,4-difluorophenyl)-7-(1,5-dioxa-8-azaspiro[5.4]dec-8-yl)-6-fluoro-1,8-naphthyridine-3-carboxylic acid Step 1. 1-(2,4-difluorophenyl)-7-(1,5-dioxa-8-azaspiro[5.4]dec-8-yl)-6-fluoro-1,8-naphthyridine-3-carboxylic acid ethyl ester Following the procedure of Step 2 Example 331 a 0.168 g (1.17 mmol) of 1,5-dioxa-8-azaspiro[5.4]decane, from Step 2 Example 14, was reacted with 0.300 g (0.78 mmol) of 1-(2,4-difluorophenyl)-7-chloro-6-fluoro-1,8-naphthyridine-3-carboxylic acid ethyl ester by heating at 40° C. instead of 45° C. for 10 instead of 24 hours. The solvent was removed by evaporation to afford the title product which was purified by column chromatography over silica gel (0% increasing to 4% methanol/methylene chloride) to afford 0.252 g of the title compound. The ester was not further purified, but was taken directly to the next step.

Step 2. 1-(2,4-difluorophenyl)-7-(1,5-dioxa-8-azaspiro[5.4]dec-8-yl)-6-fluoro-1,8-naphthyridine-3-carboxylic acid The 0.252 g of the ester from the previous step was dissolved in 5 mL of THF and 5.2 mL of 1M NaOH was added and the reaction was heated at 50° C. for 4 hours, then at 85° C. for 1.5 hours without the condenser to distill off the THF. The residue was poured into water, which was then adjusted to pH 4 with acetic acid, and the product was filtered off. This material was washed with water and dried to afford 0.132 g of the title compound as a light yellow solid, mp 145°–146° C.; MS(FAB) M/Z 462 (M+H), 444 (M+H-H$_2$O). NMR (TFA/AA) d 3.93 (m, 2H), 4.06 (m, 2H), 4.31 (M, 2H), 4.54 (m, 6H), 7.25 (m, 2H), 7.67 (m, 1H), 8.24 (d, 1H, J=12.0 Hz), 9.21 (s, 1). Analysis calculated for $C_{22}H_{18}F_3N_3O_5 \cdot H_2O$: C, 55.12; H, 4.20; N, 8.76. Found: C, 55.57; H, 3.93; N, 8.69.

EXAMPLES 333–386

By following the procedures described in Example 332 and replacing 1,5-dioxa-8-azaspiro[5.4]decane in Step 1 with the appropriate ketal compound, Examples 333–386 (in which A=N and R$^1$=2,4-difluorophenyl) may be prepared as disclosed in Table 14.

TABLE 14

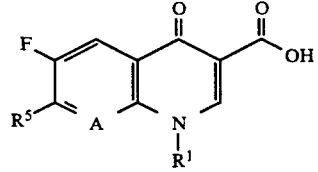

| Example # | R$^5$ is derived from ketal compound: |
|---|---|
| 333* | 2-aminomethyl-3,3-dimethoxypyrrolidine |
| *334 | 6-aminomethyl-1,4-dioxa-7-azaspiro[4.4]nonane |
| *335 | 8-aminomethyl-2-ethyl-1,4-dioxa-7-azaspiro[4.4]nonane |
| 336 | 9-chloro-1,4-dioxa-7-azaspiro[4.4]nonane |
| 337 | 2,3-dimethyl-1,4-dioxa-7-azaspiro[4.4]nonane |
| 338 | 6,9-dimethyl-1,4-dioxa-7-azaspiro[4.4]nonane |
| 339 | 8,9-dimethyl-1,4-dioxa-7-azaspiro[4.4]nonane |
| 340 | 6-fluoro-1,4-dioxa-7-azaspiro[4.4]nonane |
| 341 | 9-fluoromethyl-1,4-dioxa-7-azaspiro[4.4]nonane |
| 342 | 2-ethyl-8-(N-phenylalanyl)-1,4-dioxa-7-azaspiro[4.4]nonane |
| 343 | 2-ethyl-8-(N-valylaminomethyl)-1,4-dioxa-7-azaspiro[4.4]nonane |
| 344 | 9-(N-isoleucyl-valylaminomethyl)-1,4-dioxa-7-azaspiro[4.4]nonane |
| 345 | 9-(N-alanyl-norvalylaminomethyl)-1,4-dioxa-7-azaspiro[4.4]nonane |
| 346 | 9-(N-valyl-tyrosylaminomethyl)-1,4-dioxa-7-azaspiro[4.4]nonane |
| *347 | 10-amino-1,5-dioxa-8-azaspiro[5.4]decane |
| *348 | 4-aminomethyl-1,5-dioxa-8-azaspiro[5.4]decane |
| *349 | 10-aminomethyl-1,5-dioxa-8-azaspiro[5.4]decane |
| *350 | 3-amino-4-methyl-1,5-dioxa-8-azaspiro[5.4]decane |
| 351 | 3-chloro-1,5-dioxa-8-azaspiro[5.4]decane |
| 352 | 4-ethyl-1,5-dioxa-8-azaspiro[5.4]decane |
| 353 | 10-fluoromethyl-1,5-dioxa-8-azaspiro[5.4]decane |
| 354 | 10-methyl-1,5-dioxa-8-azaspiro[5.4]decane |
| 355 | 3-N-(valylamino)-1,5-dioxa-8-azaspiro[5.4]decane |
| 356 | 4-N-(isoleucyl-alanylaminomethyl)-1,5-dioxa-8-azaspiro[5.4]decane |
| *357 | 6-amino-1,4-dioxa-8-azaspiro[4.5]decane |
| *358 | 6-aminomethyl-1,4-dioxa-8-azaspiro[4.5] decane |
| *359 | 3-aminomethyl-6-methyl-1,4-dioxa-8-azaspiro[4.5]decane |
| 360 | 2,6-dimethyl-1,4-dioxa-8-azaspiro[4.5]decane |
| 361 | 3-N,N-dimethylaminomethyl-1,4-dioxa-8-azaspiro[4.5]decane |
| 362 | 3-ethyl-1,4-dioxa-8-azaspiro[4.5]decane |
| 363 | 6-fluoromethyl-1,4-dioxa-8-azaspiro[4.5]decane |
| 364 | 6-methyl-1,4-dioxa-8-azaspiro[4.5]decane |
| 365 | 3-(N-valylaminomethyl)-1,4-dioxa-8-azaspiro[4.5]decane |
| 366 | 3-(N-leucyl-isoleucylaminomethyl)-1,4-dioxa-8-azaspiro-[4.5]decane |
| *367 | 7-amino-1,5-dioxa-9-azaspiro[5.5]undecane |
| *368 | 2-aminomethyl-1,5-dioxa-9-azaspiro[5.5]undecane |
| *369 | 3-aminomethyl-1,5-dioxa-9-azaspiro[5.5]undecane |
| *370 | 8-aminomethyl-1,5-dioxa-9-azaspiro[5.5]undecane |
| 371 | 2-ethyl-7-methyl-1,5-dioxa-9-azaspiro[5.5]undecane |
| 372 | 2-methyl-1,5-dioxa-9-azaspiro[5.5]undecane |
| 373 | 7-methyl-1,5-dioxa-9-azaspiro[5.5]undecane |
| 374 | 3-(N-leucylamino)-1,5-dioxa-9-azaspiro[5.5]undecane |
| 375 | 2-(N-isoleucylaminomethyl)-1,5-dioxa-9-azaspiro[5.5]undecane |
| 376 | 3-(N-alanyl-tyrosylamino)-1,5-dioxa-9-azaspiro[5.5]undecane |
| *377 | 3-amino-1,5-dioxa-8-azaspiro[5.5]undecane |
| *378 | 10-amino-1,5-dioxa-8-azaspiro[5.5]undecane |
| *379 | 2-aminomethyl-1,5-dioxa-8-azaspiro[5.5]undecane |
| *380 | 10-aminomethyl-1,5-dioxa-8-azaspiro[5.5]undecane |
| *381 | 11-aminomethyl-1,5-dioxa-8-azaspiro[5.5]undecane |
| 382 | 10-methyl-1,5-dioxa-8-azaspiro[5.5]undecane |
| 383 | 11-methyl-1,5-dioxa-8-azaspiro[5.5]undecane |
| 384 | 3-(N-valylamino)-1,5-dioxa-8-azaspiro[5.5]undecane |
| 385 | 10-(N-valylamino)-1,5-dioxa-8-azaspiro[5.5]undecane |
| 386 | 3-(N-isoleucyl-valylamino)-1,5-dioxa-8-azaspiro[5.5]-undecane |

*Non-ring amino groups are protected and deprotected as in Example 159.

EXAMPLE 387

1-(2,4-difluorophenyl)-7-(1,4-dioxa-2-methyl-7-azaspiro[4.4]non-7-yl)-6-fluoro-1,8-naphthyridine-3-carboxylic acid Step 1. 1-(2,4-difluorophenyl)-7-(1,4-dioxa-2-methyl-7-azaspiro[4.4]non-7-yl)-6-fluoro-1,8-naphthyridine-3-carboxylic acid ethyl ester In a reaction similar to that of Step 2 Example 331, into oven-dried glassware maintained under dry $N_2$ were placed 0.423 g (3.0 mmol) of 1,4-dioxa-2-methyl-7-azaspiro[4.4]nonane, from Step 2 Example 135, and 0.382 g (1.0 mmol) of 1-(2,4-difluorophenyl)-7-chloro-6-fluoro-1,8-naphthyridine-3-carboxylic acid ethyl ester dissolved in 7 mL of pyridine. The reaction was stirred at room temperature for 24 hours, then the solvent was removed in a rotary evaporator. The residue was dissolved in 60 mL of methylene chloride, washed with 2×50 mL of water and dried over anhydrous sodium sulfate and filtered. The solvent was removed by evaporation and the product was purified by recrystallization from ethanol/water to afford after drying 0.407 g of the title compound. This material was taken directly to the next step.

Step 2. 1-(2,4-difluorophenyl)-7-(1,4-dioxa-2-methyl-7-azaspiro[4.4]non-7-yl)-6-fluoro-1,8-naphthyridine-3-carboxylic acid A 0.404 g (0.83 mmol) sample of the ester from the previous step was dissolved in 5 mL of THF, 5 mL of 1M NaOH was added and the reaction was heated at 65° C. for 1 hours, then at 85° C. for 2 hours without the condenser to distill off the THF. The residue was poured into water, which was then adjusted to pH 4 with acetic acid, and the product was filtered off. This material was washed with 2×50 mL of water and dried. Next the product was suspended in 7 mL of ethanol and heated under reflux with stirring for 1 hours, filtered, washed with 2×3 mL of ethanol and dried under vacuum to afford 0.71 g of the title compound as a white solid, mp 209°–210° C.; MS (DCl/NH$_3$) M/Z 462 (M+H), 418 (M—CO$_2$). NMR (CDCl$_3$) d 1.33 (d, 3H, J=4.5 Hz), 2.05 (m, 2H), 3.40 (m, 2H), 3.45 (dd, 2H, J=7.5, 16 Hz), 4.08 (m, 2H), 4.25 (m, 1H), 7.05 (m, 2H), 7.48 (m, 1H), 8.05 (d, 1H, J=16 Hz), 8.63 (s, 1H), 15.01 (s, 1H). Analysis calculated for $C_{22}H_{18}F_3N_3O_5$: C, 57.27; H, 3.93; N, .9.10 Found: C, 57.16; H, 3.96; N, 9.06.

Example 388

7-(1,4-dioxa-2-methyl-7-azaspiro[4.4]non-7-yl)-6-fluoro-1-(4-fluorophenyl)-1,8-naphthyridine-3-carboxylic acid Step 1. 7-(1,4-dioxa-2-hydroxymethyl-7-azaspiro[4.4]non-7-yl)-6-fluoro-1-(4-fluorophenyl)-1,8-naphthyridine-3-carboxylic acid ethyl ester In a reaction similar to that of Step 1 Example 387, into oven-dried glassware maintained under dry $N_2$ were placed 0.500 g (3.1 mmol) of 1,4-dioxa-2-hydroxymethyl-7-azaspiro[4.4]nonane, from Step 2 Example 147, 0.364 g (1.0 mmol) of 7-chloro-6-fluoro-1-(4-fluorophenyl)-1,8-naphthyridine-3-carboxylic acid ethyl ester (preparation described by D. T. W. Chu, et. al., J. Med. Chem. 1986, 2363–2369), and 7 mL of dry pyridine. The reaction was stirred at room temperature for 3 hours, then the solvent was removed in a rotary evaporator. The residue was dissolved in 60 mL of methylene chloride, washed with 60 mL of water which was re-extracted with 60 mL of methylene chloride. The combined organic solvent was washed with 120 mL of 0.5N HCl, 120 mL of 5% NaHCO$_3$, dried over anhydrous sodium sulfate and the solvent was removed by evaporation under vacuuum to afford 0.464 g of the title compound.

Step 2. 7-(1,4-dioxa-2-hydroxymethyl-7-azaspiro[4.4]non-7-yl)-6-fluoro-1-(4-fluorophenyl)-1,8-naphthyridine-3-carboxylic acid A 0.460 g (0.94 mmol) sample of the ester from Step 1 was hydrolyzed and the product isolated by a procedure similar to that in Step 2 Example 387. The title compound (0.345 g) was obtained as a white solid, mp 225°–227° C.; MS (DCl/NH$_3$) M/Z 460 (M+H), 416 (M+H-CO$_2$). NMR (CDCl$_3$) d 2.10 (m, 2H), 3.66–3.90 (m, 6H), 4.10 (m, 2H), 4.30 (m, 1H), 7.33 (dd, 2H, J=9 Hz), 7.60 (m, 2H), 8.14 (d, 1H, J=13 Hz), 8.87 (s, 1H). Analysis calculated for $C_{22}H_{19}F_2N_3O_6 \cdot 1.25$ H$_2$O: C, 54.83; H, 4.50; N, 8.72. Found: C, 54.42; H, 4.03; N, 8.57.

EXAMPLES 389–442

By following the procedures described in Example 388 and replacing 2-hydroxymethyl-1,4-dioxa-7-azaspiro[4.4]nonane in Step 1 with the appropriate ketal compound, Examples 389–442 (in which A=N and R$^1$=4-fluorophenyl) may be prepared as disclosed in Table 15.

TABLE 15

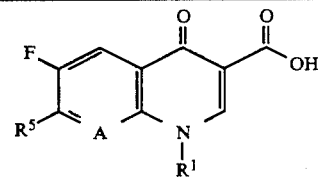

| Example # | R$^5$ is derived from ketal compound: |
|---|---|
| 389* | 2-aminomethyl-3,3-dimethoxypyrrolidine |
| *390 | 6-aminomethyl-1,4-dioxa-7-azaspiro[4.4]nonane |
| *391 | 8-aminomethyl-2-ethyl-1,4-dioxa-7-azaspiro[4.4]nonane |
| 392 | 9-chloro-1,4-dioxa-7-azaspiro[4.4]nonane |
| 393 | 2,3-dimethyl-1,4-dioxa-7-azaspiro[4.4]nonane |
| 394 | 6,9-dimethyl-1,4-dioxa-7-azaspiro[4.4]nonane |
| 395 | 8,9-dimethyl-1,4-dioxa-7-azaspiro[4.4]nonane |
| 396 | 6-fluoro-1,4-dioxa-7-azaspiro[4.4]nonane |
| 397 | 9-fluoromethyl-1,4-dioxa-7-azaspiro[4.4]nonane |
| 398 | 2-ethyl-8-(N-phenylalanyl)-1,4-dioxa-7-azaspiro[4.4]nonane |
| 399 | 2-ethyl-8-(N-valylaminomethyl)-1,4-dioxa-7-azaspiro[4.4]nonane |
| 400 | 9-(N-isoleucyl-valylaminomethyl)-1,4-dioxa-7-azaspiro[4.4]nonane |
| 401 | 9-(N-alanyl-norvalylaminomethyl)-1,4-dioxa-7-azaspiro[4.4]nonane |
| 402 | 9-(N-valyl-tyrosylaminomethyl)-1,4-dioxa-7-azaspiro[4.4]nonane |
| *403 | 10-amino-1,5-dioxa-8-azaspiro[5.4]decane |
| *404 | 4-aminomethyl-1,5-dioxa-8-azaspiro[5.4]decane |
| *405 | 10-aminomethyl-1,5-dioxa-8-azaspiro[5.4]decane |
| *406 | 3-amino-4-methyl-1,5-dioxa-8-azaspiro[5.4]decane |
| 407 | 3-chloro-1,5-dioxa-8-[5.4]decane |
| 408 | 4-ethyl-1,5-dioxa-8-azaspiro[5.4]decane |
| 409 | 10-fluoromethyl-1,5-dioxa-8-azaspiro[5.4]decane |
| 410 | 10-methyl-1,5-dioxa-8-azaspiro[5.4]decane |
| 411 | 3-N-(valylamino)-1,5-dioxa-8-azaspiro[5.4]decane |
| 412 | 4-N-(isoleucyl-alanylaminomethyl)-1,5-dioxa-8-azaspiro[5.4]decane |
| *413 | 6-amino-1,4-dioxa-8-azaspiro[4.5]decane |
| *414 | 6-aminomethyl-1,4-dioxa-8-azaspiro[4.5]decane |
| *415 | 3-aminomethyl-6-methyl-1,4-dioxa-8-azaspiro[4.5]decane |
| 416 | 2,6-dimethyl-1,4-dioxa-8-azaspiro[4.5]decane |
| 417 | 3-N,N-dimethylaminomethyl-1,4-dioxa-8-azaspiro[4.5]decane |
| 418 | 3-ethyl-1,4-dioxa-8-azaspiro[4.5]decane |
| 419 | 6-fluoromethyl-1,4-dioxa-8-azaspiro[4.5]decane |
| 420 | 6-methyl-1,4-dioxa-8-azaspiro[4.5]decane |

TABLE 15-continued

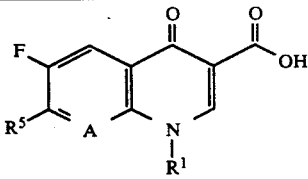

| Example # | $R^5$ is derived from ketal compound: |
|---|---|
| 421 | 3-(N-valylaminomethyl)-1,4-dioxa-8-azaspiro[4.5]decane |
| 422 | 3-(N-leucyl-isoleucylaminomethyl)-1,4-dioxa-8-azaspiro-decane |
| *423 | 7-amino-1,5-dioxa-9-azaspiro[5.5]undecane |
| *424 | 2-aminomethyl-1,5-dioxa-9-azaspiro[5.5]undecane |
| *425 | 3-aminomethyl-1,5-dioxa-9-azaspiro[5.5]undecane |
| *426 | 8-aminomethyl-1,5-dioxa-9-azaspiro[5.5]undecane |
| 427 | 2-ethyl-7-methyl-1,5-dioxa-9-azaspiro[5.5]undecane |
| 428 | 2-methyl-1,5-dioxa-9-azaspiro[5.5]undecane |
| 429 | 7-methyl-1,5-dioxa-9-azaspiro[5.5]undecane |
| 430 | 3-(N-leucylamino)-1,5-dioxa-9-azaspiro[5.5]undecane |
| 431 | 2-(N-isoleucylaminomethyl)-1,5-dioxa-9-azaspiro[5.5]-undecane |
| 432 | 3-(N-alanyl-tyrosylamino)-1,5-dioxa-9-azaspiro[5.5]-undecane |
| *433 | 3-amino-1,5-dioxa-8-azaspiro[5.5]undecane |
| *434 | 10-amino-1,5-dioxa-8-azaspiro[5.5]undecane |
| *435 | 2-aminomethyl-1,5-dioxa-8-azaspiro[5.5]undecane |
| *436 | 10-aminomethyl-1,5-dioxa-8-azaspiro[5.5]undecane |
| *437 | 11-aminomethyl-1,5-dioxa-8-azaspiro[5.5]undecane |
| 438 | 10-methyl-1,5-dioxa-8-azaspiro[5.5]undecane |
| 439 | 11-methyl-1,5-dioxa-8-azaspiro[5.5]undecane |
| 440 | 3-(N-valylamino)-1,5-dioxa-8-azaspiro[5.5]undecane |
| 441 | 10-(N-valylamino)-1,5-dioxa-8-azaspiro[5.5]undecane |
| 442 | 3-(N-isoleucyl-valylamino)-1,5-dioxa-8-azaspiro[5.5]-undecane |

*Non-ring amino groups are protected and deprotected as in Example 159.

EXAMPLE 443

7-(2-aminomethyl-1,4-dioxa-7-azaspiro[4.4]non-7-yl)-6-fluoro-1-(2,4-difluorophenyl)-1,8-naphthyridine-3-carboxylic acid dihydrochloride Step 1. 7-(2-t-butoxycarbonylaminomethyl-1,4-dioxa-7-azaspiro[4.4]non-7-yl)-6-fluoro-1-(2,4-difluorophenyl)-1,8-naphthyridine-3-carboxylic acid ethyl ester In a reaction similar to that of Step 1 Example 387, into oven-dried glassware maintained under dry $N_2$ were placed 0.733 g (2.8 mmol) of 2-t-butoxycarbonylaminomethyl-1,4-dioxa-7-azaspiro[4.4]nonane, from Step 5 Example 159, 0.725 g (1.9 mmol) of 1-(2,4-difluorophenyl)-7-chloro-6-fluoro-1,8-naphthyridine-3-carboxylic acid ethyl ester dissolved in 20 mL of pyridine and 1.06 mL (7.6 mmol) of triethylamine. The reaction was stirred at 45° C. for 6 hours, then the solvent was removed in a rotary evaporator after toluene was added to azeotrope the pyridine. The residue was dissolved in 60 mL of methylene chloride, washed with 2×50 mL of water and dried over anhydrous sodium sulfate and filtered. The solvent was removed by evaporation and the product was washed with hexane and dried to afford 1.184 g of the title compound, MS (DCI) M/Z 605 (M+H). NMR (CDCl$_3$) d 1.40 (t, 3H, J=6 Hz), 1.47 (s, 9H), 2.03 (m, 2H), 3.16 (m, 2H), 3.51 (m, 4H), 3.69 (m, 1H), 4.04 (m, 1H), 4.22 (m, 1H), 4.38 (q, 2H, J=6 Hz), 4.81 (m, 1H), 7.05 (m, 2H), 7.38 (m, 1H), 8.09 (dd, 1H, J=12, 1.5 Hz), 8.39 (d, 1H, J=1.5 Hz).

Step 2. 7-(2-aminomethyl-1,4-dioxa-7-azaspiro[4.4]non-7-yl)-6-fluoro-1-(2,4-difluorophenyl)-1,8-naphthyridine-3-carboxylic acid ethyl ester The 1.184 g of the boc-protected compound from Step 1 was deprotected and the product was isolated by a reaction similar to that in Step 7 Example 159, to afford 0.788 g of the title compound, which was taken directly to the next step.

Step 3. 7-(2-aminomethyl-1,4-dioxa-7-azaspiro[4.4]non-7-yl)-6-fluoro-1-(2,4-difluorophenyl)-1,8-naphthyridine-3-carboxylic acid dihydrochloride The 0.788 g of the ester from Step 2 was hydrolyzed by the procedure of Step 2 Example 387. The residue was poured into 20 mL of water and conc. HCl was added to adjust the acidity to pH 1-2. The product was filtered off, washed with water and dried to afford 0.446 g of the title compound, mp 188°-189° C.; MS (FAB) M/Z 477 (M+H), 459 (M+H-H$_2$O). NMR (TFA/AA) d 2.20 (m, 2H), 3.48 (m, 4H), 4.12 (m, 4H), 4.68 (m, 1H), 7.24 (m, 2H), 7.70 (m, 1H), 8.14 (d, 1H, J=12 Hz), 9.18 (s, 1H). Analysis calculated for $C_{22}H_{19}F_3N_4O_5 \cdot 2HCl$: C, 48.10; H, 3.85; N, 10.20. Found: C, 47.76; H, 3.80; N, 9.89.

EXAMPLE 444

7-(3,3-Dimethoxy-4-methylpyrrolidin-1-yl)-6-fluoro-1-(2,4-difluorophenyl)-1,8-naphthyridine-3-carboxylic acid Step 1. 7-(3,3-Dimethoxy-4-methylpyrrolidin-1-yl)-6-fluoro-1-(2,4-difluorophenyl)-1,8-naphthyridine-3-carboxylic acid ethyl ester In a reaction similar to that of Step 1, Example 387, into oven-dried glassware maintained under dry $N_2$ were placed 0.132 g (0.91 mmol) of 3,3-dimethoxy-4-methylpyrrolidine (from Step 5 Example 183), 0.300 g (0.78 mmol) of 7-chloro-6-fluoro-1-(2,4-difluorophenyl)-1,8-naphthyridine-3-carboxylic acid ethyl ester, 12 mL of dry pyridine and 0.437 mL (3.1 mmol) of triethylamine. The reaction was stirred at room temperature for 15 hours, then the solvent was removed in a rotary evaporator. The residue was dissolved in methylene chloride and the product purified by column chromatography over silica gel, eluting with 0.5% increasing to 3% methanol/methylene chloride which was evaporated to afford 0.240 g of the title compound. This material was taken directly to the next step.

Step 2. 7-(3,3-Dimethoxy-4-methylpyrrolidin-1-yl)-6-fluoro-1-(2,4-difluorophenyl)-1,8-naphthyridine-3-carboxylic acid The 0.240 g sample of the ester from Step 1 was hydrolyzed and the product isolated by a procedure similar to that in Step 2 Example 387. The title compound (0.204 g) was obtained as a solid, mp 179°-182° C.; MS (FAB) M/Z 464 (M+H), 446 (M+H-H$_2$O). NMR (CDCl$_3$) d 1.02 (d, 3H, J=7.5 Hz), 2.43 (m, 1H), 3.25 (s, 3H), 3.29 (s, 3H), 4.71 (m, 4H), 7.17 (m, 2H), 7.52 (m, 1H), 8.03 (d, 1H, J=12 Hz), 8.60 (s, 1H). Analysis calculated for $C_{22}H_{20}F_3N_3O_5 \cdot H_2O$: C, 54.89; H, 4.61, N, 8.73. Found: C, 54.79, H, 4.34; N, 8.48.

EXAMPLE 445

7-(2-dimethylaminomethyl-1,4-dioxa-7-azaspiro[4.4]-non-7-yl)-6-fluoro-1-(2,4-difluorophenyl)-1,8-naphthyridine-3-carboxylic acid Step 1. 7-(2-dimethylaminomethyl-1,4-dioxa-7-azaspiro[4.4]non-7-yl)-6-fluoro-1-(2,4-difluorophenyl)-1,8-naphthyridine-3-carboxylic acid ethyl ester In a reaction similar to that of Step 1 Example 387, into oven-dried glassware maintained under dry N2 were placed 0.219 g (1.2 mmol) of 2-dimethylaminomethyl-1,4-dioxa-7-azaspiro[4.4]nonane (from Step 2 Example 171), 0.300 g (0.78 mmol) of 7-chloro-6-fluoro-1-(2,4-difluorophenyl)-1,8-naphthyridine-3-carboxylic acid ethyl ester, 10 mL of dry pyridine and 0.44 mL (3.2 mmol) of triethylamine. The reaction was stirred at 45° C. for 24 hours, then the solvent was removed in a rotary evaporator. The residue was dissolved in methylene chloride, washed with 2×50 mL of water, dried over anhydrous sodium sulfate and filtered. The solvent was removed by evaporation to afford after drying 0.447 g of the title compound. This material was taken directly to the next step.

Step 2. 7-(2-dimethylaminomethyl-1,4-dioxa-7-azaspiro[4.4]non-7-yl)-6-fluoro-1-(2,4-difluorophenyl)-1,8-naphthyridine-3-carboxylic acid The 0.447 g sample of the ester from Step 1 was hydrolyzed and the product isolated by a procedure similar to that in Step 2 Example 387. The title compound (0.283 g) was obtained as a solid, mp 154°–155° C.; MS (FAB) M/Z 505 (M+H), 487 (M+H-H$_2$O). NMR (CDCl3) d 2.07 (m, 2H), 2.29 (s, 6H), 2.38 (m, 2H), 2.50 (m, 2H), 3.62 (m, 2H), 4.09 (m, 2H), 4.27 (m, 1H), 7.06 (m, 2H), 7.37 (m, 1H), 8.04 (d, 1H, J=12.0 Hz), 8.63 (s, 1H). Analysis calculated for $C_{24}H_{23}F_3N_4O_5 \cdot 0.5\ H_2O$: C, 56.14; H, 4.71; N, 10.91. Found: C, 56.61; H, 4.53; N, 11.13.

EXAMPLE 446

7-(9-amino-1,4-dioxa-7-azaspiro[4.4]non-7-yl)-6-fluoro-1-(2,4-difluorophenyl)-1,8-naphthyridine-3-carboxylic acid hydrochloride Step 1. 7-(9-amino-1,4-dioxa-7-azaspiro[4.4]non-7-yl)-6-fluoro-1-(2,4-difluorophenyl)-1,8-naphthyridine-3-carboxylic acid ethyl ester In a reaction similar to that of Step 1 Example 387, into oven-dried glassware maintained under dry N2 were placed 0.141 g (0.98 mmol) of 9-amino-1,4-dioxa-7-azaspiro[4.4]nonane (from Step 5 Example 208), 0.250 g (0.65 mmol) of 7-chloro-6-fluoro-1-(2,4-difluorophenyl)-1,8-naphthyridine-3-carboxylic acid ethyl ester, 10 mL of dry pyridine and 0.364 mL (2.6 mmol) of triethylamine. The reaction was stirred at room temperature for 2.25 hours, then the mixture was poured into water and extracted with 3×60 mL portions of methylene chloride, which was washed with 2×50 mL of water, dried over anhydrous sodium sulfate and filtered. The solvent was removed by evaporation to afford after drying 0.404 g of the title compound. This material was taken directly to the next step.

Step 2. 7-(9-amino-1,4-dioxa-7-azaspiro[4.4]non-7-yl)-6-fluoro-1-(2,4-difluorophenyl)-1,8-naphthyridine-3-carboxylic acid hydrochloride The 0.404 g sample of the ester from Step 1 was hydrolyzed and the product isolated by a procedure similar to that in Step 7 Example 208. The title compound (0.231 g) was obtained as a solid, mp 195° C. dec; MS (DCI) M/Z 463 (M+H)(base). NMR (TFA/AA) d 3.94–4.78 (m, 11H), 7.25 (m, 2H), 7.65 (m, 1H), 8.28 (d, 1H, J=10.5 Hz), 9.21 (s, 1H). Analysis calculated for $C_{21}H_{18}F_3N_4O_5 \cdot HCl \cdot 3\ H_2O$: C, 45.62; H, 4.38; N, 10.13. Found: C, 45.65; H, 3.89; N, 9.72.

EXAMPLE 447

7-(9-aminomethyl-1,4-dioxa-7-azaspiro[4.4]non-7-yl)-6-fluoro-1-(2,4-difluorophenyl)-1,8-naphthyridine-3-carboxylic acid hydrochloride Step 1. 4-Aminomethyl-3-pyrrolidinol benzyl carbamate a. Magnesium sulfate (14.92 g, 124 mmol) was dissolved in 290 mL of water by stirring at room temperature for 20 min. To this solution was added 20.25 g (413 mmol) of sodium cyanide and the mixture was stirred for 20 min. A 15.1 g (68.9 mmol) sample of 3,4-epoxypyrrolidine benzyl carbamate, from Step 1b Example 208, was dissolved in 150 mL of ethanol and added dropwise to the cyanide solution over 40 min. The mixture was heated to 65° C. and stirred for 20 hours. The dark precipitate was filtered off, rinsed with water and methylene chloride. The filtrate was extracted with methylene chloride, which was dried over anhydrous sodium sulfate, filtered and evaporated under vacuum. The product was purified by column chromatography on silica gel to afford after drying 8.0 g of 4-cyano-3-pyrrolidinol benzyl carbamate, MS (DCI) M/Z 247 (M+H); NMR (CDCl3) d 2.84 (m, 1H), 3.06 (m, 1H), 3.59 (m, 1H), 3.82 (m, 3H), 4.58 (m, 1H), 5.14 (m, 2H), 7.37 (m, 5H).

b. The compound from Step 1a was hydrogenated to convert the cyano group into an aminomethyl group, by dissolving a 7.2 g sample in 170 mL of methanol, adding 14.5 g of Raney Ni, 30 mL of triethylamine and maintaining under 4 atm of H$_2$ at room temperature for 42 hours. The catalyst was removed by filtration, and the solvent was removed under vacuum to afford 7.61 g of 4-aminomethyl-3-pyrrolidine benzyl carbamate, MS (DCI) M/Z 251 (M+H). This material was taken directly to the next step.

Step 2. 4-aminomethyl-3-pyrrolidinol 1,4-bis-benzyl carbamate

Following the procedure of Step 2 Example 208, the 7.61 g (30.4 mmol) sample from the previous step was reacted with benzylchloroformate and isolated, omitting the chromatography, to afford 12.07 g of the title compound, MS (DCI) M/Z 385 (M+H); NMR (CDCl3)d 3.33 (m, 2H), 3.68 (dd, 1H, J=6, 12 Hz), 3.83 (dd, 1H, J=6, 12 Hz), 3.99 (m, 1H), 4.25 (m, 1H), 5.09 (m, 4H), 7.32 (m, 10H).

Step 3. 4-aminomethylpyrrolidin-3-one 1,4-bis-benzyl carbamate

Following the procedure of Step 3 Example 208, the 12.07 g (31.4 mmol) sample from the previous step was reacted with phenyl dichlorophosphate, except stirring for 20 hours instead of 5 hours at room temperature, and isolated. The purification required elution with 0%, 0.5%, and 3% methanol/methylene chloride to afford 8.35 g of the title compound, MS (DCI) M/Z 400 (M+NH$_4$), 383 (M+H), 292 (M-benzyl); NMR (CDCl3) d 2.84 (m, 1H), 3.45 (m, 3H), 3.73 (m, 1H), 3.98 (m, 1H), 4.18 (m, 1H), 5.08 (s, 2H), 5.19 (s, 2H), 7.35 (m, 10H).

Step 4. 9-aminomethyl-1,4-dioxa-7-azaspiro[4.4]nonane 7,9-bis-benzyl carbamate

Following the procedure of Step 4 Example 208, the ketone was reacted with a 2.5-fold excess of ethylene glycol, heating at 110° C. for 28 hours instead of 5 hours and isolated. The compound was purified by column chromatography over silica gel, eluting with 0%, 0.5% and 1% methanol/methylene chloride to afford after drying 4.83 g of the title compound, MS (DCI) M/Z 444 (M+NH$_4$), 427 (M+H), 336 (M-benzyl); NMR (CDCl3) d 2.49 (m, 1H), 3.34 (m, 4H), 3.49 (m, 1H), 3.70 (m, 1H), 3.95 (m, 4H), 5.12 (m, 4H), 7.35 (m, 10H). Analysis calculated for $C_{23}H_{26}N_2O_6 \cdot 2H_2O$: C, 59.73; H, 6.54; N, 6.06. Found: C, 59.56; H, 6.28; N, 5.85.

Step 5. 9-aminomethyl-1,4-dioxa-7-azaspiro[4.4]nonane

The protecting groups were removed from a 4.80 g (11.26 mmol) sample of the compound from the previous step by dissolving it in 200 mL of methanol, adding 2.0 g of 10% Pd/C and 2.0 g of Pd black, and hydrogenating at 4 atm $H_2$ for 48 hours. The catalyst was removed by filtration, and the solvent was removed under vacuum to afford 1.50 g of the title compound, MS (DCl) M/Z 159 (M+H); NMR ($CDCl_3$) d 2.15 (m, 1H), 2.73 (m, 3H), 2.89 (m, 2H), 3.27 (dd, 1H, J=9, 12 Hz), 3.95 (m, 4H).

Step 6. 7-(9-Aminomethyl-1,4-dioxa-7-azaspiro[4.4]non-7-yl)-6-fluoro-1-(2,4-difluorophenyl)-1,8-naphthyridine-3-carboxylic acid ethyl ester In a reaction similar to that of Step 1 Example 387, into oven-dried glassware maintained under dry $N_2$ were placed 0.155 g (1 mmol) of the compound from Step 5, 0.300 g (1.3 mmol) of 7-chloro-6-fluoro-1-(2,4-difluorophenyl)-1,8-naphthyridine-3-carboxylic acid ethyl ester, 12 mL of dry pyridine and 0.33 mL (2.4 mmol) of triethylamine. The reaction was stirred at room temperature for 2 hours, then the solvent was removed by evaporation after toluene was added to azeotrope the pyridine. The residue was dissolved in 50 mL of methylene chloride, which was washed with 2×50 mL of water, dried over anhydrous sodium sulfate, filtered and dried. The crude product was dissolved in methylene chloride and the product purified by column chromatography over silica gel to afford after drying 0.154 g of the title compound, MS (DCI) M/Z 505 (M+H); NMR ($CDCl_3$) d 1.39 (t, 3H, J=7.5 Hz), 2.30 (m, 1H), 2.7 (m, 1H), 3.99 (m, 4H), 4.38 (q, 2H, J=7.5 Hz), 7.05 (m, 2H), 7.39 (m, 1H), 8.07 (d, 1H, J=12 Hz), 8.37 (s, 1H).

Step 7. 7-(9-Aminomethyl-1,4-dioxa-7-azaspiro[4.4]non-7-yl)-6-fluoro-1-(2,4-difluorophenyl)-1,8-naphthyridine-3-carboxylic acid hydrochloride A 0.145 g (0.29 mmol) sample of the ester from Step 6 was hydrolyzed and the product isolated by a procedure similar to that in Step 7 Example 208. The title compound (0.032 g) was obtained as a solid; MS (DCI) M/Z 477 (M+H)(base), 459 (M-$H_2O$). NMR d 2.90 (m, 1H), 3.42 (m, 2H), 4.10 (m, 8H), 7.25 (m, 2H), 7.73 (m, 1H), 8.19 (m, 1H), 9.16 (s, 1H). Analysis calculated for $C_{22}H_{19}F_3N_4O_5 \cdot HCl \cdot 1.5\ H_2O \cdot CH_3OH$: C, 48.30; H, 4.76; N, 9.80. Found: C, 48.02; H, 3.83; N, 10.92.

EXAMPLES 448–458

By following the procedures described in Example 447 and replacing 1-(2,4-difluorophenyl)-7-chloro-6-fluoro-1,8-naphthyridine-3-carboxylic acid ethyl ester (in Step 6), with the appropriate compound containing $R^1, R^3$, and A, below, Examples 448–458 may be prepared as disclosed in Table 16.

TABLE 16

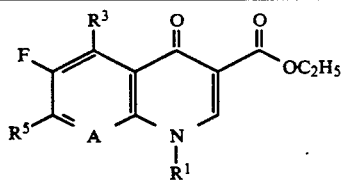

| Example # | $R^1$ | $R^3$ | A |
|---|---|---|---|
| 448 | —C2H5 | H | CH |
| 449 | —C2H4—F | H | CH |
| 450 | —NH—CH3 | H | CH |
| 451 | -cyclopropyl | F | CH |
| 452 | -cyclopropyl | NH2 | CH |

TABLE 16-continued

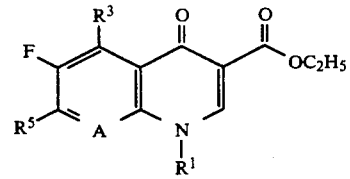

| Example # | $R^1$ | $R^3$ | A |
|---|---|---|---|
| 453 | -cyclopropyl | H | C—CH3 |
| 454 | -cyclopropyl | H | C—Cl |
| 455 | -cyclopropyl | CH3 | CH |
| 456 | -t-butyl | H | CH |
| 457 | 3-methyl-1-butyn-3-yl | H | CH |
| 458 | bicyclo[1.1.1]pent-1-yl | H | CH |

EXAMPLE 459

7-(1,5-Dioxa-9-azaspiro[5.5]undec-9-yl)-6-fluoro-1-(2,4-difluorophenyl)-1,8-naphthyridine-3-carboxylic acid Step 1. 7-(1,5-Dioxa-9-azaspiro[5.5]undec-9-yl)-6-fluoro-1-(2,4-difluorophenyl)-1,8-naphthyridine-3-carboxylic acid ethyl ester In a reaction similar to that of Step 1, Example 387, into oven-dried glassware maintained under dry $N_2$ were placed 0.622 g (3.96 mmol) of 1,5-dioxa-9-azaspiro[5.5]undecane, from Step 4 Example 196, 0.500 g (1.3 mmol) of 7-chloro-6-fluoro-1-(2,4-difluorophenyl)-1,8-naphthyridine-3-carboxylic acid ethyl ester, and 15 mL of dry pyridine. The reaction was stirred at room temperature for 5 hours, then the solvent was removed by evaporation. The residue was dissolved in 50 mL of methylene chloride, which was washed with 50 mL of 5% sodium bicarbonate and 50 mL of water, dried over anhydrous sodium sulfate, filtered and dried. The product was purified by recrystallization from ethanol/water, isolated by filtration and dried under vacuum to afford 0.576 g of the title compound, mp 177°–178° C., MS (DCl/$NH_3$) M/Z 504 (M+H) (base). Analysis calculated for $C_{25}H_{24}F_3N_3O_5$: C, 59.64; H, 4.80; N, 8.35. Found: C, 61.13; H, 5.09; N, 8.36.

Step 2. 7-(1,5-Dioxa-9-azaspiro[5.5]undec-9-yl)-6-fluoro-1-(2,4-difluorophenyl)-1,8-naphthyridine-3-carboxylic acid A 0.503 g (1 mmol) sample of the ester from Step 1 was hydrolyzed and the product isolated by a procedure similar to that in Step 2 Example 387. The title compound (0.448 g) was obtained as a solid, mp 253°–254° C.; MS (FAB) M/Z 476 (M+H), 458 (M+H-$H_2O$). NMR ($CDCl3$) d 1.72 (m, 2H), 1.85 (dd, 4H, J=6 Hz), 3.60 (dd, 4H, J=6 Hz), 3.90 (dd, 4H, J=6 Hz), 7.05 (m, 2H), 7.41 (m, 1H), 8.10 (d, 1H, J=13.5 Hz), 8.67 (s, 1H). Analysis calculated for $C_{23}H_{20}F_3N_3O_5$: C, 58.11; H, 4.24; N, 8.83. Found: C, 57.78; H, 4.25; N, 8.71.

EXAMPLE 460

7-(2-Aminomethyl-1,4-dioxa-8-azaspiro[4.5]dec-8-yl)-6-fluoro-1-(2,4-difluorophenyl)-1,8-naphthyridine-3-carboxylic acid hydrochloride Step 1. 2-Aminomethyl-1,4-dioxa-8-azaspiro[4.5]decane benzyl carbamate a. A 5.00 g (21.43 mmol) sample of 4-piperidinone benzyl carbamate, from Step 2 Example 196, 4.69 mL (53.59 mmol) of 3-bromo-1,2-propanediol, and 0.200 g (1.07 mmol) of p-toluenesulfonic acid was added to 100 mL of toluene and the mixture was heated at 110° C. for 24 hours. The reaction solution was poured into 200 mL of 7% sodium bicarbonate solution, washed well, washed with water, dried over anhydrous sodium sulfate and the solvent removed under vacuum to afford 7.79 g of 2-bromomethyl-1,4-dioxa-8-azaspiro[4.5]decane benzyl carbamate, MS (DCI) M/Z 387 (M+NH$_4$), 370 (M+H). NMR (CDCl$_3$): d 1.69 (m, 4H), 3.31 (dd, 1H, J=9.0, 10.5 Hz), 3.44 (dd, 1H, J=6.0, 9.0 Hz), 3.58 (m, 4H), 3.90 (dd, 1H, J=6.0, 9.0 Hz), 4.14 (dd, 1H, J=6.0, 9.0 Hz), 4.37 (m, 1H), 5.13 (s, 2H), 7.34 (m, 5H).

b. A 4.00 g (11.23 mmol) sample of the bromomethyl compound from Step 1a was dissolved in 80 mL of DMSO, and 1.23 g (18.92 mmol) of sodium azide was added. The solution was stirred at 40° C. for 70 hours, then poured into 200 mL of water and extracted with 3×100 mL of methylene chloride. The organic solution was dried over anhydrous sodium sulfate, and the solvent was removed by evaporation under vacuum to afford 2.08 g of 2-azidomethyl-1,4-dioxa-8-azaspiro[4.5]decane benzyl carbamate, MS M/Z 350 (M+NH$_4$), 333 (M+H). NMR (CDCl$_3$): d 1.72 (m, 4H), 3.30 (dd, 1H, J=4.5, 13.5 Hz), 3.42 (dd, 1H, J=4.5, 13.5 Hz), 3.60 (m, 4H), 3.81 (dd, 1H, J=6.0, 9.0 Hz), 4.09 (dd, 1H, J=6.0, 9.0 Hz), 4.32 (quint, 1H, J=6.0 Hz), 5.63 (s, 2H), 7.35 (m, 5H).

c. A 2.08 g (6.26 mmol) of the azidomethyl compound from Step 1b was dissolved in 16 mL of THF and 0.159 g (4.20 mmol) of sodium borohydride was added. The mixture was stirred at 60° C. and 0.84 mL (20.7 mmol) of methanol in 4 mL of THF was added dropwise over 20 min, then the temperature was increased to 70° C. for 5 hours. After cooling, 5 mL of saturated ammonium chloride solution was added slowly to quench excess borohydride. The solution was adjusted to pH 12 with 1.0M NaOH then extracted with 3×50 mL of methylene chloride. After drying over anhydrous sodium sulfate the solvent was removed by evaporation under vacuum to afford 2.46 g of 2-aminomethyl-1,4-dioxa-8-azaspiro[4.5]decane benzyl carbamate; NMR (CDCl$_3$): d 1.64 (m, 4H), 2.82 (m, 2H), 3.58 (m, 4H), 3.69 (dd, 1H, J=7.5, 9.0 Hz), 4.05 (dd, 1H, J=6.9, 9.0 Hz), 4.15 (m, 1H), 5.12 (s, 2H), 7.35 (m, 5H).

Step 2. 2-t-butoxycarbonylaminomethyl-1,4-dioxa-8-azaspiro[4.5]decane benzyl carbamate A 2.46 g (8.03 mmol) sample of the aminomethyl compound from Step 1c and 2.24 mL (16.06 mmol) of triethylamine were dissolved in 24 mL of methylene chloride, then 2.63 g (12.05 mmol) of di-t-butyl dicarbonate dissolved in 10 mL of methylene chloride was added dropwise over 20 min. The mixture was stirred at room temperature for 5 hours then at 35° C. for 18 hours. The mixture was poured into 100 mL of water and extracted with 2×50 mL of methylene chloride. The organic solution was dried over anhydrous sodium sulfate, and the solvent was removed by evaporation under vacuum. The residue was purified by column chromatography over silica gel to afford 3.07 g of the title compound; NMR (CDCl$_3$): d 1.45 (s, 9H), 1.68 (m, 4H), 3.19 (m, 1H), 3.39 (m, 1H), 3.55 (m, 4H), 3.68 (dd, 1H, J=6.0, 9.0 Hz), 4.04 (dd, 1H, J=6.0, 9.0 Hz), 4.22 (m, 1H), 5.13 (s, 2H), 7.35 (m, 5H).

Step 3. 2-t-butoxycarbonylaminomethyl-1,4-dioxa-8-azaspiro[4.5]decane

A 3.07 g (7.55 mmol) sample of the compound from Step 2 was dissolved in 150 mL of methanol and deprotected at the piperidine nitrogen by hydrogenation with 0.65 g 20% Pd/C at room temperature and 4 atm of hydrogen for 24 hours. The catalyst was removed by filtration, and the solvent was removed under vacuum to afford 1.79 g of the title compound; NMR (CDCl$_3$): d 1.45 (s, (H)), 1.71 (m, 2H), 1.99 (m, 2H), 3.24 (m, 4H), 3.39 (m, 1H), 3.68 (m, 1H), 4.05 (m, 1H), 4.22 (m, 1H), 4.84 (m, 1H).

Step 4. 7-(2-t-butoxycarbonylaminomethyl-1,4-dioxa-8-azaspiro[4.5]dec-8-yl)-6-fluoro-1-(2,4-difluorophenyl)-1,8-naphthyridine-3-carboxylic acid ethyl ester In a reaction similar to that of Step 1 Example 387, into oven-dried glassware maintained under dry N$_2$ were placed 0.427 g (1.57 mmol) of the compound from Step 4, 0.400 g (1.05 mmol) of 7-chloro-6-fluoro-1-(2,4-difluorophenyl)-1,8-naphthyridine-3-carboxylic acid ethyl ester, 15 mL of dry pyridine and 0.583 mL (4.19 mmol) of triethylamine. The reaction was stirred at 40° C. for 2 hours, then the solvent was removed in a rotary evaporator. The crude product was purified by column chromatography over silica gel, eluting with 0.5% increasing to 2% methanol/methylene chloride, to afford 0.616 g of the title compound. This material was taken directly to the next step.

Step 5. 7-(2-aminomethyl-1,4-dioxa-8-azaspiro[4.5]dec-8-yl)-6-fluoro-1-(2,4-difluorophenyl)-1,8-naphthyridine-3-carboxylic acid ethyl ester The boc protecting group was removed from the 0.616 g sample of the compound from Step 4 by dissolving it in 10 mL of trifluoroacetic acid and stirring for 2 hours at room temperature. The excess acid was removed under vacuum and the residue was dissolved in 400 mL of methanol. Eight g of anion exchange resin (hydroxide form) was added and the mixture was stirred at room temperature for 2 hours. The resin was filtered off and the solvent was evaporated to afford 0.534 g of the title compound, which was taken directly to the next step.

Step 6. 7-(2-aminomethyl-1,4-dioxa-8-azaspiro[4.5]dec-8-yl)-6-fluoro-1-(2,4-difluorophenyl)-1,8-naphthyridine-3-carboxylic acid hydrochloride The 0.534 g sample of the ester from the previous step was suspended in 5 mL of THF, 10 mL of 1M NaOH was added and the mixture stirred at 50° C. for 4 hours, then at 85° C. to distill off the THF. The solution was poured into water, then acidified to pH 1 with conc. HCl. The product was filtered off and washed with hot ethanol, then suspended in ethanol and heated at reflux for 2 hours, filtered and dried to afford 0.85 g of the title compound, mp 189°–191° C.; MS (FAB) M/Z 491 (M+H), 473 (M+H-H$_2$O). NMR (CDCl$_3$): d 3.95 (m, 13H), 7.25 (m, 2H), 7.73 (m, 1H), 8.28 (d, 1H, J=13.5 Hz), 9.08 (s, 1H). Analysis calculated for C$_{23}$H$_{21}$F$_3$N$_3$O$_5$·HCl·1.25 H$_2$O: C, 50.28; H, 4.49; N, 10.19. Found: C, 50.04; H, 4.21; N, 9.76.

EXAMPLES 461–471

By following the procedures described in Example 460 and replacing 1-(2,4-difluorophenyl)-7-chloro-6-fluoro-1,8-naphthyridine-3-carboxylic acid ethyl ester (in Step 4), with the appropriate compound containing $R^1$, $R^3$, and A, below, Examples 461–471 may be prepared as disclosed in Table 17.

TABLE 17

[Structure: naphthyridine core with R³, F, R⁵, A, R¹, and OC₂H₅ ester groups]

| Example # | R¹ | R³ | A |
|---|---|---|---|
| 461 | —C2H5 | H | CH |
| 462 | —C2H4—F | H | CH |
| 463 | —NH—CH3 | H | CH |
| 464 | -cyclopropyl | F | CH |
| 465 | -cyclopropyl | NH2 | CH |
| 466 | -cyclopropyl | H | C—CH3 |
| 467 | -cyclopropyl | H | C—Cl |
| 468 | -cyclopropyl | CH3 | CH |
| 469 | -t-butyl | H | CH |
| 470 | 3-methyl-1-butyn-3-yl | H | CH |
| 471 | bicyclo[1.1.1]pent-1-yl | H | CH |

EXAMPLE 472

1-(2,4-Difluorophenyl)-6-fluoro-7-(2-methylaminomethyl-1,4-dioxa-8-azaspiro[4.5]dec-8-yl)-1,8-naphthyridine-3-carboxylic acid hydrochloride Step 1. 2-Methylaminomethyl-1,4-dioxa-8-azaspiro[4.5]decane 8-benzyl carbamate A 1.00 g (2.70 mmol) sample of 2-bromomethyl-1,4-dioxa-8-azaspiro[4.5]decane benzyl carbamate, from Step 1a Example 460, and 20 mL of methylamine were dissolved in 15 mL of methanol, sealed in a glass tube and heated at 100° C. for 24 hours. The tube was cooled and opened and the solvent was removed to afford 0.865 g of the title compound, MS M/Z 321 (M+H).

Step 2. 2-(N-t-butoxycarbonyl-N-methylaminomethyl)-1,4-dioxa-8-azaspiro[4.5]decane 8-benzyl carbamate A 0.865 g (2.70 mmol) sample of the compound from Step 1 and 0.95 mL (5.40 mmol of triethylamine were dissolved in 10 mL of methylene chloride and stirred at 0° C. under dry conditions. To this was added dropwise over 30 min 1.11 g (4.05 mmol) of di-t-butyl dicarbonate dissolved in 5 mL of methylene chloride. The temperature was increased to 40° C. for 4 hours, the solution diluted with 50 mL of methylene chloride and washed with 2×50 mL of water. The organic layer was dried over anhydrous sodium sulfate and the solvent was removed by evaporation under vacuum to afford 1.14 g of the title compound, MS M/Z 421 (M+H), 321 (M-boc).

Step 3. 2-(N-t-butoxycarbonyl-N-methylaminomethyl)-1,4-dioxa-8-azaspiro[4.5]decane By the procedure of Step 3 Example 460 the piperidine nitrogen protecting group was removed from a 1.14 g (2.70 mmol) sample of the compound from Step 2 to afford 0.870 g of the title compound, MS (DCl) M/Z 287 (M+H). NMR (CDCl₃): d 1.47 (s, 9H), 1.69 (m, 4H), 2.94 (s, 3H), 3.26 (m, 1H), 3.44 (m, 1H), 3.58 (m, 4H), 3.67 (dd, 1H, J=6.0, 7.5 Hz), 4.05 (dd, 1H, J=6.0, 7.5 Hz), 4.26 (m, 1H).

Step 4. 7-(2-N-t-Butoxycarbonyl-N-methylaminomethyl-1,4-dioxa-8-azaspiro[4.5]dec-8-yl)-1-(2,4-difluorophenyl)-6-fluoro-1,8-naphthyridine-3-carboxylic acid ethyl ester In a reaction similar to that of Step 1 Example 387, into oven-dried glassware maintained under dry N₂ were placed 0.380 g (1.33 mmol) of the compound from Step 4, 0.400 g (1.05 mmol) of 7-chloro-6-fluoro-1-(2,4-difluorophenyl)-1,8-naphthyridine-3-carboxylic acid ethyl ester, 15 mL of dry pyridine and 0.583 mL (4.19 mmol) of triethylamine. The reaction was stirred at room temperature for 6 hours, then the solvent was removed in a rotary evaporator. The crude product was dissolved in 20 mL of methylene chloride and washed with 2×30 mL of water, the organic layer was dried over anhydrous sodium sulfate and the solvent was removed by evaporation, and the product further purified by column chromatography over silica gel, eluting with 0.5% increasing to 2.5% methanol/methylene chloride, to afford after drying 0.359 g of the title compound. NMR (CDCl₃) d 1.40 (t, 3H, J=7.5 Hz), 1.45 (s, 9H), 1.57 (s, 3H), 1.66 (m, 4H), 3.60 (m, 4H), 3.67 (dd, 1H, J=7.5, 6.0 Hz), 4.03 (dd, 1H, J=7.5, 6.0 Hz), 4.25 (m, 1H), 4.39 (q, 2H, J=7.5 Hz), 7.05 (m, 2H), 7.39 (m, 1H), 8.13 (d, 1H, J=12 Hz), 8.40 (s, 1H).

Step 5. 1-(2,4-Difluorophenyl)-6-fluoro-7-(2-methylaminomethyl-1,4-dioxa-8-azaspiro[4.5]dec-8-yl)-1,8-naphthyridine-3-carboxylic acid ethyl ester The boc protecting group was removed from a 0.350 g sample of the compound from Step 4 by dissolving it in 10 mL of trifluoroacetic acid and stirring for 2 hours at room temperature. The excess acid was removed under vacuum and the residue was dissolved in 300 mL of methanol. Eight g of anion exchange resin (hydroxide form) was added and the mixture was stirred at room temperature for 2 hours. The resin was filtered off and the solvent was evaporated to afford 0.269 g of the title compound, which was taken directly to the next step.

Step 6. 1-(2,4-Difluorophenyl)-6-fluoro-7-(2-methylaminomethyl-1,4-dioxa-8-azaspiro[4.5]dec-8-yl)-1,8-naphthyridine-3-carboxylic acid hydrochloride The 0.269 g sample of the ester from the previous step was suspended in 5 mL of THF, 10 mL of 1M NaOH was added and the mixture stirred at 50° C. for 4 hours, then at 85° C. to distill off the THF. The solution was poured into water, then acidified to pH 2 with conc. HCl. The product was filtered off and washed with water and dried to afford 0.230 g of the title compound, mp 209°–211° C.; MS (FAB) M/Z 505. NMR (CDCl₃): d 2.96 (s, 3H), 4.08 (m, 3H), 7.25 (m, 2H), 7.72 (m, 1H), 8.23 (dd, 1H, J=12,24 Hz), 9.22 (d, 1H, J=15 Hz). Analysis calculated for C₂₄H₂₃ClF₃N₄O₅·0.5 H₂O: C, 52.42; H, 4.58; N, 10.19. Found: C, 52.34; H, 4.37; N, 9.81

EXAMPLES 473–483

By following the procedures described in Example 472 and replacing 1-(2,4-difluorophenyl)-7-chloro-6-fluoro-1,8-naphthyridine-3-carboxylic acid ethyl ester (in Step 4), with the appropriate compound containing R¹,R³, and A, below, Examples 473–483 may be prepared as disclosed in Table 18.

TABLE 18

[Structure: naphthyridine core with R³, F, R⁵, A, R¹, and OC₂H₅ ester groups]

| Example # | R¹ | R³ | A |
|---|---|---|---|
| 473 | —C2H5 | H | CH |
| 474 | —C2H4—F | H | CH |

TABLE 18-continued

[Structure: naphthyridine with R3, F, R5, A, N-R1, and OC2H5 ester groups]

| Example # | R¹ | R³ | A |
|---|---|---|---|
| 475 | —NH—CH3 | H | CH |
| 476 | -cyclopropyl | F | CH |
| 477 | -cyclopropyl | NH2 | CH |
| 478 | -cyclopropyl | H | C—CH3 |
| 479 | -cyclopropyl | H | C—Cl |
| 480 | -cyclopropyl | CH3 | CH |
| 481 | -t-butyl | H | CH |
| 482 | 3-methyl-1-butyn-3-yl | H | CH |
| 483 | bicyclo[1.1.1]pent-1-yl | H | CH |

EXAMPLE 484

1-(2,4-Difluorophenyl)-6-fluoro-7-(2-methylaminomethyl-1,4-dioxa-8-azaspiro[4.5]dec-8-yl)-1,8-naphthyridine-3-carboxylic acid Step 1. 2-Dimethylaminomethyl-1,4-dioxa-8-azaspiro[4.5]decane 8-benzyl carbamate A 1.26 g (3.53 mmol) sample of 2-bromomethyl-1,4-dioxa-8-azaspiro[4.5]decane benzyl carbamate, from Step 1a Example 460, and 25 mL of dimethylamine were dissolved in 75 mL of ethanol, sealed in a glass tube and heated at 50° C. for 20 hours. The tube was cooled and opened and the solvent was removed under vacuum. The crude product was purified by column chromatography over silica gel to afford 1.16 g of the title compound, MS M/Z 335 (M+H); NMR (CDCl₃) d 1.69 (m, 4H), 3.53 (m, 5H), 3.63 (dd, 1H, J=7.5, 9 Hz), 4.15 (dd, 1H, J=6, 7.5 Hz), 4.45 (m, 1H), 5.13 (s, 2H), 7.35 (m, 5H).

Step 2. 2-Dimethylaminomethyl-1,4-dioxa-8-azaspiro[4.5]decane

By the procedure of Step 3 Example 460 the piperidine nitrogen protecting group was removed from a 1.16 g (3.57 mmol) sample of the compound from Step 1 to afford 1.16 g of the title compound, MS (DCI) M/Z 201 (M+H).

Step 3. 1-(2,4-Difluorophenyl)-7-(2-dimethylaminomethyl-1,4-dioxa-8-azaspiro[4.5]dec-8-yl)-6-fluoro-1,8-naphthyridine-3-carboxylic acid ethyl ester In a reaction similar to that of Step 1 Example 387, into oven-dried glassware maintained under dry N₂ were placed 0.253 g (1.26 mmol) of the compound from Step 2, 0.300 g (0.78 mmol) of 7-chloro-6-fluoro-1(2,4-difluorophenyl)-1,8-naphthyridine-3-carboxylic acid ethyl ester, 15 mL of dry pyridine and 0.44 mL (3.14 mmol) of triethylamine. The reaction was stirred at 40° C. for 8 hours, then the solvent was removed in a rotary evaporator. The crude product was dissolved in methylene chloride and washed twice with water, the organic layer was dried over anhydrous sodium sulfate and the solvent was removed by evaporation. The product was further purified by recrystallization from ethanol/water and column chromatography over silica gel to yield 0.152 g of the title compound, MS M/Z 547 (M+H). This material was taken directly to the next step.

Step 4. 1-(2,4-Difluorophenyl)-7-(2-dimethylaminomethyl-1,4-dioxa-8-azaspiro[4.5]dec-8-yl)-6-fluoro-1,8-naphthyridine-3-carboxylic acid The 0.152 g sample of the ester from the previous step was suspended in 5 mL of THF, 3.7 mL of 1M NaOH was added and the mixture stirred at 50° C. for 4 hours, then at 85° C. to distill off the THF. The solution was poured into water, then acidified to pH 2 with conc. HCl. The product was filtered off and washed with water and dried to afford 0.094 g of the title compound, mp 188°–193° C.; MS (FAB) M/Z 519. NMR (CDCl₃): d 1.61 (m, 4H), 2.43 (s, 6H), 2.64 (m, 2H), 3.61 (dd, 1H, J=7.5, 7.5 Hz), 3.72 (m, 4H), 4.15 (dd, 1H, J=6.0, 7.5 Hz), 7.20 (m, 2), 7.55 (m, 1H), 8.11 (d, 1H, J=13.5), 8.75 (s, 1H). Analysis calculated for $C_{25}H_{25}F_3N_4O_5 \cdot 2.5\ H_2O$: C, 53.28; H, 5.37; N, 9.94. Found: C, 53.56; H, 4.96; N, 9.22.

EXAMPLES 485–495

By following the procedures described in Example 484 and replacing 1-(2,4-difluorophenyl)-7-chloro-6-fluoro-1,8-naphthyridine-3-carboxylic acid ethyl ester (in Step 3), with the appropriate compound containing R¹,R³, and A, below, Examples 485–495 may be prepared as disclosed in Table 19.

TABLE 19

[Structure: naphthyridine with R3, F, R5, A, N-R1, and OC2H5 ester groups]

| Example # | R¹ | R³ | A |
|---|---|---|---|
| 485 | —C2H5 | H | CH |
| 486 | —C2H4—F | H | CH |
| 487 | —NH—CH3 | H | CH |
| 488 | -cyclopropyl | F | CH |
| 489 | -cyclopropyl | NH2 | CH |
| 490 | -cyclopropyl | H | C—CH3 |
| 491 | -cyclopropyl | H | C—Cl |
| 492 | -cyclopropyl | CH3 | CH |
| 493 | -t-butyl | H | CH |
| 494 | 3-methyl-1-butyn-3-yl | H | CH |
| 495 | bicyclo[1.1.1]pent-1-yl | H | CH |

EXAMPLE 496

7-(2-aminomethyl-1,4-dioxa-7-azaspiro[4.4]non-7-yl)-1-cyclopropyl-6-fluoro-1,8-naphthyridine-3-carboxylic acid dihydrochloride Step 1. 7-(2-t-butoxycarbonylaminomethyl-1,4-dioxa-7-azaspiro[4.4]non-7-yl)-1-cyclopropyl-6-fluoro-1,8-naphthyridine-3-carboxylic acid ethyl ester In a reaction similar to that of Step 1 Example 443, into oven-dried glassware maintained under dry N₂ were placed 0.500 g (1.94 mmol) of 2-t-butoxycarbonylaminomethyl-1,4-dioxa-7-azaspiro[4.4]nonane, from Step 5 Example 159, and 0.400 g (1.29 mmol) of 7-chloro-1-cyclopropyl-6-fluoro-1,8-naphthyridine-3-carboxylic acid ethyl ester (preparation described by D. T. W. Chu et al. S. African Patent NO. ZA 8504792, Feb. 26, 1986) (substituting for the naphthyridine compound of Example 443), 12 mL of pyridine and 0.718 mL (5.16 mmol) of triethylamine. The reaction was stirred at 35° C. for 6 hours, then the solvent was removed in a rotary evaporator. The product was purified by column chromatography over silica gel to afford after drying 0.485 g of the title compound.

Step 2.
7-(2-aminomethyl-1,4-dioxa-7-azaspiro[4.4]non-7-yl)-1-cyclopropyl-6-fluoro-1,8-naphthyridine-3-carboxylic acid ethyl ester The 0.485 g of the boc-protected compound from Step 1 was deprotected and the product was isolated by a reaction similar to that in Step 7 Example 159, to afford 0.394 g of the title compound, which was taken directly to the next step.

Step 3.
7-(2-aminomethyl-1,4-dioxa-7-azaspiro[4.4]non-7-yl)-1-cyclopropyl-6-fluoro-1,8-naphthyridine-3-carboxylic acid hydrochloride The 0.394 g of the ester from Step 2 was hydrolyzed by the procedure of Step 2 Example 387. The residue was poured into water and conc. HCl was added to adjust the acidity to pH 1. The product was filtered off, stirred in 1:1 methanol/methylene chloride for 2 hours, filtered, and the filtrate dried to afford 0.252 g of the title compound, mp 179°–181° C.; MS (DCI) M/Z 405 (M+H). NMR (TFA/AA) d 1.40 (m, 4H), 4.10 (m, 12H), 8.08 (d, 1H, J=12 Hz), 9.12 (s, 1H). Analysis calculated for $C_{19}H_{22}ClFN_4O_5 \cdot H_2O$: C, 47.85; H, 5.50; N, 11.75. Found: C, 48.54; H, 5.12; N, 11.23.

EXAMPLES 497–550

By following the procedures described in Example 496 and replacing 2-t-butoxycarbonylaminomethyl-1,4-dioza-7-azaspiro[4.4]nonane in Step 1 with the appropriate ketal compound, Examples 497–550 (in which A=N and $R^1$=cyclopropyl) may be prepared as disclosed in Table 20.

TABLE 20

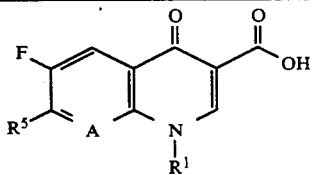

| Example # | $R^5$ is derived from ketal compound: |
|---|---|
| 497* | 2-aminomethyl-3,3-dimethoxypyrrolidine |
| *498 | 6-aminomethyl-1,4-dioxa-7-azaspiro[4.4]nonane |
| *499 | 8-aminomethyl-2-ethyl-1,4-dioxa-7-azaspiro[4.4]nonane |
| 500 | 9-chloro-1,4-dioxa-7-azaspiro[4.4]nonane |
| 501 | 2,3-dimethyl-1,4-dioxa-7-azaspiro[4.4]nonane |
| 502 | 6,9-dimethyl-1,4-dioxa-7-azaspiro[4.4]nonane |
| 503 | 8,9-dimethyl-1,4-dioxa-7-azaspiro[4.4]nonane |
| 504 | 6-fluoro-1,4-dioxa-7-azaspiro[4.4]nonane |
| 505 | 9-fluoromethyl-1,4-dioxa-7-azaspiro[4.4]nonane |
| 506 | 2-ethyl-8-(N-phenylalanyl)-1,4-dioxa-7-azaspiro[4.4]nonane |
| 507 | 2-ethyl-8-(N-valylaminomethyl)-1,4-dioxa-7-azaspiro[4.4]nonane |
| 508 | 9-(N-isoleucyl-valylaminomethyl)-1,4-dioxa-7-azaspiro[4.4]nonane |
| 509 | 9-(N-alanyl-norvalylaminomethyl)-1,4-dioxa-7-azaspiro[4.4]nonane |
| 510 | 9-(N-valyl-tyrosylaminomethyl)-1,4-dioxa-7-azaspiro[4.4]nonane |
| *511 | 10-amino-1,5-dioxa-8-azaspiro[5.4]decane |
| *512 | 4-aminomethyl-1,5-dioxa-8-azaspiro[5.4]decane |
| *513 | 10-aminomethyl-1,5-dioxa-8-azaspiro[5.4]decane |
| *514 | 3-amino-4-methyl-1,5-dioxa-8-azaspiro[5.4]decane |
| 515 | 3-chloro-1,5-dioxa-8-azaspiro[5.4]decane |
| 516 | 4-ethyl-1,5-dioxa-8-azaspiro[5.4]decane |
| 517 | 10-fluoromethyl-1,5-dioxa-8-azaspiro[5.4]decane |
| 518 | 10-methyl-1,5-dioxa-8-azaspiro[5.4]decane |
| 519 | 3-N-(valylamino)-1,5-dioxa-8-azaspiro[5.4]decane |
| 520 | 4-N-(isoleucyl-alanylaminomethyl)-1,5-dioxa-8-azaspiro[5.4]decane |

TABLE 20-continued

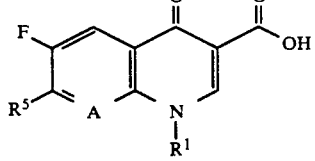

| Example # | $R^5$ is derived from ketal compound: |
|---|---|
| *521 | 6-amino-1,4-dioxa-8-azaspiro[4.5]decane |
| *522 | 6-aminomethyl-1,4-dioxa-8-azaspiro[4.5]decane |
| *523 | 3-aminomethyl-6-methyl-1,4-dioxa-8-azaspiro[4.5]decane |
| 524 | 2,6-dimethyl-1,4-dioxa-8-azaspiro[4.5]decane |
| 525 | 3-N,N-dimethylaminomethyl-1,4-dioxa-8-azaspiro[4.5]decane |
| 526 | 3-ethyl-1,4-dioxa-8-azaspiro[4.5]decane |
| 527 | 6-fluoromethyl-1,4-dioxa-8-azaspiro[4.5]decane |
| 528 | 6-methyl-1,4-dioxa-8-azaspiro[4.5]decane |
| 529 | 3-(N-valylaminomethyl)-1,4-dioxa-8-azaspiro[4.5]decane |
| 530 | 3-(N-leucyl-isoleucylaminomethyl)-1,4-dioxa-8-azaspiro[4.5]decane |
| *531 | 7-amino-1,5-dioxa-9-azaspiro[5.5]undecane |
| *532 | 2-aminomethyl-1,5-dioxa-9-azaspiro[5.5]undecane |
| *533 | 3-aminomethyl-1,5-dioxa-9-azaspiro[5.5]undecane |
| *534 | 8-aminomethyl-1,5-dioxa-9-azaspiro[5.5]undecane |
| 535 | 2-ethyl-7-methyl-1,5-dioxa-9-azaspiro[5.5]undecane |
| 536 | 2-methyl-1,5-dioxa-9-azaspiro[5.5]undecane |
| 537 | 7-methyl-1,5-dioxa-9-azaspiro[5.5]undecane |
| 538 | 3-(N-leucylamino)-1,5-dioxa-9-azaspiro[5.5]undecane |
| 539 | 2-(N-isoleucylaminomethyl)-1,5-dioxa-9-azaspiro[5.5]undecane |
| 540 | 3-(N-alanyl-tyrosylamino)-1,5-dioxa-9-azaspiro[5.5]undecane |
| *541 | 3-amino-1,5-dioxa-8-azaspiro[5.5]undecane |
| *542 | 10-amino-1,5-dioxa-8-azaspiro[5.5]undecane |
| *543 | 2-aminomethyl-1,5-dioxa-8-azaspiro[5.5]undecane |
| *544 | 10-aminomethyl-1,5-dioxa-8-azaspiro[5.5]undecane |
| *545 | 11-aminomethyl-1,5-dioxa-8-azaspiro[5.5]undecane |
| 546 | 10-methyl-1,5-dioxa-8-azaspiro[5.5]undecane |
| 547 | 11-methyl-1,5-dioxa-8-azaspiro[5.5]undecane |
| 548 | 3-(N-valylamino)-1,5-dioxa-8-azaspiro[5.5]undecane |
| 549 | 10-(N-valylamino)-1,5-dioxa-8-azaspiro[5.5]undecane |
| 550 | 3-(N-isoleucyl-valylamino)-1,5-dioxa-8-azaspiro[5.5]undecane |

*Non-ring amino groups are protected and deprotected as in Example 159.

EXAMPLE 551

7-(2-Dimethylaminomethyl-1,4-dioxa-7-azaspiro[4.4]-non-7-yl)-1-cyclopropyl-6-fluoro-1,8-naphthyridine-3-carboxylic acid Step 1. 7-(2-Dimethylaminomethyl-1,4-dioxa-7-azaspiro[4.4]non-7-yl)-1-cyclopropyl-6-fluoro-1,8-naphthyridine-3-carboxylic acid ethyl ester In a reaction similar to that of Step 1 Example 496, into oven-dried glassware maintained under dry N2 were placed 0.270 g (1.45 mmol) of 2-dimethylaminomethyl-1,4-dioxa-7-azaspiro[4.4]nonane (from Step 2 Example 171), 0.300 g (0.97 mmol) of 7-chloro-1-cyclopropyl-6-fluoro-1,8-naphthyridine-3-carboxylic acid ethyl ester, 10 mL of dry pyridine and 0.54 mL (3.9 mmol) of triethylamine. The reaction was stirred at 45° C. for 28 hours, then the solvent was removed in a rotary evaporator. The residue was dissolved in methylene chloride, washed with 2×50 mL of water, dried over anhydrous sodium sulfate and filtered. The solvent was removed by evaporation to afford after drying 0.455 g of the title compound. This material was taken directly to the next step.

Step 2. 7-(2-Dimethylaminomethyl-1,4-dioxa-7-azaspiro[4.4]non-7-yl)-1-cyclopropyl-6-fluoro-1,8-naphthyridine-3-carboxylic acid The 0.455 g of the ester from Step 2 was hydrolyzed by dissolving in 3 mL of THF, adding 10 mL of 1M NaOH, stirring at 50° C. for 3 hours, then 75° C. without the condenser for 1 hour to distill off the THF. The solution was poured into water and adjusted to pH 6 with acetic acid. This solution was extracted three times with methylene chloride, dried over anhydrous sodium sulfate and the solvent was removed by evaporation under vacuum. The product was purified by recrystallization from ethanol/hexane to afford 0.223 g of the title compound, MS (DCI) M/Z 433 (M+H). NMR (CDCl$_3$) d 1.05 (m, 2H), 1.25 (m, 2H), 2.20 (m, 2H), 2.32 (s, 6H), 2.43 (m, 1H), 2.56 (m, 1H), 3.60 (m, 1H), 3.62 (m, 1H), 3.95 (m, 4H), 4.18 (m, 1H), 4.34 (m, 1H), 7.99 (dd, 1H, J=12), 8.69 (s, 1H).

EXAMPLE 552

7-(9-aminomethyl-1,4-dioxa-7-azaspiro[4.4]non-7-yl)-1-cyclopropyl-6-fluoro-1,8-naphthyridine-3-carboxylic acid hydrochloride Step 1. 7-(9-aminomethyl-1,4-dioxa-7-azaspiro[4.4]non-7-yl)-1-cyclopropyl-6-fluoro-1,8-naphthyridine-3-carboxylic acid ethyl ester In a reaction similar to that of Step 1 Example 496, into oven-dried glassware maintained under dry N2 were placed 1.1 g (7.6 mmol) of 9-amino-1,4-dioxa-7-azaspiro[4.4]nonane (from Step 5 Example 208), 0.497 g (1.6 mmol) of 7-chloro-1-cyclopropyl-6-fluoro-1,8-naphthyridine-3-carboxylic acid ethyl ester and 10 mL of dry pyridine. The reaction was stirred at 45° C. for 1.5 hours, then an additional 50 mg of the naphthyridine compound was added and the reaction was stirred an additional 3.5 hours. The solvent was removed in a rotary evaporator. The residue was dissolved in 1:1 methanol/methylene chloride, heated with charcoal, filtered, and the solvent was removed. The product was the product was purified by recrystallization from ethanol to afford after drying 0.454 g of the title compound. This material was taken directly to the next step.

Step 2. 7-(9-aminomethyl-1,4-dioxa-7-azaspiro[4.4]non-7-yl)-1-cyclopropyl-6-fluoro-1,8-naphthyridine-3-carboxylic acid hydrochloride The 0.454 g of the ester from Step 2 was hydrolyzed by dissolving in 6 mL of THF, adding 3 mL of 1M NaOH, stirring at 65° C. for 3.5 hours. The solution was cooled and adjusted to pH 7-8 with 1N HCl. The resulting precipitate was isolated by filtration, washed with water and dried under vacuum at room temperature. The product was dissolved in 2 mL of 1N HCl, the solvent removed at 35° C., and dried under vacuum. The product was then suspended in ethanol and was heated with stirring at reflux for 2 hours. The product was isolated by filtration, washed with methanol, and dried under vacuum to afford 0.262 g of the title compound, mp 276-278 dec. MS (DCI/i-bu) M/Z 447 (M+C$_4$H$_9$) 433 (M+C$_3$H$_7$), 391 (M-Cl). NMR (TFA) d 1.30 (m, 2H), 1.52 (m, 2H), 4.10 (m, 1H, J=3 Hz), 4.2 (m, 4H), 4.53 (m, 4H), 4.60 (m, 1H), 8.17 (d, 1H, J=12 Hz), 9.16 (s, 1H). Analysis calculated for C$_{18}$H$_{20}$ClFN$_4$O$_5$·H$_2$O: C, 48.60; H, 4.98; N, 12.59. Found: C, 48.50; H, 4.53; N, 12.51.

EXAMPLE 553

Assay of In Vitro Antibacterial Activity

The activity of the compounds of the present invention was tested against a wide variety of bacteria using standard assay procedures. Minimum inhibitory concentrations (MICs) were determined by the agar dilution method, described below, using Brain Heart Infusion agar.

Twelve petri dishes were prepared, each containing successive aqueous 2-fold dilutions of the test compounds mixed with 10 mL of sterilized Brain Heart Infusion (BHI) agar. Each plate was inoculated with 100-fold (or 10-fold, for slow-growing strains such as Micrococcus and Streptococcus) dilutions of up to 32 different microorganisms using a Steers replicator block calibrated to deliver approximately $10^4$ colony forming units (CFUs). The inoculated plates were incubated at about 35°-37° C. for approximately 20-24 hours. In addition, a control plate, using BHI agar containing no test compound, was prepared and incubated at the beginning and at the end of each test. Ciprofloxacin was used as the reference antibiotic.

After incubation, each petri dish was observed for the presence or absence of microorganism growth. The MIC was defined as the lowest concentration of test compound yielding no growth (a slight haze or sparsely isolated colonies at the inoculum spot as compared to the growth control contaning no test compound.

The results of testing, which demonstrate the antibacterial activity of the compounds of the present invention, are shown in Table 21 below.

TABLE 21

| | In Vitro Antibacterial Activity | | | | |
|---|---|---|---|---|---|
| | MIC values Example number | | | | |
| Examples | 159 | 274 | 330 | 445 | Cipro |
| Staphylococcus aureus ATCC 6538P | 0.2 | 0.05 | 0.1 | 0.2 | 0.2 |
| Staphylococcus aureus CMX 553 | | | | 0.39 | 0.78 |
| Staphylococcus aureus A5177 | 0.39 | 0.1 | 0.2 | 0.39 | 0.39 |
| Staphylococcus aureus 45 | 0.78 | | | 0.39 | 0.78 |
| Staphylococcus aureus A-5278 | | 0.05 | 0.1 | | 0.39 |
| Staphylococcus aureus 45 RAR2 | | | | 0.78 | |
| Staphylococcus aureus CMX 553 | 0.78 | 0.1 | 0.2 | | 0.78 |
| Staphylococcus aureus 642A | 0.39 | 0.1 | 0.2 | 0.39 | 0.39 |
| Staphylococcus aureus NCTC 10649 | 0.2 | 0.05 | 0.1 | 0.2 | 0.39 |
| Staphylococcus aureus 1775 | 100 | 6.2 | 6.2 | | >100 |
| Staphylococcus epidermidis 3519 | 0.78 | 0.1 | 0.2 | 0.39 | 0.2 |
| Micrococcus luteus ATCC 9341 | 12.5 | 0.39 | 1.56 | 12.5 | 1.56 |
| Micrococcus luteus ATCC 4698 | 6.2 | 0.39 | 0.78 | 12.5 | 0.78 |
| Enterococcus faecium ATCC 8043 | 0.78 | 0.39 | 0.78 | 1.56 | 0.39 |
| Streptococcus bovis A5169 | 0.78 | 0.39 | 3.1 | 1.56 | 1.56 |
| Streptococcus agalactaciae CMX 508 | 0.78 | 0.2 | 0.78 | 1.58 | 0.39 |
| Streptococcus pyogenes EES61 | 0.39 | 0.2 | 1.56 | 0.78 | 0.39 |
| Streptococcus pyogenes 2548 INDUC | 0.39 | 0.1 | 0.78 | 0.2 | 0.39 |

TABLE 21-continued

In Vitro Antibacterial Activity

| Examples | MIC values Example number | | | | |
|---|---|---|---|---|---|
| | 159 | 274 | 330 | 445 | Cipro |
| *Streptococcus pyogenes* 930 CONST | 0.39 | 0.2 | 1.56 | 0.78 | 0.78 |
| *Escherichia coli* JUHL | 0.39 | 0.05 | 1.56 | 1.56 | 0.02 |
| *Escherichia coli* SS | 0.02 | .002 | 0.01 | 0.2 | .005 |
| *Escherichia coli* DC-2 | 6.2 | 0.78 | 12.5 | 12.5 | 0.2 |
| *Escherichia coli* H560 | 0.2 | 0.2 | 1.56 | 1.56 | 0.01 |
| *Escherichia coli* KNK 437 | 3.1 | 0.78 | 12.5 | 12.5 | 0.2 |
| *Enterobacter aerogenes* ATCC 13048 | 0.78 | 0.2 | 6.2 | 3.1 | 0.05 |
| *Klebsiella pneumoniae* ATCC 8045 | 0.39 | 0.05 | 0.78 | 1.56 | 0.02 |
| *Providencia stuartii* CMX 640 | 25 | 0.78 | 50 | >100 | 0.78 |
| *Pseudomonas aeruginosa* BMH10 | 3.1 | 1.56 | 12.5 | 12.5 | 0.05 |
| *Pseudomonas aeruginosa* A5007 | 3.1 | 1.56 | 12.5 | 12.5 | 0.1 |
| *Pseudomonas aeruginosa* K799/WT | 3.1 | 1.56 | 12.5 | 12.5 | 0.1 |
| *Pseudomonas aeruginosa* K599/61 | 0.39 | 0.1 | 0.78 | 1.56 | 0.02 |
| *Pseudomonas aeruginosa* 5263 | | | >100 | | 12.5 |
| *Pseudomonas aeruginosa* 2862 | | | >100 | | 25 |
| *Pseudomonas cepacia* 2961 | 50 | 6.2 | 12.5 | 50 | 3.1 |
| *Acinetobacter* SP CMX 699 | 0.78 | 0.2 | 3.1 | 6.2 | 0.39 |

EXAMPLE 554

Assay of In Vivo Antibacterial Activity

The in vivo antibacterial activity of one of the compounds of the present invention was determined by studying the protection of CF-1 female mice from bacterial challenge. The test compound was 7-(2-dimethylaminomethyl-1,4-dioxa-7-azaspiro[4.4]non-7-yl)-6-fluoro-1-(2,4-difluorophenyl)-1,8-naphthyridine-3-carboxylic acid (prepared in Example 445). Aqueous solutions of the compound were made by dissolving it in dilute NaOH and diluting with distilled water to the desired volume.

The median lethal dose of the test organism was then determined as follows: After 18 hours incubation, a culture of *Staphylococcus aureus* NCTC 10649 was serially diluted by using 10-fold dilutions in 5% (w/v) hog gastric mucin. 0.5 mL samples, of dilution from $10^{-1}$ to $10^{-8}$, were injected intraperitoneally into mice. The LD$_{50}$ for the test organism was calculated from the cumulative mortalities on the sixth day by the using the Reed and Muench procedure (Reed, L. J., and H. Muench, Amer. J. Hygiene, 27, 493 (1938)).

The 18 hour culture of the test organism was then diluted in 5% (w/v) hog gastric mucin to obtain 100 times the LD$_{50}$, and 0.5 mL was injected intraperitoneally into mice. The mice were treated subcutaneously or orally with a specific amount of the test compound divided equally to be administered at 1 and 5 hr after infection. A group of 10 animals each for at least three dose levels was thus treated, and the deaths were recorded daily for 6 days. Ten mice were left untreated as infection controls. ED$_{50}$ values were calculated from the cumulative mortalities on the sixth day after infection by using the trimmed version of the Logit method (Hamilton, M. A., R. C. Russo, and R. V. Thurston, Environ. Sci. Technol. 11, 714 (1977)).

When compiled, the data showed an oral ED$_{50}$ of 6.0 mg/kg/day and a subcutaneous ED$_{50}$ of 5.0 mg/kg/day. These results support the particularly favorable efficacy of the compounds of the present invention against known bacterial pathogens.

The foregoing disclosure is merely illustrative of the invention and is not intended to limit the invention to the disclosed compounds. Variations and changes which are obvious to one skilled in the art are intended to be within the scope and nature of the invention which are defined in the appended claims.

We claim:

1. A compound of the formula

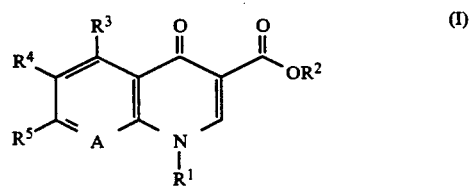

or a pharmaceutically acceptable salt, ester or amide thereof, wherein R$^1$ is selected from the group consisting of (a) lower alkyl, (b) halo(lower alkyl), (c) lower alkyl-(alkynyl), (d) lower cycloalkyl, (e) lower alkylamino, (f) nitrogen-containing aromatic heterocycle selected from the group consisting of pyridine, pyrazine, pyrimidine, pyrrole, pyrazole, imidazole, thiazole, oxazole and isooxazole, (g) bicyclic alkyl and (h) phenyl;

R$^2$ is selected from the group consisting of hydrogen, lower alkyl, a pharmaceutically acceptable cation, and a prodrug ester group selected from the group consisting of pivoyloxymethyl, acetoxymethyl, phthalidyl, indanyl and methoxymethyl;

R$^3$ and R$^4$ are independently selected from the group consisting of hydrogen, halogen, amino, and lower alkyl;

R$^5$ is selected from the group consisting of (a) a nitrogen-containing heterocycle having the formula

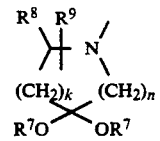

wherein k=1 or 2, n=1 or 2 and k+n=2 or 3; R$^7$ is lower alkyl; and R$^8$ and R$^9$ are independently selected from the group consisting of hydrogen, amino, lower alkylamino, amino(lower alkyl), lower alkyl, halo(lower alkyl), mono- or dipeptide-substituted amino, and mono- or dipeptide-substituted amino(lower alkyl), said mono- or dipeptide substitutents comprising one or two amino acids attached via an amide linkage and independently selected from the group consisting of cyclohexylalanine, cyclohexlglycine, and naturally occurring amino acids; and (b) a nitrogen-containing spiro-bicyclic-heterocycle having the formula

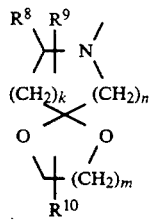

wherein k=1 or 2, n=1 or 2 and k+n=2 or 3; m=1 or 2; $R^8$ and $R^9$ are independently selected from the group consisting of hydrogen, amino, lower alkylamino, amino(lower alkyl), halo(lower alkyl), mono- or dipeptide-substituted amino, and mono- or dipeptide-substituted amino(lower alkyl), said mono- or dipeptide substituents being as defined above; and $R^{10}$ is selected from the group consisting of hydrogen, amino, lower alkylamino, amino(lower alkyl), lower alkyl, halo(lower alkyl), hydroxy(lower alkyl), lower alkoxy(lower alkyl), amino acid-substituted amino, and amino acid-substituted amino(lower alkyl); and A is N or C-$R^6$, wherein $R^6$ is selected from the group consisting of hydrogen, halogen, lower alkyl, and lower alkoxy;

with the proviso that when $R^5$ is a nitrogen-containing spiro-bicyclic-heterocycle having the formula

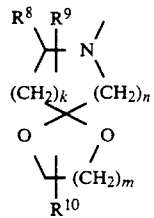

where m=1 and $R^{10}$ is hydrogen, then $R^8$ and $R^9$ may not both be hydrogen.

2. A compound according to claim 1 wherein $R^5$ is a nitrogen-containing spiro-bicyclic-heterocycle having the formula

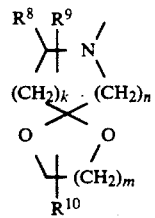

wherein k, n, m, $R^8$, $R^9$ and $R^{10}$ are as previously described.

3. A compound according to claim 2 wherein k=1, m=1 and n=1.

4. A compound according to claim 3 wherein $R^9$ is amino.

5. A compound according to claim 3 wherein $R^{10}$ is dimethylaminomethyl.

6. A compound according to claim 1 wherein $R^5$ is a nitrogen-containing heterocycle having the formula

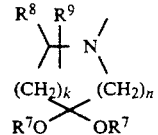

wherein k, n, $R^7$, $R^8$ and $R^9$ are as previously described.

7. A compound selected from the group consisting of
7-(3,3-dimethoxypyrrolidin-1-yl)-1-(2,4-difluorophenyl)-6-fluoro-1,4-dihydro-4-oxo-3-quinolinecarboxylic acid;

1-cyclopropyl-7-(3,3-dimethoxypyrrolidin-1-yl)-6-fluoro-1,4-dihydro-4-oxo-3-quinolinecarboxylic acid;

1-(2,4-difluorophenyl)-7-(1,5-dioxa-8-azaspiro[5.4]dec-8-yl)-6-fluoro-1,4-dihydro-4-oxo-3-quinolinecarboxylic acid;

1-cyclopropyl-6,8-difluoro-7-(1,5-dioxa-8-azaspiro[5.4]dec-8-yl)-1,4-dihydro-4-oxo-3-quinolinecarboxylic acid;

1-(2,4-difluorophenyl)-7-(1,4-dioxa-2-methyl-7-azaspiro[4.4]non-7-yl)-6-fluoro-1,4-dihydro-4-oxo-3-quinolinecarboxylic acid;

1-(2,4-difluorophenyl)-7-(1,4-dioxa-2-hydroxymethyl-7-azaspiro[4.4]non-7-yl)-6-fluoro-1,4-dihydro-4-oxo-3-quinolinecarboxylic acid;

1-(2,4-difluorophenyl)-7-(2-aminomethyl-1,4-dioxa-7-azaspiro[4.4]non-7-yl)-6-fluoro-1,4-dihydro-4-oxo-3-quinolinecarboxylic acid dihydrochloride;

1-(2,4-difluorophenyl)-7-(2-dimethylaminomethyl-1,4-dioxa-7-azaspiro[4.4]non-7-yl)-6-fluoro-1,4-dihydro-4-oxo-3-quinolinecarboxylic acid;

7-(3,3-dimethoxy-4-methylpyrrolidin-1-yl)-1-(2,4-difluorophenyl)-6-fluoro-1,4-dihydro-4-oxo-3-quinolinecarboxylic acid;

1-cyclopropyl-6,8-difluoro-7-(3,3-dimethoxy-4-methylpyrrolidin-1-yl)-1,4-dihydro-4-oxo-3-quinolinecarboxylic acid;

1-(2,4-difluorophenyl)-7-(1,5-dioxa-9-azaspiro[5.5]undec-9-yl)-6-fluoro-1,4-dihydro-4-oxo-3-quinolinecarboxylic acid;

1-cyclopropyl-6-fluoro-7-(9-amino-1,4-dioxa-7-azaspiro[4.4]non-7-yl)-1,4-dihydro-4-oxo-3-quinolinecarboxylic acid hydrochloride;

1-cyclopropyl-6,8-difluro-7-(9-amino-1,4-dioxa-7-azaspiro[4.4]non-7-yl)-1,4-dihydro-4-oxo-3-quinolinecarboxylic acid;

1-(2,4-difluorophenyl)-7-(3,3-dimethoxypyrrolidin-1-yl)-6-fluoro-1,8-naphthyridine-3-carboxylic acid;

1-(2,4-difluorophenyl)-7-(1,5-dioxa-8-azaspiro[5.4]dec-8-yl)-6-fluoro-1,8-naphthyridine-3-carboxylic acid;

1-(2,4-difluorophenyl)-7-(1,4-dioxa-2-methyl-7-azaspiro[4.4]non-7-yl)-6-fluoro-1,8-naphthyridine-3-carboxylic acid;

7-(1,4-dioxa-2-methyl-7-azaspiro[4.4]non-7-yl)-6-fluoro-1-(4-fluorophenyl)-1,8-naphthyridine-3-carboxylic acid;

7-(2-aminomethyl-1,4-dioxa-7-azaspiro[4.4]non-7-yl)-6-fluoro-1-(2,4-difluorophenyl)-1,8-naphthyridine-3-carboxylic acid dihydrochloride;

7-(3,3-dimethoxy-4-methylpyrrolidin-1-yl)-6-fluoro-1-(2,4-difluorophenyl)-1,8-naphthyridine-3-carboxylic acid;

7-(2-dimethylaminomethyl-1,4-dioxa-7-azaspiro[4.4]non-7-yl)-6-fluoro-1-(2,4-difluorophenyl)-1,8-naphthyridine-3-carboxylic acid;

7-(9-amino-1,4-dioxa-7-azaspiro[4.4]non-7-yl)-6-fluoro-1-(2,4-difluorophenyl)-1,8-naphthyridine-3-carboxylic acid hydrochloride;

7-(9-aminomethyl-1,4-dioxa-7-azaspiro[4.4]non-7-yl)-6-fluoro-1-(2,4-difluorophenyl)-1,8-naphthyridine-3-carboxylic acid hydrochloride;

7-(1,5-dioxa-9-azaspiro[5.5]undec-9-yl)-6-fluoro-1-(2,4-difluorophenyl)-1,8-naphthyridine-3-carboxylic acid;

7-(2-aminomethyl-1,4-dioxa-8-azaspiro[4.5]dec-8-yl)-6-fluoro-1-(2,4-difluorophenyl)-1,8-naphthyridine-3-carboxylic acid hydrochloride;

7-(1,5-dioxa-9-azaspiro[5.5]undec-9-yl)-6-fluoro-1-(2,4-difluorophenyl)-1,8-naphthyridine-3-carboxylic acid;

7-(2-aminomethyl-1,4-dioxa-8-azaspiro[4.5]dec-8-yl)-6-fluoro-1-(2,4-difluorophenyl)-1,8-naphthyridine-3-carboxylic acid hydrochloride;

1-(2,4-difluorophenyl)-6-fluoro-7-(2-methylaminomethyl-1,4-dioxa-8-azaspiro[4.5]dec-8-yl)-1,8-naphthyridine-3-carboxylic acid hydrochloride;

1-(2,4-difluorophenyl)-6-fluoro-7-(2-methylaminomethyl-1,4-dioxa-8-azaspiro[4.5]dec-8-yl)-1,8-naphthyridine-3-carboxylic acid;

7-(2-aminomethyl-1,4-dioxa-7-azaspiro[4.4]non-7yl)-1-cyclopropyl-6-fluoro-1,8-naphthyridine-3-carboxylic acid dihydrochloride;

7-(2-dimethylaminomethyl-1,4-dioxa-7-azaspiro[4.4]non-7-yl)-1-cyclopropyl-6-fluoro-1,8-naphthyridine-3-carboxylic acid;

7-(9-aminomethyl-1,4-dioxa-7-azaspiro[4.4]non-7-yl)-1-cyclopropyl-6-fluoro-1,8-naphthyridine-3-carboxylic acid hydrochloride;

and pharmaceutically acceptable salts, esters, amides and prodrugs thereof.

8. A compound according to claim 7 selected from the group consisting of
1-cyclopropyl-6,8-difluoro-7-(9-amino-1,4-dioxa-7-azaspiro[4.4]non-7-yl)-1,4-dihydro-4-oxo-3-quinolinecarboxylic acid, and
7-(2-dimethylaminomethyl-1,4-dioxa-7-azaspiro[4.4]non-7-yl)-6-fluoro-1-(2,4-difluorophenyl)-1,8-naphthyridine-3-carboxylic acid.

9. A pharmaceutical composition comprising a therapeutically effective amount of a compound of claim 1 and a pharmaceutally acceptable carrier.

10. A method for treating or preventing bacterial infections in a human or animal host, comprising administering a therapeutically effective amount of a compound of claim 1 to a human or animal in need thereof.

* * * * *